(12) United States Patent
Bonfanti et al.

(10) Patent No.: US 8,278,455 B2
(45) Date of Patent: *Oct. 2, 2012

(54) 5- OR 6-SUBSTITUTED BENZIMIDAZOLE DERIVATIVES AS INHIBITORS OF RESPIRATORY SYNCYTIAL VIRUS REPLICATION

(75) Inventors: Jean-François Bonfanti, Andé (FR); Koenraad Jozef Lodewijk Andries, Beerse (BE); Jérôme Michel Claude Fortin, Igoville (FR); Philippe Muller, Andé (FR); Frédéric Marc Maurice Doublet, Isneauville (FR); Christophe Meyer, Les Authieux s/l Port St Ouen (FR); Rudy Edmond Willebrords, Merksplas (BE); Tom Valerius Josepha Gevers, Vosselaar (BE); Philip Maria Martha Bern Timmerman, Hasselt (BE)

(73) Assignee: Janssen Pharmaceutica N.V. (BE)

( * ) Notice: Subject to any disclaimer, the term of this patent is extended or adjusted under 35 U.S.C. 154(b) by 761 days.

This patent is subject to a terminal disclaimer.

(21) Appl. No.: 12/253,450

(22) Filed: Oct. 17, 2008

(65) Prior Publication Data

US 2009/0062278 A1 Mar. 5, 2009

Related U.S. Application Data

(63) Continuation of application No. 10/596,521, filed as application No. PCT/EP2004/053618 on Dec. 20, 2004, now abandoned.

(60) Provisional application No. 60/566,867, filed on Apr. 30, 2004.

(30) Foreign Application Priority Data

Dec. 18, 2003 (EP) .................................. 03104806

(51) Int. Cl.
*A61K 31/4439* (2006.01)
*C07D 401/06* (2006.01)

(52) U.S. Cl. ..................... 546/273.4; 544/364; 546/194; 514/338

(58) Field of Classification Search ................ 546/273.4
See application file for complete search history.

(56) References Cited

U.S. PATENT DOCUMENTS

| | | | | |
|---|---|---|---|---|
| 4,025,621 | A | * | 5/1977 | Purdy .......................... 424/601 |
| 6,747,028 | B1 | | 6/2004 | Janssens et al. |
| 7,071,192 | B1 | | 7/2006 | Janssens et al. |
| 7,173,034 | B2 | | 2/2007 | Janssens et al. |

FOREIGN PATENT DOCUMENTS

| EP | 0005318 B1 | 11/1979 |
|---|---|---|
| EP | 0099139 B1 | 1/1984 |
| EP | 0145037 B1 | 6/1985 |
| WO | WO 92/01687 A1 | 2/1992 |
| WO | WO 01/00611 A1 | 1/2001 |
| WO | WO 01/00612 A1 | 1/2001 |
| WO | WO 01/00615 A1 | 1/2001 |
| WO | WO 02/090347 A1 | 11/2002 |
| WO | WO 02/092575 A1 | 11/2002 |
| WO | WO 03/053939 A1 | 7/2003 |

OTHER PUBLICATIONS

Benet, et al., "Pharmacokinetics: The Dynamics of Drug Absorption, Distribution, and Eliminartion." *Goodman and Gilman's The Pharmacological Basis of Therapeutics*, Eighth Edition, pp. 13-20, McGraw-Hill Inc., 1996.

Janssens, F. et al., "New Antihistamine N-Heterocyclic 4-Piperidinamines.2. Synthesis and Antihistaminic Activity of 1-(4-Fluorophenyl)-1H-Benzimidazol-2-Amines." *Journal of Medicinal Chemsitry*, Dec. 1985, vol. 28, No. 121, pp. 1934-1943, American Chemical Society, Washington, US.

Wyde et al., "CL387626 Exhibits Marked and Unusual Antiviral Activity Against Respiratory Syncytial Virus in Tissue Culture and In Cotton Rats." *Antiviral Research*, 1998, vol. 38, pp. 31-42.

CA 29:16897, 1935.

* cited by examiner

*Primary Examiner* — Laura L. Stockton
(74) *Attorney, Agent, or Firm* — Mary A. Appollina

(57) ABSTRACT

The present invention concerns 5- or 6-substituted-benzimidazole derivatives having inhibitory activity on the replication of the respiratory syncytial virus and having the formula

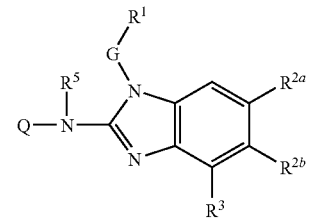

a prodrug, N-oxide, addition salt, quaternary amine, metal complex or stereochemically isomeric form thereof wherein Q is $Ar^2$, $R^6$, pyrrolidinyl substituted with $R^6$, piperidinyl substituted with $R^6$ or homopiperidinyl substituted with $R^6$, G is a direct bond or optionally substituted $C_{1-10}$alkanediyl; $R^1$ is $Ar^1$ or a monocyclic or bicyclic heterocycle; one of $R^{2a}$ and $R^{2b}$ is cyano$C_{1-6}$alkyl, cyano$C_{2-6}$alkenyl, $Ar^3C_{1-6}$alkyl, $Het^1C_{1-6}$alkyl, $N(R^{8a}R^{8b})C_{1-6}$alkyl, $Ar^3C_{2-6}$alkenyl, $Het^1C_{2-6}$alkenyl, $Ar^3$amino$C_{1-6}$alkyl, $Het^1$amino$C_{1-6}$alkyl, $Ar^3$thio$C_{1-6}$alkyl, $Het^1$thio$C_{1-6}$alkyl, $Ar^3$sulfonyl$C_{1-6}$alkyl, $Het^1$sulfonyl$C_{1-6}$alkyl, $Ar^3$aminocarbonyl, $Het^1$aminocarbonyl, $Ar^3(CH_2)_n$amino-carbonyl, $Het^1(CH_2)_n$aminocarbonyl, $Ar^3$carbonylamino, $Het^1$carbonylamino, $Ar^3(CH_2)_n$carbonylamino, $Het^1(CH_2)_n$carbonylamino, and the other one of $R^{2a}$ and $R^{2b}$ is hydrogen; in case $R^{2a}$ is hydrogen, then $R^3$ is hydrogen;
in case $R^{2b}$ is hydrogen, the $R^3$ is hydrogen or $C_{1-6}$alkyl. It further concerns their preparation and compositions comprising them, as well as their use as a medicine.

12 Claims, No Drawings

5- OR 6-SUBSTITUTED BENZIMIDAZOLE DERIVATIVES AS INHIBITORS OF RESPIRATORY SYNCYTIAL VIRUS REPLICATION

CROSS REFERENCE TO RELATED APPLICATIONS

This application is a continuation of U.S. Application Ser. No. 10/596,521 filed Jun. 15, 2006, now abandoned, which is the national stage of PCT Application No. PCT/EP2004/053618, filed Dec. 20, 2004, which application claims priority from European Patent Application No. 03104806.9, filed 18 Dec. 2003 and U.S. provisional Application No. 60/566,867, filed 30 April 2004, the entire disclosures of which are hereby incorporated in their entirely.

The present invention is concerned with 5- or 6-substituted-benzimidazole derivatives having antiviral activity, in particular, having an inhibitory activity on the replication of the respiratory syncytial virus (RSV). It further concerns the preparation thereof and compositions comprising these compounds.

Human RSV or Respiratory Syncytial Virus is a large RNA virus, member of the family of Paramyxoviridae, subfamily pneumovirinae together with bovine RSV virus. Human RSV is responsible for a spectrum of respiratory tract diseases in people of all ages throughout the world. It is the major cause of lower respiratory tract illness during infancy and childhood. Over half of all infants encounter RSV in their first year of life, and almost all within their first two years. The infection in young children can cause lung damage that persists for years and may contribute to chronic lung disease in later life (chronic wheezing, asthma). Older children and adults often suffer from a (bad) common cold upon RSV infection. In old age, susceptibility again increases, and RSV has been implicated in a number of outbreaks of pneumonia in the aged resulting in significant mortality.

Infection with a virus from a given subgroup does not protect against a subsequent infection with an RSV isolate from the same subgroup in the following winter season. Re-infection with RSV is thus common, despite the existence of only two subtypes, A and B.

Today only three drugs have been approved for use against RSV infection. A first one is ribavirin, a nucleoside analogue, provides an aerosol treatment for serious RSV infection in hospitalized children. The aerosol route of administration, the toxicity (risk of teratogenicity), the cost and the highly variable efficacy limit its use. The other two drugs, RespiGam® and palivizumab, polyclonal and monoclonal antibody immunostimulants, are intended to be used in a preventive way.

Other attempts to develop a safe and effective RSV vaccine have all met with failure thus far. Inactivated vaccines failed to protect against disease, and in fact in some cases enhanced disease during subsequent infection. Life attenuated vaccines have been tried with limited success. Clearly there is a need for an efficacious non-toxic and easy to administer drug against RSV replication.

Previously, benzimidazoles and imidazopyridines as inhibitors of RSV replication have been described in WO 01/00611, WO 01/00612 and WO 01/00615.

Several series of benzimidazolyl and imidazopyridinyl piperidines have been described in patents, patent applications and publications of Janssen Pharmaceutica N.V. as compounds possessing antihistaminic properties. See for example EP-A-5 318, EP-A-99 139, EP-A-145 037, WO-92/01687, Janssens F. et al. in Journal of Medicinal Chemistry, Am. Chem. Soc., Vol. 28, no. 12, pp. 1934-1943 (1985).

The present invention concerns inhibitors of RSV replication, which can be represented by formula (I)

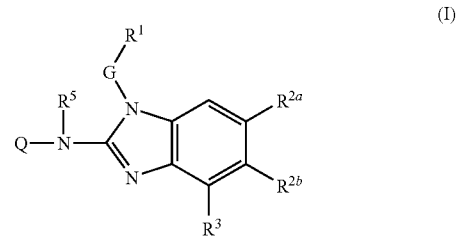

(I)

their prodrugs, N-oxides, addition salts, quaternary amines, metal complexes and stereochemically isomeric forms wherein Q is $Ar^2$, $R^{6a}$, pyrrolidinyl substituted with $R^6$, piperidinyl substituted with $R^6$ or homopiperidinyl substituted with $R^6$;

G is a direct bond or $C_{1-10}$alkanediyl optionally substituted with one or more substituents individually selected from the group consisting of hydroxy, $C_{1-6}$alkyloxy, $Ar^1C_{1-6}$alkyloxy, $C_{1-6}$alkylthio, $Ar^1C_{1-6}$alkylthio, HO(—CH$_2$—CH$_2$—O)$_n$—, $C_{1-6}$alkyloxy(—CH$_2$—CH$_2$—O)$_n$— and $Ar^1C_{1-6}$alkyloxy(—CH$_2$—CH$_2$—O)$_n$—;

$R^1$ is $Ar^1$ or a monocyclic or bicyclic heterocycle being selected from piperidinyl, piperazinyl, pyridyl, pyrazinyl, pyridazinyl, pyrimidinyl, furanyl, tetrahydrofuranyl, thienyl, pyrrolyl, thiazolyl, oxazolyl, imidazolyl, isothiazolyl, pyrazolyl, isoxazolyl, oxadiazolyl, quinolinyl, quinoxalinyl, benzofuranyl, benzothienyl, benzimidazolyl, benzoxazolyl, benzthiazolyl, pyridopyridyl, naphthiridinyl, 1H-imidazo[4,5-b]pyridinyl, 3H-imidazo[4,5-b]pyridinyl, imidazo[1,2-a]-pyridinyl, 2,3-dihydro-1,4-dioxino[2,3-b]pyridyl or a radical of formula

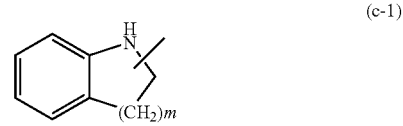

(c-1)

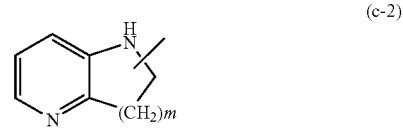

(c-2)

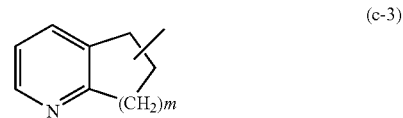

(c-3)

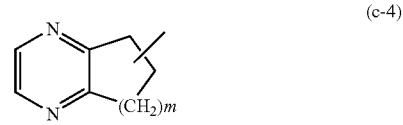

(c-4)

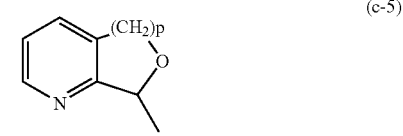

(c-5)

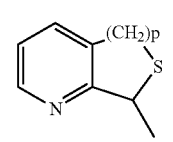
(c-6)

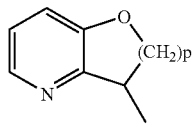
(c-7)

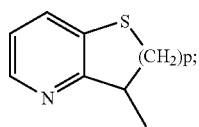
(c-8)

wherein each of said monocyclic or bicyclic heterocycles may optionally be substituted with 1 or where possible more, such as 2, 3, 4 or 5, substituents individually selected from the group of substituents consisting of halo, hydroxy, amino, cyano, carboxyl, $C_{1-6}$alkyl, $C_{1-6}$alkyloxy, $C_{1-6}$alkylthio, $C_{1-6}$alkyloxy$C_{1-6}$alkyl, $Ar^1$, $Ar^1C_{1-6}$alkyl, $Ar^1C_{1-6}$alkyloxy, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyl-$SO_2$—$NR^{4a}$—, $Ar^1$—$SO_2$—$NR^{4a}$—, $C_{1-6}$alkyloxycarbonyl, —C(=O)—$NR^{4a}R^{4b}$, HO(—$CH_2$—$CH_2$—O)$_n$—, halo(—$CH_2$—$CH_2$—O)$_n$—, $C_{1-6}$alkyloxy(—$CH_2$—$CH_2$—O)$_n$—, $Ar^1C_{1-6}$alkyloxy(—$CH_2$—$CH_2$—O)$_n$— and mono- and di($C_{1-6}$alkyl)amino(—$CH_2$—$CH_2$—O)$_n$;

one of $R^{2a}$ and $R^{2b}$ is cyano$C_{1-6}$alkyl, cyano$C_{2-6}$alkenyl, $Ar^3C_{1-6}$alkyl, $(Ar^3)(OH)C_{1-6}$alkyl, Het-$C_{1-6}$alkyl, $N(R^{8a}R^{8b})C_{1-6}$alkyl, $Ar^3C_{2-6}$alkenyl, Het-$C_{2-6}$alkenyl, $Ar^3$amino$C_{1-6}$alkyl, Het-amino$C_{1-6}$alkyl, Het-$C_{1-6}$alkylamino$C_{1-6}$alkyl, $Ar^3$thio$C_{1-6}$alkyl, Het-thio$C_{1-6}$alkyl, $Ar^3$sulfonyl$C_{1-6}$alkyl, Het-sulfonyl$C_{1-6}$alkyl, $Ar^3$aminocarbonyl, Het-aminocarbonyl, $Ar^3(CH_2)_n$aminocarbonyl, Het-$(CH_2)_n$aminocarbonyl, $Ar^3$carbonylamino, Het-carbonylamino, $Ar^3(CH_2)_n$carbonylamino, Het-$(CH_2)_n$carbonylamino or $Ar^3(CH_2)_n$amino; and the other one of $R^{2a}$ and $R^{2b}$ is hydrogen;

in case $R^{2a}$ is hydrogen, then $R^3$ is hydrogen;
in case $R^{2b}$ is hydrogen, then $R^3$ is hydrogen or $C_{1-6}$alkyl;
$R^{4a}$ and $R^{4b}$ can be the same or can be different relative to one another, and are each independently hydrogen or $C_{1-6}$alkyl; or $R^{4a}$ and $R^{4b}$ taken together may form a bivalent radical of formula —$(CH_2)_s$— wherein s is 4 or 5;
$R^5$ is hydrogen or $C_{1-6}$alkyl;
$R^6$ is hydrogen or $C_{1-6}$alkyl optionally substituted with one or more substituents each independently selected from the group consisting of trifluoromethyl, $NR^{7a}R^{7b}$, $C_{3-7}$cycloalkyl, $Ar^2$, hydroxy, $C_{1-4}$alkoxy, $C_{1-4}$alkylthio, $Ar^2$-oxy-, $Ar^2$-thio-, $Ar^2(CH_2)_n$oxy, $Ar^2(CH_2)_n$thio, hydroxycarbonyl, aminocarbonyl, $C_{1-4}$alkylcarbonyl, $Ar^2$carbonyl, $C_{1-4}$alkoxycarbonyl, $Ar^2(CH_2)_n$carbonyl, aminocarbonyloxy, $C_{1-4}$alkylcarbonyloxy, $Ar^2$carbonyloxy, $Ar^2(CH_2)_n$carbonyloxy, $C_{1-4}$alkoxycarbonyl($CH_2)_n$oxy, mono- or di($C_{1-4}$alkyl)aminocarbonyl, mono- or di($C_{1-4}$alkyl)-aminocarbonyloxy, aminosulfonyl, mono- or di($C_{1-4}$alkyl) aminosulfonyl or a heterocycle selected from the group consisting of pyrrolidinyl, pyrrolyl, dihydropyrrolyl, imidazolyl, triazolyl, piperidinyl, homopiperidinyl, piperazinyl, dioxolanyl, dioxanyl, pyridyl and tetrahydropyridyl, wherein each of said heterocycle may optionally be substituted with one or two radicals selected from oxo and $C_{1-6}$alkyl;

$R^{6a}$ is $C_{1-6}$alkyl substituted with one or more substituents each independently selected from the group consisting of trifluoromethyl, $NR^{7a}R^{7b}$, $C_{3-7}$cycloalkyl, $Ar^2$, hydroxy, $C_{1-4}$alkoxy, $C_{1-4}$alkylthio, $Ar^2$-oxy-, $Ar^2$-thio-, $Ar^2(CH_2)_n$oxy, $Ar^2(CH_2)_n$thio, hydroxycarbonyl, aminocarbonyl, $C_{1-4}$alkylcarbonyl, $Ar^2$carbonyl, $C_{1-4}$alkoxycarbonyl, $Ar^2(CH_2)_n$carbonyl, aminocarbonyloxy, $C_{1-4}$alkylcarbonyl-oxy, $Ar^2$carbonyloxy, $Ar^2(CH_2)_n$carbonyloxy, $C_{1-4}$alkoxycarbonyl($CH_2)_n$oxy, mono- or di($C_{1-4}$alkyl)aminocarbonyl, mono- or di($C_{1-4}$alkyl)aminocarbonyloxy, aminosulfonyl, mono- or di($C_{1-4}$alkyl) aminosulfonyl or a heterocycle selected from the group consisting of pyrrolidinyl, pyrrolyl, dihydropyrrolyl, imidazolyl, triazolyl, piperidinyl, homopiperidinyl, piperazinyl, dioxolanyl, dioxanyl, pyridyl and tetrahydropyridyl, wherein each of said heterocycle may optionally be substituted with one or two radicals selected oxo and $C_{1-6}$alkyl;

$R^{7a}$ is hydrogen, $C_{1-6}$alkyl, formyl or $C_{1-6}$alkylcarbonyl;
$R^{7b}$ is hydrogen, $C_{1-6}$alkyl, formyl or $C_{1-6}$alkylcarbonyl;
$R^{8a}$ is $Ar^3$, $C_{1-6}$alkyl, hydroxy$C_{1-6}$alkyl, $C_{1-6}$alkoxy$C_{1-6}$alkyl, cyano$C_{1-6}$alkyl, amino$C_{1-6}$alkyl, mono- or di($C_{1-6}$alkyl)amino$C_{1-6}$alkyl, $Ar^3C_{1-6}$alkyl, Het-$C_{1-6}$alkyl, aminocarbonyl-$C_{1-6}$-alkyl, carboxyl-$C_{1-6}$-alkyl;
$R^{8b}$ is $Ar^3$, $C_{1-6}$alkyl, hydroxy$C_{1-6}$alkyl, $C_{1-6}$alkoxy$C_{1-6}$alkyl, cyano$C_{1-6}$alkyl, amino$C_{1-6}$alkyl, mono- or di($C_{1-6}$alkyl)amino$C_{1-6}$alkyl, $Ar^3C_{1-6}$alkyl, Het-$C_{1-6}$alkyl;

each n independently is 1, 2, 3 or 4;
each m independently is 1 or 2;
each p independently is 1 or 2;
$Ar^1$ is phenyl or phenyl substituted with 1 or more, such as 2, 3 or 4, substituents selected from halo, hydroxy, $C_{1-6}$alkyl, hydroxy$C_{1-6}$alkyl, polyhalo$C_{1-6}$alkyl, and $C_{1-6}$alkyloxy;

$Ar^2$ is phenyl or phenyl substituted with 1 or more, such as 2, 3 or 4, substituents selected from the group consisting of halo, hydroxy, amino, cyano, $C_{1-6}$alkyl, hydroxy$C_{1-6}$alkyl, polyhalo$C_{1-6}$alkyl, amino$C_{1-6}$alkyl, $C_{1-6}$alkyloxy, aminosulfonyl, aminocarbonyl, hydroxycarbonyl, $C_{1-4}$alkylcarbonyl, mono- or di($C_{1-4}$alkyl)amino, mono- or di($C_{1-4}$alkyl)aminocarbonyl, mono- or di($C_{1-4}$alkyl)aminosulfonyl, mono- or di($C_{1-4}$alkyl)amino$C_{1-6}$alkyl and $C_{1-4}$alkoxycarbonyl;

$Ar^3$ is phenyl, naphthalenyl, 1,2,3,4-tetrahydro-naphthalenyl or indanyl, wherein said phenyl, naphtyl, 1,2,3,4-tetrahydro-naphthalenyl or indanyl may optionally and each individually be substituted with one or more, such as 2, 3 or 4, substituents selected from the group consisting of halo, hydroxy, mercapto, amino, cyano, $C_{1-6}$alkyl, $C_{2-6}$alkenyl, $C_{2-6}$alkynyl, $Ar^1$, hydroxy$C_{1-6}$alkyl, polyhalo$C_{1-6}$alkyl, amino$C_{1-6}$alkyl, cyano$C_{1-6}$alkyl, aminocarbonyl, $C_{1-6}$alkyloxy, $C_{1-6}$alkylthio, $Ar^1$-oxy, $Ar^1$-thio, $Ar^1$-amino, aminosulfonyl, aminocarbonyl-$C_{1-6}$alkyl, hydroxyl-carbonyl-$C_{1-6}$alkyl, hydroxycarbonyl, $C_{1-4}$alkylcarbonyl, mono- or di($C_{1-4}$alkyl)amino, mono- or di($C_{1-4}$alkyl)aminocarbonyl, mono- or di($C_{1-4}$alkyl)aminosulfonyl, mono- or di($C_{1-4}$alkyl)amino$C_{1-6}$alkyl, $C_{1-4}$alkylcarbonylamino and $C_{1-4}$alkoxycarbonyl;

Het is a heterocycle being selected from tetrahydrofuranyl, tetrahydrothienyl, dioxanyl, dioxolanyl, pyrrolidinyl, pyrrolidinonyl, furanyl, thienyl, pyrrolyl, thiazolyl, oxazolyl, imidazolyl, isothiazolyl, pyrazolyl, isoxazolyl, oxadiazolyl, thiadiazolyl, piperidinyl, homopiperidinyl, piperazinyl, morpholinyl, pyridyl, pyrazinyl, pyridazinyl, pyrimidinyl, tetrahydroquinolinyl, quinolinyl, isoquinolinyl, benzodioxanyl, benzodioxolyl, indolinyl, indolyl, each of said heterocycle may optionally be substituted with oxo, amino, Ar$^1$, C$_{1-4}$alkyl, aminoC$_{1-4}$alkyl, hydroxyC$_{1-6}$alkyl, Ar$^1$C$_{1-4}$alkyl, mono- or di(C$_{1-6}$alkyl)aminoC$_{1-6}$alkyl, mono- or di(C$_{1-6}$alkyl)amino, or with two C$_{1-4}$alkyl radicals.

The invention also relates to the use of a compound of formula (I), or a prodrug, N-oxide, addition salt, quaternary amine, metal complex and stereochemically isomeric form thereof, for the manufacture of a medicament for inhibiting RSV replication. Or the invention relates to a method of inhibiting RSV replication in a warm-blooded animal said method comprising the administration of an effective amount of a compound of formula (I), or a prodrug, N-oxide, addition salt, quaternary amine, metal complex and stereochemically isomeric form thereof.

In a further aspect, this invention relates to novel compounds of formula (I) as well as methods for preparing these compounds.

The term prodrug as used throughout this specification and claims means the pharmacologically acceptable derivatives, e.g. esters and amides, such that the resulting biotransformation product of the derivative is the active drug as defined in the compounds of formula (I). The reference by Goodman and Gilman (The Pharmacological Basis of Therapeutics, 8$^{th}$ ed., McGraw-Hill, Int. Ed. 1992, "Biotransformation of Drugs", p. 13-15) describing prodrugs generally, is hereby incorporated. Prodrugs are characterized by a good aqueous solubility and bioavailability, and are readily metabolized into the active inhibitors in vivo.

The terms 'C$_{1-10}$alkanediyl optionally substituted with one or more substituents' and 'C$_{1-6}$alkyl optionally substituted with one or more substituents' such as used in the definition of G and respectively R$^6$ or R$^{6a}$ are meant to comprise C$_{1-10}$alkanediyl or C$_{1-6}$alkyl radicals having two or more substituents, for example two, three, four, five or six substituents, in particular two or three substituents, further in particular two substituents. The upper limit of the number of substituents is determined by the number of hydrogen atoms that can be replaced as well as by the general properties of the substituents such as their bulkiness, these properties allowing the skilled person to determine said upper limit.

As used in the foregoing and hereinafter, 'polyhaloC$_{1-6}$alkyl' as a group or part of a group, e.g. in polyhaloC$_{1-6}$alkyloxy, is defined as mono- or polyhalo substituted C$_{1-6}$alkyl, in particular C$_{1-6}$alkyl substituted with up to one, two, three, four, five, six, or more halo atoms, such as methyl or ethyl with one or more fluoro atoms, for example, difluoromethyl, trifluoromethyl, trifluoroethyl. Also included are perfluoro C$_{1-6}$alkyl groups, which are C$_{1-6}$alkyl groups wherein all hydrogen atoms are replaced by fluoro atoms, e.g. pentafluoroethyl. In case more than one halogen atom is attached to an alkyl group within the definition of polyhaloC$_{1-4}$alkyl, the halogen atoms may be the same or different.

Each of the monocyclic or bicyclic heterocycles in the definition of R$^1$ may optionally be substituted with 1 or where possible more substituents, such as 2, 3, 4 or 5, substituents. In particular, said heterocycles may optionally be substituted with up to 4, up to 3, up to 2 substituents, or up to 1 substituent.

Each Ar$^1$ or Ar$^2$ may be unsubstituted phenyl or phenyl substituted with 1 or more substituents, such as 5 or 4 substituents or, which is preferred, up to 3 substituents, or up to two substituents, or with one substituent. Ar$^3$ is phenyl, naphthalenyl, 1,2,3,4-tetrahydro-naphthalenyl or indanyl, which each may optionally with one or more substituents, such as 5 or 4 substituents or, which is preferred, up to 3 substituents, or up to two substituents, or with one substituent.

A hydroxyC$_{1-6}$alkyl group when substituted on an oxygen atom or a nitrogen atom preferably is a hydroxyC$_{2-6}$alkyl group wherein the hydroxy group and the oxygen or nitrogen are separated by at least two carbon atoms.

R$^6$ or R$^{6a}$ can be C$_{1-6}$alkyl substituted with one or more substituents selected from NR$^{7a}$R$^{7b}$, hydroxy, C$_{1-4}$alkoxy, C$_{1-4}$alkylthio, Ar$^2$-oxy-, Ar$^2$-thio-, Ar$^2$(CH$_2$)$_n$oxy, Ar$^2$(CH$_2$)$_n$thio, aminocarbonyloxy, C$_{1-4}$alkylcarbonyloxy, Ar$^2$carbonyloxy, Ar$^2$(CH$_2$)$_n$carbonyloxy, C$_{1-4}$alkoxycarbonyl(CH$_2$)$_n$oxy, mono- and di(C$_{1-4}$alkyl)aminocarbonyloxy. In that instance C$_{1-6}$alkyl preferably has at least two carbon atoms (i.e. C$_{2-6}$alkyl) and the said substituents are not substituted on the carbon atom linked to the nitrogen bearing Q.

As used herein C$_{1-4}$alkyl as a group or part of a group defines straight or branched chain saturated hydrocarbon radicals having from 1 to 4 carbon atoms such as methyl, ethyl, propyl, 1-methylethyl, butyl and the like; C$_{2-4}$alkyl as a group or part of a group defines straight or branched chain saturated hydrocarbon radicals having from 2 to 4 carbon atoms such as ethyl, propyl, 1-methylethyl, butyl and the like; C$_{1-6}$alkyl as a group or part of a group defines straight or branched chain saturated hydrocarbon radicals having from 1 to 6 carbon atoms such as the groups defined for C$_{1-4}$alkyl and pentyl, hexyl, 2-methylbutyl and the like.

As used herein C$_{2-6}$alkenyl as a group or part of a group defines straight or branched chain saturated hydrocarbon radicals having at least one double bond, and preferably having one double bond, and further having from 2 to 6 carbon atoms such as ethenyl, propenyl, buten-1-yl, buten-2-yl, penten-1-yl, penten-2-yl, hexen-1-yl, hexen-2-yl, hexen-3-yl, 2-methylbuten-1-yl and the like.

C$_{3-7}$cycloalkyl is generic to cyclopropyl, cyclobutyl, cyclopentyl, cyclohexyl and cycloheptyl.

C$_{2-5}$alkanediyl defines bivalent straight and branched chain saturated hydrocarbon radicals having from 2 to 5 carbon atoms such as, for example, 1,2-ethanediyl, 1,3-propanediyl, 1,4-butanediyl, 1,2-propanediyl, 2,3-butanediyl, 1,5-pentanediyl and the like, C$_{1-4}$alkanediyl defines bivalent straight and branched chain saturated hydrocarbon radicals having from 1 to 4 carbon atoms such as, for example, methylene, 1,2-ethanediyl, 1,3-propanediyl, 1,4-butanediyl and the like; C$_{1-6}$alkanediyl is meant to include C$_{1-4}$alkanediyl and the higher homologues thereof having from 5 to 6 carbon atoms such as, for example, 1,5-pentanediyl, 1,6-hexanediyl and the like; C$_{1-10}$alkanediyl is meant to include C$_{1-6}$alkanediyl and the higher homologues thereof having from 7 to 10 carbon atoms such as, for example, 1,7-heptanediyl, 1,8-octanediyl, 1,9-nonanediyl, 1,10-decanediyl and the like.

As used herein before, the term (═O) forms a carbonyl moiety when attached to a carbon atom, a sulfoxide moiety when attached to a sulfur atom and a sulfonyl moiety when two of said terms are attached to a sulfur atom. The term (═N—OH) forms a hydroxyimine moiety when attached to a carbon atom.

The term halo is generic to fluoro, chloro, bromo and iodo.

It should be noted that the radical positions on any molecular moiety used in the definitions may be anywhere on such moiety as long as it is chemically stable.

Radicals used in the definitions of the variables include all possible isomers unless otherwise indicated. For instance pyridyl includes 2-pyridyl, 3-pyridyl and 4-pyridyl; pentyl includes 1-pentyl, 2-pentyl and 3-pentyl.

When any variable occurs more than one time in any constituent, each definition is independent.

Whenever used hereinafter, the term "compounds of formula (I)", or "the present compounds" or similar term is meant to include the compounds of general formula (I), their prodrugs, N-oxides, addition salts, quaternary amines, metal complexes and stereochemically isomeric forms. An interesting subgroup of the compounds of formula (I) or any subgroup thereof are the N-oxides, salts and all the stereoisomeric forms of the compounds of formula (I).

It will be appreciated that some of the compounds of formula (I) may contain one or more centers of chirality and exist as stereochemically isomeric forms.

The term "stereochemically isomeric forms" as used hereinbefore defines all the possible compounds made up of the same atoms bonded by the same sequence of bonds but having different three-dimensional structures which are not interchangeable, which the compounds of formula (I) may possess.

Unless otherwise mentioned or indicated, the chemical designation of a compound encompasses the mixture of all possible stereochemically isomeric forms which said compound may possess. Said mixture may contain all diastereomers and/or enantiomers of the basic molecular structure of said compound. All stereochemically isomeric forms of the compounds of the present invention both in pure form or in admixture with each other are intended to be embraced within the scope of the present invention.

Pure stereoisomeric forms of the compounds and intermediates as mentioned herein are defined as isomers substantially free of other enantiomeric or diastereomeric forms of the same basic molecular structure of said compounds or intermediates. In particular, the term 'stereoisomerically pure' concerns compounds or intermediates having a stereoisomeric excess of at least 80% (i.e. minimum 90% of one isomer and maximum 10% of the other possible isomers) up to a stereoisomeric excess of 100% (i.e. 100% of one isomer and none of the other), more in particular, compounds or intermediates having a stereoisomeric excess of 90% up to 100%, even more in particular having a stereoisomeric excess of 94% up to 100% and most in particular having a stereoisomeric excess of 97% up to 100%. The terms 'enantiomerically pure' and 'diastereomerically pure' should be understood in a similar way, but then having regard to the enantiomeric excess, respectively the diastereomeric excess of the mixture in question.

Pure stereoisomeric forms of the compounds and intermediates of this invention may be obtained by the application of art-known procedures. For instance, enantiomers may be separated from each other by the selective crystallization of their diastereomeric salts with optically active acids or bases. Examples thereof are tartaric acid, dibenzoyltartaric acid, ditoluoyltartaric acid and camphosulfonic acid. Alternatively, enantiomers may be separated by chromatographic techniques using chiral stationary phases. Said pure stereochemically isomeric forms may also be derived from the corresponding pure stereochemically isomeric forms of the appropriate starting materials, provided that the reaction occurs stereospecifically. Preferably, if a specific stereoisomer is desired, said compound will be synthesized by stereospecific methods of preparation. These methods will advantageously employ enantiomerically pure starting materials.

The diastereomeric racemates of formula (I) can be obtained separately by conventional methods. Appropriate physical separation methods that may advantageously be employed are, for example, selective crystallization and chromatography, e.g. column chromatography.

For some of the compounds of formula (I), their prodrugs, N-oxides, salts, solvates, quaternary amines, or metal complexes and the intermediates used in the preparation thereof, the absolute stereochemical configuration was not experimentally determined. A person skilled in the art is able to determine the absolute configuration of such compounds using art-known methods such as, for example, X-ray diffraction.

The present invention is also intended to include all isotopes of atoms occurring on the present compounds. Isotopes include those atoms having the same atomic number but different mass numbers. By way of general example and without limitation, isotopes of hydrogen include tritium and deuterium. Isotopes of carbon include C-13 and C-14.

For therapeutic use, salts of the compounds of formula (I) are those wherein the counterion is pharmaceutically acceptable. However, salts of acids and bases which are non-pharmaceutically acceptable may also find use, for example, in the preparation or purification of a pharmaceutically acceptable compound. All salts, whether pharmaceutically acceptable or not are included within the ambit of the present invention.

The pharmaceutically acceptable acid and base addition salts as mentioned hereinabove are meant to comprise the therapeutically active non-toxic acid and base addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic (i.e. hydroxybutanedioic acid), tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The compounds of formula (I) containing an acidic proton may also be converted into their non-toxic metal or amine addition salt forms by treatment with appropriate organic and inorganic bases. Appropriate base salt forms comprise, for example, the ammonium salts, the alkali and earth alkaline metal salts, e.g. the lithium, sodium, potassium, magnesium, calcium salts and the like, salts with organic bases, e.g. the benzathine, N-methyl-D-glucamine, hydrabamine salts, and salts with amino acids such as, for example, arginine, lysine and the like.

The term addition salt as used hereinabove also comprises the solvates which the compounds of formula (I) as well as the salts thereof, are able to form. Such solvates are for example hydrates, alcoholates and the like.

The term "quaternary amine" as used hereinbefore defines the quaternary ammonium salts which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary amine has a positively charged nitrogen. Pharmaceutically acceptable counterions include chloro, bromo, iodo, trifluoroacetate and acetate. The counterion of choice can be introduced using ion exchange resins.

The N-oxide forms of the present compounds are meant to comprise the compounds of formula (I) wherein one or several nitrogen atoms are oxidized to the so-called N-oxide.

It will be appreciated that the compounds of formula (I) may have metal binding, chelating, complex forming properties and therefore may exist as metal complexes or metal chelates. Such metalated derivatives of the compounds of formula (I) are intended to be included within the scope of the present invention.

Some of the compounds of formula (I) may also exist in their tautomeric form. Such forms although not explicitly indicated in the above formula are intended to be included within the scope of the present invention.

Any subgroup of compounds of formula (I) specified herein is meant to also comprise the prodrugs, N-oxides, addition salts, quaternary amines, metal complexes and stereochemically isomeric forms of this subgroup of compounds of formula (I).

One embodiment of the present invention concerns compounds of formula (I-a):

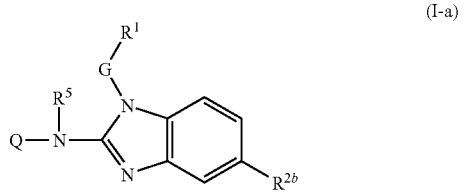

wherein Q, $R^5$, G, $R^1$ and $R^{2b}$ are as specified above in the definitions of the compounds of formula (I) or as in any of the subgroups of compounds specified herein.

Another embodiment of the present invention concerns compounds of formula (I-b):

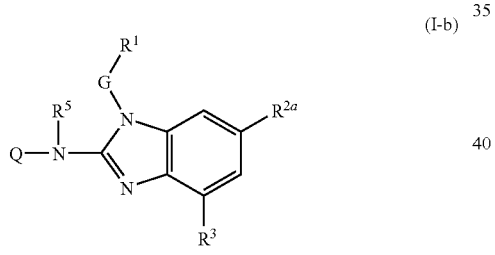

wherein Q, $R^5$, G, $R^1$, $R^{2a}$ and $R^3$ are as specified above in the definitions of the compounds of formula (I) or as in any of the subgroups of compounds specified herein.

One particular embodiment of the present invention concerns compounds of formula (I-a-1):

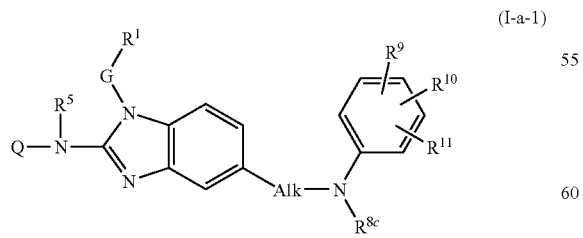

wherein Q, $R^5$, G and $R^1$ are as specified in the definitions of the compounds of formula (I) or any of the subgroups of compounds of formula (I) specified herein; and Alk is $C_{1-6}$alkanediyl;

$R^{8c}$ has the same meanings of $R^{8a}$, and also may be hydrogen;

$R^9$, $R^{10}$, $R^{11}$ independently from one another have the same meanings as the substituents on $Ar^3$ as specified in the definitions of the compounds of formula (I) or of any of the subgroups thereof.

Another particular embodiment of the present invention concerns compounds of formula (I-b-1):

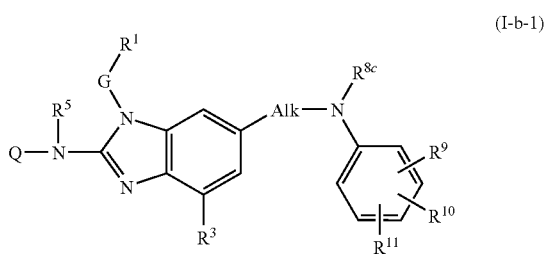

wherein Q, $R^5$, G, $R^1$ and $R^3$ are as specified in the definitions of the compounds of formula (I) or any of the subgroups of compounds of formula (I) specified herein; and Alk is $C_{1-6}$alkanediyl;

$R^{8c}$ has the same meanings of $R^{8a}$, and also may be hydrogen;

$R^9$, $R^{10}$, $R^{11}$ independently from one another have the same meanings as the substituents on $Ar^3$ as specified in the definitions of the compounds of formula (I) or of any of the subgroups thereof.

Another embodiment of the present invention concerns compounds of formula (I-c):

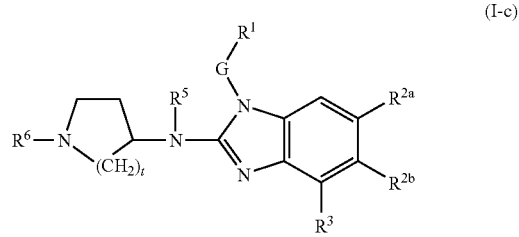

wherein t, G, $R^1$, $R^{2a}$, $R^{2b}$, $R^3$, $R^5$ and $R^6$ are as specified above in the definition of the compounds of formula (I), or as in any of the subgroups of compounds specified herein.

Another embodiment of the present invention concerns compounds of formula (I-d):

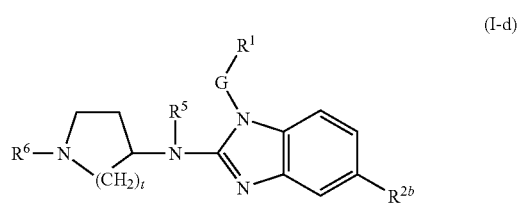

wherein t, $R^5$, $R^6$, G, $R^1$ and $R^{2b}$ are as specified above or as in any of the subgroups of compounds specified herein.

Another embodiment of the present invention concerns compounds of formula (I-e):

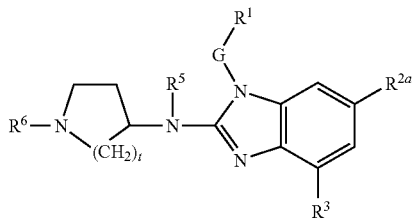

(I-e)

wherein t, $R^5$, $R^6$, G, $R^1$, $R^{2a}$ and $R^3$ are as specified above or as in any of the subgroups of compounds specified herein.

Still further embodiments comprise compounds of formula (I-c), (I-d) or (I-e) wherein t is 2, i.e. compounds of formulae

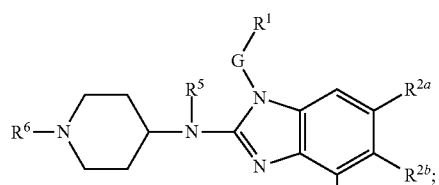

(I-c-1)

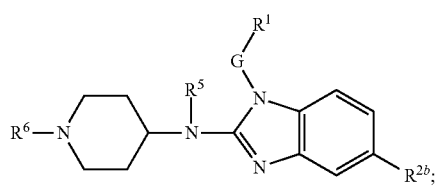

(I-d-1)

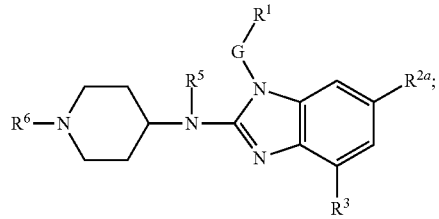

(I-e-1)

wherein Q, t, $R^5$, G, $R^1$, $R^{2a}$, $R^{2b}$, $R^3$ are as specified above or as in any of the subgroups of compounds specified herein.

Another embodiment of the present invention concerns compounds of formula (I-d-2):

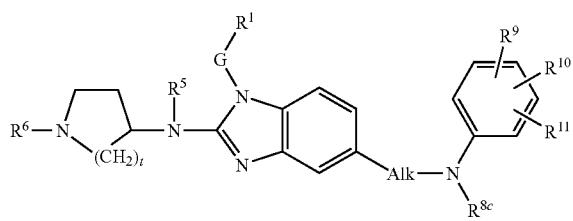

(I-d-2)

wherein $R^5$, $R^6$, G and $R^1$ are as specified above or as in any of the subgroups of compounds specified herein; and t is 1, 2 or 3; preferably t is 2;
Alk is $C_{1-6}$alkanediyl;
$R^{8c}$ has the same meanings of $R^{8a}$, and also may be hydrogen;
$R^9$, $R^{10}$, $R^{11}$ independently from one another have the same meanings as the substituents on $Ar^3$ as specified in the definitions of the compounds of formula (I) or of any of the subgroups thereof.

Another embodiment of the present invention concerns compounds of formula (I-e):

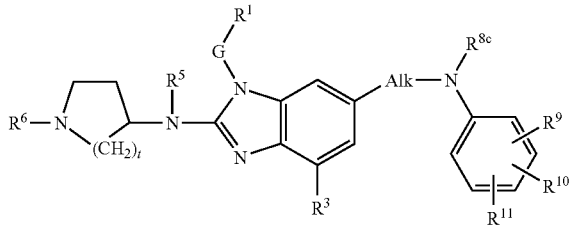

(I-e-2)

wherein $R^5$, $R^6$, G, $R^1$ and $R^3$ are as specified above or as in any of the subgroups of compounds specified herein; and
t is 1, 2 or 3; preferably t is 2;
$R^{8c}$ has the same meanings of $R^{8a}$, and also may be hydrogen;
$R^9$, $R^{10}$, $R^{11}$ independently from one another have the same meanings as the substituents on $Ar^3$ as specified in the definitions of the compounds of formula (I) or of any of the subgroups thereof.

Further preferred subgroups are those wherein Alk is ethylene or methylene, more preferably wherein Alk is methylene.

In (I-a-1), (I-b-1), (I-d-2) or (I-e-2) $R^{8c}$ preferably is hydrogen, hydroxy$C_{1-6}$alkyl, aminocarbonyl-$C_{1-6}$alkyl.

In (I-a-1), (I-b-1), (I-d-2) or (I-e-2):
(a) $R^9$, $R^{10}$, $R^{11}$ preferably and independently from one another are hydrogen, halo, hydroxy, mercapto, amino, cyano, $C_{1-6}$alkyl, $C_{2-6}$alkenyl, $C_{2-6}$alkynyl, $Ar^1$, hydroxy$C_{1-6}$alkyl, $CF_3$, amino$C_{1-6}$alkyl, cyano$C_{1-6}$alkyl, aminocarbonyl, $C_{1-6}$alkyloxy, $C_{1-6}$alkylthio, $Ar^1$-oxy, $Ar^1$-thio, $Ar^1$-amino, aminosulfonyl, aminocarbonyl-$C_{1-6}$alkyl, hydroxycarbonyl-$C_{1-6}$alkyl, hydroxycarbonyl, $C_{1-4}$alkylcarbonyl, $C_{1-4}$alkylcarbonylamino or $C_{1-4}$alkoxycarbonyl; or
(b) $R^9$, $R^{10}$, $R^{11}$ more preferably and independently from one another are hydrogen, halo, hydroxy, mercapto, cyano, $C_{1-6}$alkyl, $C_{2-6}$alkenyl, $C_{2-6}$alkynyl, $Ar^1$, hydroxy-$C_{1-6}$alkyl, $CF_3$, amino$C_{1-6}$alkyl, cyano$C_{1-6}$alkyl, aminocarbonyl, $C_{1-6}$alkyloxy, $C_{1-6}$alkylthio, $Ar^1$-oxy, $Ar^1$-thio, $Ar^1$-amino, aminosulfonyl, aminocarbonyl-$C_{1-6}$alkyl, hydroxycarbonyl-$C_{1-6}$alkyl, $C_{1-4}$alkylcarbonyl, $C_{1-4}$alkylcarbonylamino or $C_{1-4}$alkoxycarbonyl; or
(c) $R^9$, $R^{10}$, $R^{11}$ more preferably and independently from one another are halo, $C_{1-6}$alkyl or hydroxy$C_{1-6}$alkyl; or
(d) $R^9$, $R^{10}$ more preferably are as in (a), (b) or (c) and $R^{11}$ is hydrogen; or
(e) $R^9$, $R^{10}$ more preferably and independently from one another are $C_{1-6}$alkyl or hydroxy-$C_{1-6}$alkyl; and $R^{11}$ is hydrogen; or
(f) $R^9$, $R^{10}$ still more preferably are $C_{1-6}$alkyl and $R^{11}$ is hydrogen; or
(g) $R^9$ is $C_{1-6}$alkyl, $R^{10}$ is hydroxy-$C_{1-6}$alkyl and $R^{11}$ is hydrogen.

It is to be understood that the above defined subgroups of compounds of formulae (I-a), (I-b), etc. as well as any other subgroup defined herein, are meant to also comprise any prodrugs, N-oxides, addition salts, quaternary amines, metal complexes and stereochemically isomeric forms of such compounds.

Particular subgroups of the compounds of formula (I) are those compounds of formula (I), or any subgroup of compounds of formula (I) specified herein, wherein G is $C_{1-10}$alkanediyl, more in particular wherein G is methylene.

Other particular subgroups of the compounds of formula (I) are those compounds of formula (I), or any subgroup of compounds of formula (I) specified herein, wherein (a) $R^1$ is other than $Ar^1$; or wherein
(b) $R^1$ is $Ar^1$ or a monocyclic heterocycle, which is as specified in the definitions of the compounds of formula (I) or any of the subgroups thereof.

Further particular subgroups of the compounds of formula (I) are those compounds of formula (I), or any subgroup of compounds of formula (I) specified herein, wherein (c) $R^1$ is pyridyl optionally substituted with 1 or 2 substituents independently selected from the group consisting of halo, hydroxy, amino, cyano, carboxyl, $C_{1-6}$alkyl, $C_{1-6}$alkyloxy, $C_{1-6}$alkylthio, $C_{1-6}$alkyloxy$C_{1-6}$alkyl, $Ar^1$, $Ar^1C_{1-6}$alkyl, $Ar^1C_{1-6}$alkyloxy, hydroxy$C_{1-6}$alkyl, mono- or di($C_{1-6}$alkyl)amino, mono- or di($C_{1-6}$alkyl)amino$C_{1-6}$alkyl, polyhalo$C_{1-6}$alkyl, $C_{1-6}$alkylcarbonylamino, $C_{1-6}$alkyl-$SO_2$—$NR^{4a}$—, $Ar^1$—$SO_2$—$NR^{4a}$—, $C_{1-6}$alkyloxycarbonyl, —C(=O)—$NR^{4a}R^{4b}$, HO(—$CH_2$—$CH_2$—O)$_n$—, halo(—$CH_2$—$CH_2$—O)$_n$—, $C_{1-6}$alkyloxy(—$CH_2$—$CH_2$—O)$_n$—, $Ar^1C_{1-6}$alkyloxy(—$CH_2$—$CH_2$—O)$_n$— and mono- or di($C_{1-6}$alkyl)amino(—$CH_2$—$CH_2$—O)$_n$—; or more in particular
(d) $R^1$ is pyridyl substituted with 1 or 2 substituents independently selected from the group consisting of hydroxy, $C_{1-6}$alkyl, halo, $C_{1-6}$alkyloxy, $Ar^1C_{1-6}$alkyloxy and ($C_{1-6}$alkyloxy)$C_{1-6}$alkyloxy; preferably wherein
(e) $R^1$ is pyridyl substituted with 1 or 2 substituents independently selected from the group consisting of hydroxy, $C_{1-6}$alkyl, halo and $C_{1-6}$alkyloxy; or wherein
(f) $R^1$ is pyridyl substituted with 1 or 2 substituents independently selected from the group consisting of hydroxy and $C_{1-6}$alkyl; more preferably wherein
(g) $R^1$ is pyridyl substituted with hydroxy and $C_{1-6}$alkyl; or more preferably wherein
(h) $R^1$ is pyridyl substituted with hydroxy and methyl; or wherein
(i) $R^1$ is 3-hydroxy-6-methylpyrid-2-yl.

Further embodiments comprise those compounds of formula (I) or any of the subgroups of compounds of formula (I) wherein (j) $R^1$ is $Ar^1$, quinolinyl, benzimidazolyl, a radical of formula

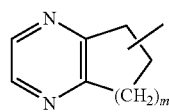

(c-4)

pyrazinyl, or pyridyl; or wherein
(k) $R^1$ is $Ar^1$, quinolinyl, benzimidazolyl or a radical of formula (c-4) wherein m is 2, pyrazinyl or pyridyl;

wherein each of the radicals in (j) and (k) may optionally be substituted with the substituents specified in the definition of the compounds of formula (I) and in particular pyridyl may be substituted as specified above in (a) to (i); or more specifically wherein (l) $R^1$ is $Ar^1$, quinolinyl, benzimidazolyl or a radical of formula (c-4) wherein m is 2, pyrazinyl or pyridyl, wherein each of these radicals may optionally be substituted with one, two or three radicals selected from the group consisting of halo, hydroxy, $C_{1-6}$alkyl, $C_{1-6}$alkyloxy, $Ar^1C_{1-6}$alkyloxy, ($C_{1-6}$alkyloxy)$C_{1-6}$alkyloxy; or more specifically wherein (m) $R^1$ is $Ar^1$, quinolinyl, benzimidazolyl or a radical of formula (c-4) wherein m is 2, pyrazinyl or pyridyl, wherein each of these radicals may optionally be substituted with one, two or three radicals selected from the group consisting of halo, hydroxy, $C_{1-6}$alkyl, $C_{1-6}$alkyloxy, benzyloxy; or more specifically wherein (n) $R^1$ is phenyl optionally substituted with one, two or three radicals selected from the group consisting of halo, hydroxy, $C_{1-6}$alkyl, $C_{1-6}$alkyloxy; quinolinyl; a radical (c-4) wherein m is 2, optionally substituted with up to two radicals selected from $C_{1-6}$alkyl; benzimidazolyl optionally substituted with $C_{1-6}$alkyl; pyridyl optionally substituted with one or two radicals selected from hydroxy, halo, $C_{1-6}$alkyl, benzyloxy and $C_{1-6}$alkyloxy, pyrazinyl optionally substituted with up to three radicals selected from $C_{1-6}$alkyl; or pyridyl substituted or optionally substituted as specified above in (a)-(i); or wherein (o) $R^1$ is phenyl optionally substituted with one or two radicals selected from the group consisting of halo, hydroxy, $C_{1-6}$alkyl, $C_{1-6}$alkyloxy;
(p) $R^1$ is quinolinyl;
(q) $R^1$ is a radical (c-4) wherein m is 2, optionally substituted with up to two radicals selected from $C_{1-6}$alkyl;
(r) $R^1$ is benzimidazolyl optionally substituted with $C_{1-6}$alkyl; pyridyl optionally substituted with one or two radicals selected from hydroxy, halo, $C_{1-6}$alkyl, benzyloxy and $C_{1-6}$alkyloxy,
(s) $R^1$ is pyrazinyl optionally substituted with up to three radicals selected from $C_{1-6}$alkyl.

Preferred subgroups of compounds of formula (I) or any of the subgroups of compounds of formula (I) are those wherein G is a direct bond or methylene and $R^1$ is as specified above in (a)-(s). Further preferred are the compounds of formula (I) or any of the subgroups specified herein wherein G is a direct bond and $R^1$ is a radical (c-4), in particular wherein m is 2, optionally substituted with up to two radicals selected from $C_{1-6}$alkyl. Further preferred are the compounds of formula (I) or any of the subgroups specified herein wherein or G is methylene and $R^1$ is as specified above in (a)-(s), but is other than a radical (c-4).

A particular embodiment of the present invention concerns compounds of formula (I) or of any of the subgroups of compounds of formula (I) specified herein wherein (a) one of $R^{2a}$ and $R^{3a}$ is selected from cyano$C_{1-6}$alkyl, cyano$C_{2-6}$alkenyl, $Ar^3C_{1-6}$alkyl, ($Ar^3$)(OH)$C_{1-6}$alkyl, Het-$C_{1-6}$alkyl, N($R^{8a}R^{8b}$)$C_{1-6}$alkyl, $Ar^3C_{2-6}$alkenyl, Het-$C_{2-6}$alkenyl, $Ar^3$amino$C_{1-6}$alkyl, Het-amino$C_{1-6}$alkyl, Het-$C_{1-6}$alkylamino-$C_{1-6}$alkyl, $Ar^3$thio$C_{1-6}$alkyl, Het-thio$C_{1-6}$alkyl, $Ar^3$sulfonyl$C_{1-6}$alkyl, Het-sulfonyl-$C_{1-6}$alkyl, $Ar^3$aminocarbonyl, Het-aminocarbonyl, $Ar^3$(CH$_2$)$_n$aminocarbonyl, Het-(CH$_2$)$_n$aminocarbonyl, $Ar^3$carbonylamino, $Ar^3$(CH$_2$)$_n$amino; and the other one of $R^{2a}$ and $R^{2b}$ is hydrogen; or (b) one of $R^{2a}$ and $R^{3a}$ is selected from cyano$C_{1-6}$alkyl, cyano$C_{2-6}$alkenyl, $Ar^3C_{1-6}$alkyl, ($Ar^3$)(OH)$C_{1-6}$alkyl, Het-$C_{1-6}$alkyl, N($R^{8a}R^{8b}$)$C_{1-6}$alkyl, $Ar^3C_{2-6}$alkenyl, $Ar^3$amino$C_{1-6}$alkyl, Het-amino$C_{1-6}$alkyl, Het-$C_{1-6}$alkylamino$C_{1-6}$alkyl, $Ar^3$thio-$C_{1-6}$alkyl, $Ar^3$aminocarbonyl, Het-aminocarbonyl, $Ar^3$(CH$_2$)$_n$aminocarbonyl, Het-(CH$_2$)

$_n$aminocarbonyl, Ar$^3$carbonylamino, Ar$^3$(CH$_2$)$_n$amino; and the other one of R$^{2a}$ and R$^{2b}$ is hydrogen; or (c) one of R$^{2a}$ and R$^{3a}$ is selected from cyanoC$_{1-6}$alkyl, Ar$^3$C$_{1-6}$alkyl, Het-C$_{1-6}$alkyl, N(R$^{8a}$R$^{8b}$)C$_{1-6}$alkyl, Ar$^3$C$_{2-6}$alkenyl, Ar$^3$aminoC$_{1-6}$alkyl, Het-aminoC$_{1-6}$alkyl, Het-C$_{1-6}$alkylaminoC$_{1-6}$alkyl, Ar$^3$thioC$_{1-6}$alkyl, Ar$^3$aminocarbonyl, Het-aminocarbonyl, Ar$^3$(CH$_2$)$_n$aminocarbonyl, Het-(CH$_2$)$_n$aminocarbonyl; and the other one of R$^{2a}$ and R$^{2b}$ is hydrogen; or (d) one of R$^{2a}$ and R$^{3a}$ is selected from cyanoC$_{1-6}$alkyl, Ar$^3$C$_{1-6}$alkyl, Het-C$_{1-6}$alkyl, N(R$^{8a}$R$^{8b}$)C$_{1-6}$alkyl, Ar$^3$C$_{2-6}$alkenyl, Ar$^3$aminoC$_{1-6}$alkyl, Het-aminoC$_{1-6}$alkyl, Ar$^3$aminocarbonyl; and the other one of R$^{2a}$ and R$^{2b}$ is hydrogen; or (e) one of R$^{2a}$ and R$^{3a}$ is selected from Ar$^3$C$_{1-6}$alkyl, N(R$^{8a}$R$^{8b}$)C$_{1-6}$alkyl, Ar$^3$C$_{2-6}$alkenyl, Ar$^3$aminoC$_{1-6}$alkyl; and the other one of R$^{2a}$ and R$^{2b}$ is hydrogen; or (f) one of R$^{2a}$ and R$^{3a}$ is selected from N(R$^{8a}$R$^{8b}$)C$_{1-6}$alkyl, Ar$^3$aminoC$_{1-6}$alkyl; and the other one of R$^{2a}$ and R$^{2b}$ is hydrogen;

and for any of (a)-(f)
in case R$^{2a}$ is hydrogen then R$^3$ is hydrogen;
in case R$^{2b}$ is hydrogen then R$^3$ is hydrogen or C$_{1-6}$alkyl; or preferably then R$^3$ is hydrogen.

Further particular subgroups of the compounds of formula (I) are those compounds of formula (I), or any subgroup of compounds of formula (I) specified herein, wherein R$^5$ is hydrogen.

Other particular subgroups of the compounds of formula (I) are those compounds of formula (I), or any subgroup of compounds of formula (I) specified herein, wherein Q is Ar$^2$.

Other particular subgroups of the compounds of formula (I) are those compounds of formula (I), or any subgroup of compounds of formula (I) specified herein, wherein Q is R$^{6a}$.

Other particular subgroups of the compounds of formula (I) are those compounds of formula (I), or any subgroup of compounds of formula (I) specified herein, wherein Q is pyrrolidinyl substituted with R$^6$, piperidinyl substituted with R$^6$ or homopiperidinyl substituted with R$^6$; in particular wherein Q is piperidinyl substituted with R$^6$. Preferably the R$^6$ group is substituted on the nitrogen atom of the said pyrrolidinyl, piperidinyl or homopiperidinyl. More preferably the said pyrrolidinyl, piperidinyl or homopiperidinyl is linked to the —N(R$^5$)— moiety via a 3-yl or in particular via a 4-yl link.

Interesting subgroups of compounds are those compounds of formula (I) or of any of the subgroups specified herein, wherein Q is R$^6$, wherein (a) R$^{6a}$ is C$_{1-6}$alkyl substituted with two substituents or, preferably, with one substituent, each independently selected from the group consisting of trifluoromethyl, NR$^{7a}$R$^{7b}$, Ar$^2$, hydroxy, C$_{1-4}$alkoxy, Ar$^2$(CH$_2$)$_n$oxy, hydroxycarbonyl, aminocarbonyl, C$_{1-4}$alkylcarbonyl, C$_{1-4}$alkoxycarbonyl, Ar$^2$(CH$_2$)$_n$carbonyl, aminocarbonyloxy, C$_{1-4}$alkylcarbonyloxy, Ar$^2$carbonyloxy, mono- or di(C$_{1-4}$alkyl)aminocarbonyl, aminosulfonyl, mono- or di(C$_{1-4}$alkyl)aminosulfonyl or a heterocycle selected from the group consisting of pyrrolidinyl, imidazolyl, piperidinyl, homopiperidinyl, piperazinyl, dioxolanyl, dioxanyl and pyridyl, wherein each of said heterocycle may optionally be substituted with one or two radicals selected from oxo and C$_{1-6}$alkyl; or in particular wherein (b) R$^{6a}$ is C$_{1-6}$alkyl substituted with one substituent and, optionally with a further substituent which is hydroxy, wherein said substituent is trifluoromethyl, NR$^{7a}$R$^{7b}$, Ar$^2$, hydroxy, C$_{1-4}$alkoxy, Ar$^2$(CH$_2$)$_n$oxy, hydroxycarbonyl, aminocarbonyl, C$_{1-4}$alkylcarbonyl, C$_{1-4}$alkoxycarbonyl, Ar$^2$(CH$_2$)$_n$carbonyl, aminocarbonyloxy, C$_{1-4}$alkylcarbonyloxy, Ar$^2$carbonyloxy, mono- or di(C$_{1-4}$alkyl)aminocarbonyl, aminosulfonyl, mono- or di(C$_{1-4}$alkyl)aminosulfonyl or a heterocycle selected from the group consisting of pyrrolidinyl, imidazolyl, piperidinyl, homopiperidinyl, piperazinyl, dioxolanyl, dioxanyl and pyridyl, wherein each of said heterocycle may optionally be substituted with one or two radicals selected from oxo and C$_{1-6}$alkyl; or further in particular (c) R$^{6a}$ is C$_{1-6}$alkyl substituted with NR$^{7a}$R$^{7b}$, Ar$^2$, hydroxy, C$_{1-4}$alkoxy, hydroxycarbonyl, aminocarbonyl, aminosulfonyl C$_{1-4}$alkylcarbonyl, Ar$^2$carbonyl, C$_{1-4}$alkoxycarbonyl, or C$_{1-6}$alkyl substituted with two hydroxy radicals, or C$_{1-6}$alkyl substituted with a heterocycle selected from dioxolanyl, pyrrolidinyl, piperidinyl, homopiperidinyl, piperazinyl, wherein each of said heterocycle may optionally be substituted with oxo or with one or two C$_{1-6}$alkyl radicals; or further in particular (d) R$^{6a}$ is C$_{1-6}$alkyl substituted with NR$^{7a}$R$^{7b}$, Ar$^2$, hydroxy, hydroxycarbonyl, aminocarbonyl, aminosulfonyl or C$_{1-6}$alkyl substituted with two hydroxy radicals, or C$_{1-6}$alkyl substituted with a heterocycle selected from dioxolanyl, pyrrolidinyl, piperidinyl, homopiperidinyl, piperazinyl, wherein each of said heterocycle may optionally be substituted with oxo or with one or two C$_{1-6}$alkyl radicals; or further in particular (e) R$^{6a}$ is C$_{1-6}$alkyl substituted with Ar$^2$ or hydroxy, or C$_{1-6}$alkyl substituted with two hydroxy radicals, or C$_{1-6}$alkyl substituted with a heterocycle selected from dioxolanyl, pyrrolidinyl, piperidinyl, piperazinyl, wherein each of said heterocycle may optionally be substituted with one or two C$_{1-6}$alkyl radicals; or preferably (f) R$^{6a}$ is C$_{1-6}$alkyl substituted with Ar$^2$ or hydroxy, or C$_{1-6}$alkyl substituted with two hydroxy radicals, or C$_{1-6}$alkyl substituted with diC$_{1-6}$alkyl-dioxolanyl, pyrrolidinyl, piperidinyl, piperazinyl, 4-C$_{1-6}$alkyl-piperazinyl; or preferably (g) R$^{6a}$ is C$_{1-6}$alkyl substituted with Ar$^2$ or hydroxy, or C$_{1-6}$alkyl substituted with two hydroxy radicals, or C$_{1-6}$alkyl substituted with piperidinyl or with piperazinyl; or more preferably (h) R$^{6a}$ is C$_{1-6}$alkyl substituted with Ar$^2$ or C$_{1-6}$alkyl substituted with piperidinyl or with piperazinyl.

Preferably in (a)-(h) in the previous paragraph the radicals pyrrolidinyl, piperidinyl, homopiperidinyl or piperazinyl are linked by their nitrogen atom to the C$_{1-6}$alkyl on which they are substituted.

Other particular subgroups of the compounds of formula (I) are those compounds of formula (I), or any subgroup of compounds of formula (I) specified herein, wherein Q is pyrrolidinyl substituted with R$^6$, piperidinyl substituted with R$^6$ or homopiperidinyl substituted with R$^6$; wherein (a) R$^6$ is hydrogen or C$_{1-6}$alkyl optionally substituted with two substituents or, preferably, with one substituent, each independently selected from the group consisting of trifluoromethyl, NR$^{7a}$R$^{7b}$, Ar$^2$, hydroxy, C$_{1-4}$alkoxy, Ar$^2$(CH$_2$)$_n$oxy, hydroxycarbonyl, aminocarbonyl, C$_{1-4}$alkylcarbonyl, C$_{1-4}$alkoxycarbonyl, Ar$^2$(CH$_2$)$_n$carbonyl, aminocarbonyloxy, C$_{1-4}$alkylcarbonyloxy, Ar$^2$carbonyloxy, mono- or di(C$_{1-4}$alkyl)aminocarbonyl, aminosulfonyl, mono- or di(C$_{1-4}$alkyl)aminosulfonyl or a heterocycle selected from the group consisting of pyrrolidinyl, imidazolyl, piperidinyl, homopiperidinyl, piperazinyl, dioxolanyl, dioxanyl and pyridyl, wherein each of said heterocycle may optionally be substituted with one or two radicals selected from oxo and C$_{1-6}$alkyl; or in particular (b) $R^6$ is hydrogen or $C_{1-6}$alkyl optionally substituted with one substituent and, optionally with a further substituent which is hydroxy, wherein said substituent is trifluoromethyl, $NR^{7a}R^{7b}$, $Ar^2$, hydroxy, $C_{1-4}$alkoxy, $Ar^2(CH_2)_n$oxy, hydroxycarbonyl, aminocarbonyl, $C_{1-4}$alkylcarbonyl, $C_{1-4}$alkoxycarbonyl, $Ar^2(CH_2)_n$-carbonyl, aminocarbonyloxy, $C_{1-4}$alkylcarbonyloxy, $Ar^2$carbonyloxy, mono- or di($C_{1-4}$alkyl)aminocarbonyl, aminosulfonyl, mono- or di($C_{1-4}$alkyl)aminosulfonyl or a heterocycle selected from the group consisting of pyrrolidinyl, imidazolyl, piperidinyl, homopiperidinyl, piperazinyl, dioxolanyl, dioxanyl and pyridyl, wherein each of said heterocycle may optionally be substituted with one or two radicals selected from oxo and $C_{1-6}$alkyl; or further in particular (c) $R^6$ is hydrogen or $C_{1-6}$alkyl optionally substituted with $NR^{7a}R^{7b}$, $Ar^2$, hydroxy, $C_{1-4}$alkoxy, hydroxycarbonyl, aminocarbonyl, aminosulfonyl, $C_{1-4}$alkoxycarbonyl or $C_{1-6}$alkyl substituted with two hydroxy radicals, or $C_{1-6}$alkyl substituted with a heterocycle selected from dioxolanyl, pyrrolidinyl, piperidinyl, homopiperidinyl, piperazinyl, wherein each of said heterocycle may optionally be substituted with oxo or with one or two $C_{1-6}$alkyl radicals; or further in particular (d) $R^6$ is hydrogen or $C_{1-6}$alkyl optionally substituted with $NR^{7a}R^{7b}$, $Ar^2$, hydroxy, hydroxycarbonyl, aminocarbonyl, aminosulfonyl or $C_{1-6}$alkyl substituted with two hydroxy radicals, or $C_{1-6}$alkyl substituted with a heterocycle selected from dioxolanyl, pyrrolidinyl, piperidinyl, homopiperidinyl, piperazinyl, wherein each of said heterocycle may optionally be substituted with oxo or with one or two $C_{1-6}$alkyl radicals; or further in particular wherein (e) $R^6$ is hydrogen or $C_{1-6}$alkyl optionally substituted with $Ar^2$, hydroxy, aminocarbonyl or aminosulfonyl, or $C_{1-6}$alkyl substituted with two hydroxy radicals, or $C_{1-6}$alkyl substituted with a heterocycle selected from dioxolanyl, pyrrolidinyl, piperidinyl, piperazinyl, wherein each of said heterocycle may optionally be substituted with one or two $C_{1-6}$alkyl radicals; or preferably (f) $R^6$ is hydrogen or $C_{1-6}$alkyl optionally substituted with $Ar^2$, hydroxy, aminocarbonyl, aminosulfonyl, or $C_{1-6}$alkyl substituted with two hydroxy radicals, or $C_{1-6}$alkyl substituted with pyrrolidinyl, piperidinyl, piperazinyl, 4-$C_{1-6}$alkylpiperazinyl; or preferably (g) $R^6$ is hydrogen or $C_{1-6}$alkyl optionally substituted with $Ar^2$, hydroxy, aminocarbonyl or aminosulfonyl; or preferably (h) $R^6$ is hydrogen or $C_{1-6}$alkyl substituted with $Ar^2$ or $C_{1-6}$alkyl substituted with piperidinyl or with piperazinyl; or (i) $R^6$ is $C_{1-6}$alkyl.

Preferably in (a)-(h) in the previous paragraph, the radicals pyrrolidinyl, piperidinyl, homopiperidinyl or piperazinyl are linked by their nitrogen atom to the $C_{1-6}$alkyl on which they are substituted.

Further particular subgroups of the compounds of formula (I) are those compounds of formula (I), or any subgroup of compounds of formula (I) specified herein, wherein $R^{7a}$ and $R^{7b}$ are hydrogen or $C_{1-6}$alkyl, or preferably wherein $R^{7a}$ and $R^{7b}$ are hydrogen.

Further particular subgroups of the compounds of formula (I) are those compounds of formula (I), or any subgroup of compounds of formula (I) specified herein, wherein (a) $R^{8a}$ is $Ar^3$, $C_{1-6}$alkyl, hydroxy$C_{1-6}$alkyl, $C_{1-6}$alkoxy$C_{1-6}$alkyl, cyano$C_{1-6}$alkyl, amino$C_{1-6}$alkyl, mono- or di($C_{1-6}$alkyl)amino$C_{1-6}$alkyl, $Ar^3C_{1-6}$alkyl, Het-$C_{1-6}$alkyl, aminocarbonyl-$C_{1-6}$-alkyl, carboxyl-$C_{1-6}$-alkyl; and $R^{8b}$ is $Ar^3$; or (b) $R^{8a}$ is $Ar^3$, $C_{1-6}$alkyl, hydroxy$C_{1-6}$alkyl, $Ar^3C_{1-6}$alkyl, Het-$C_{1-6}$alkyl, aminocarbonyl-$C_{1-6}$-alkyl; and $R^{8b}$ is $Ar^3$; or (c) $R^{8a}$ is hydroxy$C_{1-6}$alkyl, aminocarbonyl-$C_{1-6}$-alkyl; and $R^{8b}$ is $Ar^3$; or (d) $R^{8a}$ is $Ar^3$ and $R^{8b}$ is $Ar^3$; or (e) $R^{8a}$ is $C_{1-6}$alkyl, hydroxy$C_{1-6}$alkyl, $Ar^3C_{1-6}$alkyl, Het-$C_{1-6}$alkyl, aminocarbonyl$C_{1-6}$-alkyl; and $R^{8b}$ is $C_{1-6}$alkyl, hydroxy$C_{1-6}$alkyl, $Ar^3C_{1-6}$alkyl, Het-$C_{1-6}$alkyl.

In particular, $Ar^1$ is phenyl or phenyl substituted with 1, 2, 3 substituents or with 1, 2 substituents selected from those mentioned in the definition of the compounds of formula (I) or of any subgroup thereof.

In the group of compounds of formula (I) or in any of the subgroups of compounds of formula (I):

(a) $Ar^1$ preferably is phenyl or phenyl substituted with up to 3 substituents, or with up to 2 substituents, or with one substituent, selected from halo, hydroxy, $C_{1-6}$alkyl, hydroxy$C_{1-6}$alkyl, trifluormethyl, and $C_{1-6}$alkyloxy;

(b) $Ar^1$ more preferably is phenyl or phenyl substituted with up to 3 substituents, or with up to 2 substituents, or with one substituent, selected from halo, hydroxy, $C_{1-6}$alkyl and $C_{1-6}$alkyloxy;

(c) $Ar^1$ more preferably is phenyl or phenyl substituted with up to 3 substituents, or with up to 2 substituents, or with one substituent, selected from halo and $C_{1-6}$alkyl.

In particular, $Ar^2$ is phenyl or phenyl substituted with 1, 2, 3 substituents or with 1, 2 substituents selected from the group consisting of those mentioned in the definition of the compounds of formula (I) or of any subgroup thereof.

Further particular subgroups of the compounds of formula (I) are those compounds of formula (I), or any subgroup of compounds of formula (I) specified herein, wherein $Ar^2$ is as defined for $Ar^1$.

Further particular subgroups of the compounds of formula (I) are those compounds of formula (I), or any subgroup of compounds of formula (I) specified herein, wherein $Ar^3$ is phenyl, naphthalenyl, 1,2,3,4-tetrahydro-naphthalenyl or indanyl, or preferably wherein $Ar^3$ is phenyl, naphthalenyl or indanyl; wherein said phenyl may optionally and each individually be substituted with one or more, such as 2, 3 or 4, substituents selected from the group consisting of substituents of $Ar^3$ in the definitions of the compounds (I).

Further particular subgroups of the compounds of formula (I) are those compounds of formula (I), or any subgroup of compounds of formula (I) specified herein, wherein (a) $Ar^3$ is phenyl optionally substituted with one, two or three substituents selected from halo, hydroxy, mercapto, amino, cyano, $C_{1-6}$alkyl, $C_{2-6}$alkenyl, $C_{2-6}$alkynyl, $Ar^1$, hydroxy$C_{1-6}$alkyl, $CF_3$, amino$C_{1-6}$alkyl, cyano$C_{1-6}$alkyl, aminocarbonyl, $C_{1-6}$alkyloxy, $C_{1-6}$alkylthio, $Ar^1$-oxy, $Ar^1$-thio, $Ar^1$-amino, aminosulfonyl, aminocarbonyl-$C_{1-6}$alkyl, hydroxycarbonyl-$C_{1-6}$alkyl, hydroxycarbonyl, $C_{1-4}$alkylcarbonyl, $C_{1-4}$alkylcarbonylamino or $C_{1-4}$alkoxycarbonyl; or wherein (b) $Ar^3$ is phenyl optionally substituted with one, two or three substituents selected from halo, hydroxy, mercapto, cyano, $C_{1-6}$alkyl, $C_{2-6}$alkenyl, $C_{2-6}$alkynyl, $Ar^1$, hydroxy$C_{1-6}$alkyl, $CF_3$, amino$C_{1-6}$alkyl, cyano$C_{1-6}$alkyl, aminocarbonyl, $C_{1-6}$alkyloxy, $C_{1-6}$alkylthio, $Ar^1$-oxy, $Ar^1$-thio, $Ar^1$-amino, aminosulfonyl, aminocarbonyl-$C_{1-6}$alkyl, hydroxycarbonyl-$C_{1-6}$alkyl, $C_{1-4}$alkylcarbonyl, $C_{1-4}$alkylcarbonylamino or $C_{1-4}$alkoxycarbonyl; or wherein (c) $Ar^3$ is phenyl optionally substituted with one, two or three substituents selected from halo, $C_{1-6}$alkyl or hydroxy$C_{1-6}$alkyl; or (d) Ar³ is phenyl substituted with one, two or three substituents selected from halo, $C_{1-6}$alkyl or hydroxy$C_{1-6}$alkyl; or
(e) Ar³ is phenyl optionally substituted with one, two or three substituents selected from halo, $C_{1-6}$alkyl or hydroxy$C_{1-6}$alkyl; or
(f) Ar³ is phenyl substituted with one, two or three substituents selected from halo, $C_{1-6}$alkyl or hydroxy$C_{1-6}$alkyl; or
(g) Ar³ is phenyl substituted with one or two substituents selected from halo, $C_{1-6}$alkyl or hydroxy$C_{1-6}$alkyl; or
(h) Ar³ is phenyl optionally substituted with one or two substituents selected from $C_{1-6}$alkyl or hydroxy$C_{1-6}$alkyl.

In particular Ar³ is as defined for Ar², more in particular Ar³ is as defined for Ar¹.

Further particular subgroups of the compounds of formula (I) are those compounds of formula (I), or any subgroup of compounds of formula (I) specified herein, wherein
(a) Het is tetrahydrofuranyl, furanyl, thienyl, thiazolyl, oxazolyl, imidazolyl, isothiazolyl, pyrazolyl, isoxazolyl, piperidinyl, homopiperidinyl, piperazinyl, morpholinyl, pyridyl, pyrazinyl, pyrimidinyl, tetrahydroquinolinyl, quinolinyl, isoquinolinyl, benzodioxanyl, benzodioxolyl, indolinyl, indolyl, which may optionally be substituted with oxo, amino, Ar¹, $C_{1-4}$alkyl, amino$C_{1-4}$alkyl, hydroxy$C_{1-6}$alkyl, Ar¹$C_{1-4}$alkyl, mono- or di($C_{1-6}$alkyl)amino$C_{1-6}$alkyl, mono- or di($C_{1-6}$alkyl)amino, (hydroxy$C_{1-6}$alkyl)amino, and optionally further with one or two $C_{1-4}$alkyl radicals; or
(b) Het is tetrahydrofuranyl, furanyl, thienyl, thiazolyl, oxazolyl, imidazolyl, pyrazolyl, isoxazolyl, piperidinyl, homopiperidinyl, piperazinyl, morpholinyl, pyridyl, pyrazinyl, pyrimidinyl, tetrahydroquinolinyl, quinolinyl, isoquinolinyl, benzodioxanyl, benzodioxolyl, indolinyl, indolyl, which may optionally be substituted with oxo, amino, Ar¹, $C_{1-4}$alkyl, amino$C_{1-4}$alkyl, hydroxy$C_{1-6}$alkyl, and optionally further with one or two $C_{1-4}$alkyl radicals; or
(c) Het is furanyl, thienyl, imidazolyl, pyrazolyl, isoxazolyl, morpholinyl, pyrimidinyl, benzodioxolyl, quinolinyl, indolinyl, which may optionally be substituted with hydroxy$C_{1-6}$alkyl or with one or two $C_{1-4}$alkyl radicals; or
(d) Het is furanyl, thienyl, imidazolyl, pyrazolyl, isoxazolyl, morpholinyl, pyrimidinyl, benzodioxolyl, quinolinyl, indolinyl, which may optionally be substituted with hydroxy$C_{1-6}$alkyl or with one or two $C_{1-4}$alkyl radicals; or
(e) Het is furanyl, imidazolyl, morpholinyl, benzodioxolyl, quinolinyl, indolinyl, which may optionally be substituted with hydroxy$C_{1-6}$alkyl or with one or two $C_{1-4}$alkyl radicals; or
(f) Het is morpholinyl, which may optionally be substituted with one or two $C_{1-4}$alkyl radicals; or
(g) Het is morpholinyl.

Preferred compounds are those compounds listed in tables 1 through 5, more in particular the compound numbers 1 to 77, 138, 143 to 165 and 171 to 177.

The compounds of formula (I) or any of the subgroups thereof can be prepared as in the following reaction schemes.

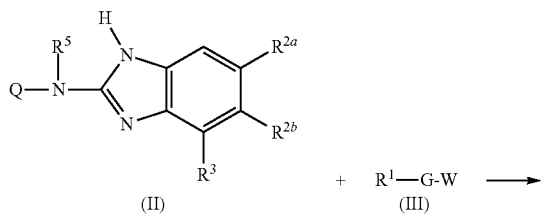

(II)     +     R¹—G-W     →
              (III)

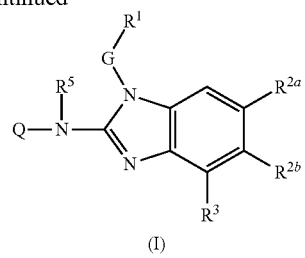

(I)

In this schemes Q, G, R¹, R²ᵃ, R²ᵇ, R³ᵃ, R³ᵇ R⁵ have the meanings defined above for the compounds of formula (I) or of any of the subgroups thereof. W is an appropriate leaving group, preferably it is chloro or bromo. The reaction of this scheme is typically conducted in a suitable solvent such as an ether, e.g. THF, a halogenated hydrocarbon, e.g. dichloromethane, CHCl₃, toluene, a polar aprotic solvent such as DMF, DMSO, DMA and the like.

The compounds of formula (I) wherein Q is a pyrrolinyl, piperidinyl or homopiperidinyl group substituted with R⁶ which is other than hydrogen, i.e. R⁶ᵃ, which are represented by formula (I-c-1), can be prepared as in the following reaction scheme.

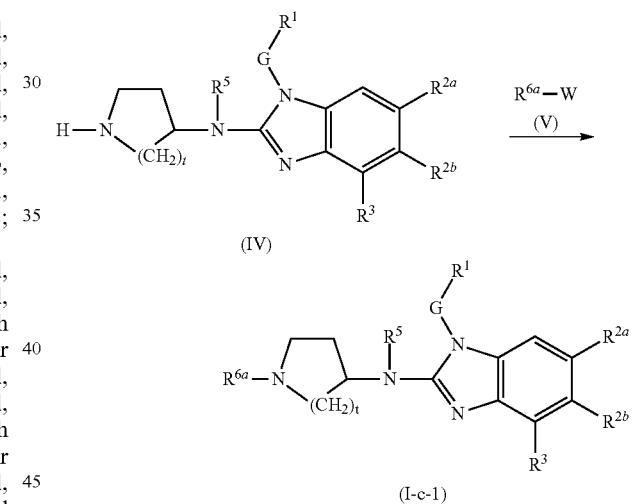

In this scheme G, t, R¹, R²ᵃ, R²ᵇ, R³, R⁵ have the meanings defined above for the compounds of formula (I) or of any of the subgroups thereof. W is an appropriate leaving group, preferably it is chloro or bromo. The reaction of this scheme can be conducted in a suitable solvent such as an ether, e.g. THF, a halogenated hydrocarbon, e.g. dichloromethane, CHCl₃, toluene, a polar aprotic solvent such as DMF, DMSO, DMA and the like. A base may be added to pick up the acid that is liberated during the reaction. If desired, certain catalysts such as iodide salts (e.g. KI) may be added. Intermediates (IV) can also be converted to compounds (I-c-1) with a reductive N-alkylation reaction starting from an aldehyde or ketone R⁶ᵇ=O (V-a), wherein R⁶ᵃ has the same meaning as R⁶ᵃ provided that it has one hydrogen atom less. This reductive alkylation is done in a suitable solvent, e.g. an alcohol, using hydrogen in the presence of a metal catalyst such as Pd or NaBH₃CN.

Some of the compounds of formula (I) can also be prepared starting from precursors of the compounds of formula (I) using appropriate functional group transformation reactions.

Precursors of the compounds of formula (I) for example are those wherein $R^{2a}$ or $R^{2b}$ is $C_{1-6}$alkoxycarbonyl or $C_{1-6}$alkyl substituted with $C_{1-6}$alkoxycarbonyl, which can be reduced, e.g. with LiAlH$_4$, to the corresponding compounds of formula (I) wherein $R^{2a}$ or $R^{2b}$ is hydroxyC$_{1-6}$alkyl. The latter group can be oxidized with a mild oxidant to an aldehyde group, e.g. with MnO$_2$, which can further be derivatized with amines, e.g. with a reductive amination process, to the corresponding mono(derivatizedC$_{1-6}$alkyl)-amines. The latter can be alkylated or arylated to alkylamines wherein $R^{2a}$ or $R^{2b}$ has formula -Alk-NR$^{8a}$R$^{8b}$. Alternatively precursors of the compounds of formula (I) wherein $R^{2a}$ or $R^{2b}$ is hydroxyC$_{1-6}$alkyl can be converted to the corresponding haloC$_{1-6}$alkyl compounds, e.g. by treatment with a suitable halogenating agent such as SOCl$_2$, which compounds subsequently are reacted with an amine or amine derivative. This reaction sequence is illustrated by the following schemes in which R$^{12}$ represents a C$_{1-6}$alkyl radical, which preferably is methyl or ethyl. This reaction sequence may be done starting from (VII-a) or (VII-b) separately but also can be done using a mixture of (VII-a) and (VII-b) and subsequently separating the reaction products either at the end of the reaction sequence or in an intermediate step.

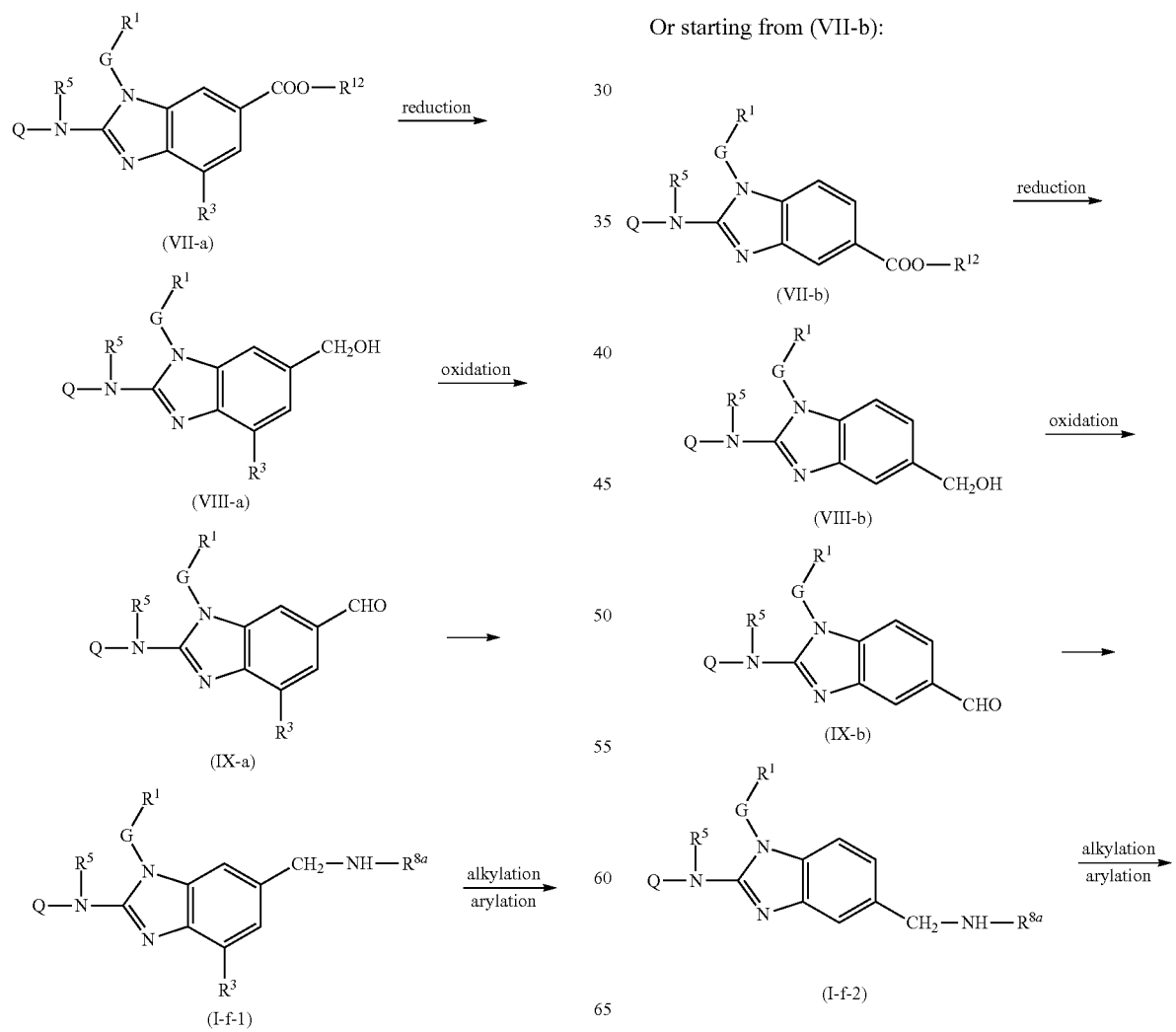

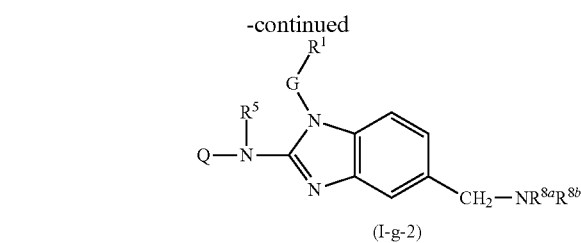

(I-g-2)

(VIII-b) →[1-conversion to leaving group; 2-N-alkylation or arylation]

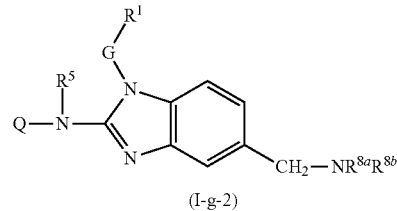

(I-g-2)

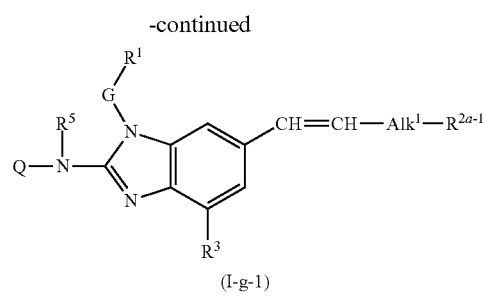

(I-g-1)

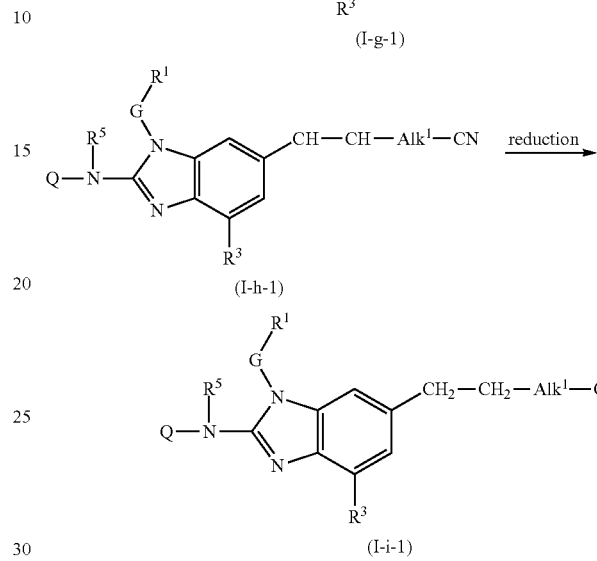

(I-h-1)

(I-i-1)

(I-h-1)

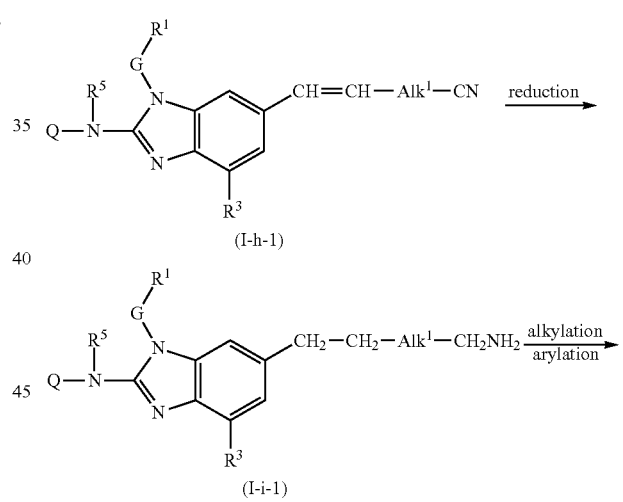

(I-i-1)

(I-k-1)

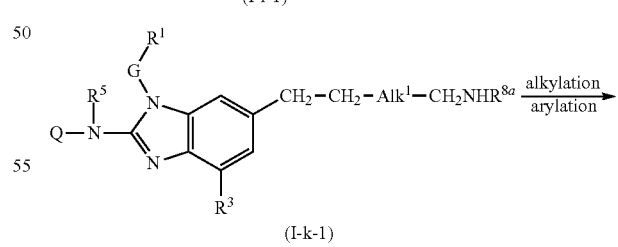

(I-l-1)

Precursors of the compounds of formula (I) wherein $R^{2a}$ or $R^{2b}$ is an aldehyde can be converted to the corresponding compounds wherein $R^{2a}$ or $R^{2b}$ is substituted $C_{2-6}$alkenyl (I-g-1) or (I-g-2), by a Wittig reaction or a Wittig-Horner reaction. In the former instance a Wittig type reagent is used, such as a triphenylphosphoniumylide in a suitable reaction-inert solvent such as an ether, starting from triphenylphosphine and a halo derivative. The Wittig-Horner reaction is performed using a phosphonate, such as e.g. a reagent of formula $di(C_{1-6}alkyloxy)-P(=O)-CH_2-CH_2-CN$ in the presence of a base, preferably a strong base, in an aprotic organic solvent. Compounds wherein $R^{2a}$ or $R^{3a}$ is substituted $C_{2-6}$alkenyl can be reduced to the corresponding compounds wherein $R^{2a}$ or $R^{3a}$ is substituted $C_{2-6}$alkyl (I-i-1) or (I-i-2), e.g. with hydrogen in the presence of a noble metal catalyst such as Pd/C. The cyano group in turn can be reduced to the corresponding methyleneamine ($-CH_2-NH_2$) group with hydrogen in the presence of a catalyst such as Raney Ni, in a suitable solvent such as methanol/ammonia. This reaction yields compounds (I-j-1) and (I-j-2) which can be monoalkylated or double alkylated to yield compounds (I-k-1), (I-k-2) and (I-l-1), (I-l-2). These alkylations may be done by a reductive alkylation reaction using an aldehyde or ketone in the presence of hydrogen and a catalyst (yielding mono-alkyl derivatives) or with suitably substituted alkyl halides (yielding mono- or dialkyl derivatives). These reactions are depicted in the following reaction schemes. In these schemes $R^{2a-1}$ represents CN, $Ar^3$ or Het, $Alk^1$ represents $C_{4-6}$alkanediyl radicals (which are as $C_{1-6}$alkanediyl, but having from 4-6 carbon atoms), $R^{8a}$ and $R^{8b}$ have the same meanings as defined in this specifications and claims, but preferably are other than $Ar^3$.

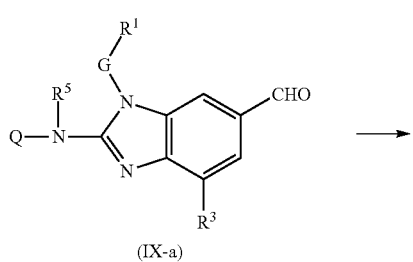

(IX-a)

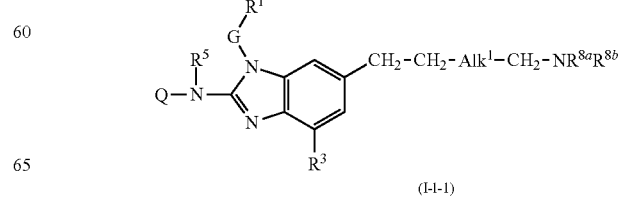

(I-l-1)

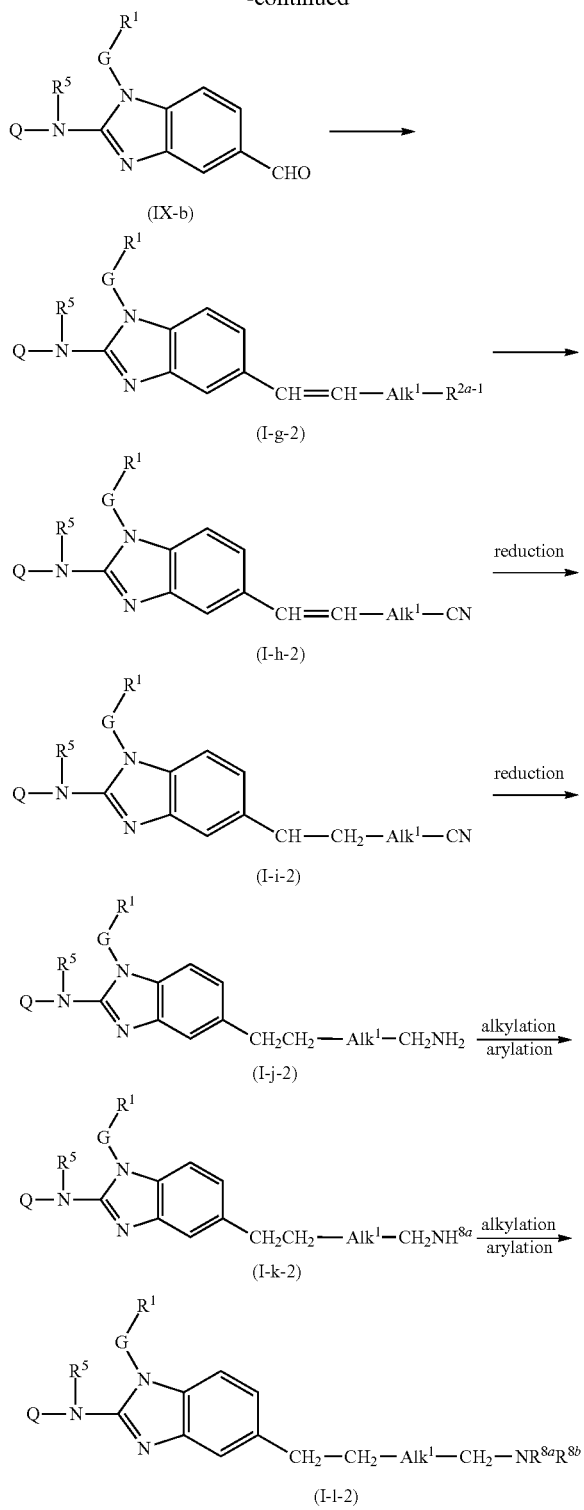

Compounds of formula (I) wherein $R^{2a}$ or $R^{2b}$ is an aldehyde or $C_{1-6}$alkyl substituted with a keto or an aldehyde can also be derivatized with a Grignard type of reaction to introduce aryl or alkyl groups.

An additional aspect of the present invention concerns the fact that some of the compounds identified as precursors of the compounds of formula (I), are novel compounds.

In particular the compounds of formula (VII-a), (VII-b), (VIII-a), (VIII-b), (IX-a), (IX-b), (I-f-1), (I-f-2), (I-g-1), (I-g-2) wherein G, $R^1$, $R^{2a}$, $R^{2b}$, $R^3$, $R^5$, $R^{8a}$, $R^{8b}$, $R^{12}$ are as defined above in the definitions of the compounds of formula (I) or in any of the subgroups thereof, and wherein Q is pyrrolidinyl, piperidinyl or homopiperidinyl, substituted on their nitrogen with a radical $R^6$ which is $C_{1-6}$alkyl optionally substituted with one or more, preferably one or two, substituents each independently selected from the group consisting of trifluoromethyl, $C_{3-7}$cycloalkyl, $Ar^2$, hydroxy, $C_{1-4}$alkoxy, $C_{1-4}$alkylthio, $Ar^2$-oxy-, $Ar^2$-thio-, $Ar^2(CH_2)_n$oxy, $Ar^2(CH_2)_n$thio, hydroxycarbonyl, aminocarbonyl, $C_{1-4}$alkylcarbonyl, $Ar^2$carbonyl, $C_{1-4}$alkoxycarbonyl, $Ar^2(CH_2)_n$carbonyl, aminocarbonyloxy, $C_{1-4}$alkylcarbonyloxy, $Ar^2$carbonyloxy, $Ar^2(CH_2)_n$carbonyloxy, $C_{1-4}$alkoxycarbonyl$(CH_2)_n$oxy, mono- or di($C_{1-4}$alkyl)aminocarbonyl, mono- or di($C_{1-4}$alkyl)aminocarbonyloxy, aminosulfonyl, mono- or di($C_{1-4}$alkyl)aminosulfonyl or a heterocycle selected from the group consisting of pyrrolidinyl, pyrrolyl, dihydropyrrolyl, imidazolyl, triazolyl, piperidinyl, homopiperidinyl, piperazinyl, dioxolanyl, dioxanyl, pyridyl and tetrahydropyridyl, wherein each of said heterocycle may optionally be substituted with one or two substituents selected from oxo or $C_{1-6}$alkyl; and wherein said $R^6$ can be represented by $R^{6b}$, as well as the pharmaceutically acceptable salt forms thereof, and the possible stereoisomeric forms thereof, are novel compounds.

Of particular interest are any of the groups of novel compounds specified in the previous paragraph wherein:

(a) $R^{6b}$ is $C_{1-6}$alkyl optionally substituted with two substituents or, preferably, with one substituent, each independently selected from the group consisting of trifluoromethyl, $Ar^2$, hydroxy, $C_{1-4}$alkoxy, $Ar^2(CH_2)_n$oxy, hydroxycarbonyl, aminocarbonyl, $C_{1-4}$alkylcarbonyl, $C_{1-4}$alkoxycarbonyl, $Ar^2(CH_2)_n$carbonyl, aminocarbonyloxy, $C_{1-4}$alkylcarbonyloxy, $Ar^2$carbonyloxy, mono- or di($C_{1-4}$alkyl)aminocarbonyl, aminosulfonyl, mono- or di($C_{1-4}$alkyl)aminosulfonyl or a heterocycle selected from the group consisting of pyrrolidinyl, imidazolyl, piperidinyl, homopiperidinyl, piperazinyl, dioxolanyl, dioxanyl and pyridyl, wherein each of said heterocycle may optionally be substituted with one or two radicals selected from oxo and $C_{1-6}$alkyl; or in particular (b) $R^{6b}$ is $C_{1-6}$alkyl optionally substituted with one substituent and, optionally with a further substituent which is hydroxy, wherein said substituent is trifluoromethyl, $Ar^2$, hydroxy, $C_{1-4}$alkoxy, $Ar^2(CH_2)_n$oxy, hydroxycarbonyl, aminocarbonyl, $C_{1-4}$alkylcarbonyl, $C_{1-4}$alkoxycarbonyl, $Ar^2(CH_2)_n$carbonyl, aminocarbonyloxy, $C_{1-4}$alkylcarbonyloxy, $Ar^2$carbonyloxy, mono- or di($C_{1-4}$alkyl)aminocarbonyl, aminosulfonyl, mono- or di($C_{1-4}$alkyl)aminosulfonyl or a heterocycle selected from the group consisting of pyrrolidinyl, imidazolyl, piperidinyl, homopiperidinyl, piperazinyl, dioxolanyl, dioxanyl and pyridyl, wherein each of said heterocycle may optionally be substituted with one or two radicals selected from oxo and $C_{1-6}$alkyl; or further in particular (c) $R^{6b}$ is $C_{1-6}$alkyl optionally substituted with $Ar^2$, hydroxy, $C_{1-4}$alkoxy, hydroxycarbonyl, aminocarbonyl, aminosulfonyl, $C_{1-4}$alkoxycarbonyl or $C_{1-6}$alkyl substituted with two hydroxy radicals, or $C_{1-6}$alkyl substituted with a heterocycle selected from dioxolanyl, pyrrolidinyl, piperidinyl, homopiperidinyl, piperazinyl, wherein each of said heterocycle may optionally be substituted with oxo or with one or two $C_{1-6}$alkyl radicals; or further in particular (d) $R^{6b}$ is $C_{1-6}$alkyl optionally substituted with $Ar^2$, hydroxy, hydroxycarbonyl, aminocarbonyl, aminosulfonyl or $C_{1-6}$alkyl substituted with two hydroxy radicals, or $C_{1-6}$alkyl substituted with a heterocycle selected from dioxolanyl, pyrrolidinyl, piperidinyl, homopiperidinyl, piperazinyl, wherein each of said heterocycle may optionally be substituted with oxo or with one or two $C_{1-6}$alkyl radicals; or further in particular wherein
(e) $R^{6b}$ is $C_{1-6}$alkyl optionally substituted with $Ar^2$, hydroxy, aminocarbonyl or aminosulfonyl, or $C_{1-6}$alkyl substituted with two hydroxy radicals, or $C_{1-6}$alkyl substituted with a heterocycle selected from dioxolanyl, pyrrolidinyl, piperidinyl, piperazinyl, wherein each of said heterocycle may optionally be substituted with one or two $C_{1-6}$alkyl radicals; or preferably
(f) $R^{6b}$ is $C_{1-6}$alkyl optionally substituted with $Ar^2$, hydroxy, aminocarbonyl, aminosulfonyl, or $C_{1-6}$alkyl substituted with two hydroxy radicals, or $C_{1-6}$alkyl substituted with pyrrolidinyl, piperidinyl, piperazinyl, 4-$C_{1-6}$alkyl-piperazinyl; or preferably
(g) $R^{6b}$ is $C_{1-6}$alkyl optionally substituted with $Ar^2$, hydroxy, aminocarbonyl or aminosulfonyl; or preferably
(h) $R^{6b}$ is $C_{1-6}$alkyl.

Preferably in (a)-(h) in the previous paragraph the radicals pyrrolidinyl, piperidinyl, homopiperidinyl or piperazinyl are linked by their nitrogen atom to the $C_{1-6}$alkyl on which they are substituted.

Moreover these compounds have found to possess antiviral properties, in particular to possess RSV inhibitory activity. Of particular interest are the compounds of formula (VII-a), (VII-b), (VIII-a) and (VIII-b) wherein Q is 4-piperidinyl wherein the ring nitrogen is substituted with a radical $R^6$ which is $C_{1-6}$alkyl, as well as the pharmaceutically acceptable salt forms thereof, and the possible stereoisomeric forms thereof. As used herein, the terms 'pharmaceutically acceptable salt forms' and the 'stereoisomeric forms' have the meanings specified above in this specification.

Also the compounds of formula (VII-a), (VII-b), (VIII-a), (VIII-b), (IX-a), (IX-b), (I-f-1), (I-f-2), (I-g-1), (I-g-2) wherein G, $R^1$, $R^{2a}$, $R^{2b}$, $R^3$, $R^5$, $R^{8a}$, $R^{8b}$ and $R^{12}$ are as defined above in the definitions of the compounds of formula (I) or in any of the subgroups thereof, and wherein Q is $R^{6b}$ which is as specified in the previous paragraphs, as well as the pharmaceutically acceptable salt forms thereof, and the possible stereoisomeric forms thereof, are novel compounds. Moreover these compounds have found to possess antiviral properties, in particular to possess RSV inhibitory activity.

Of particular interest are those compounds mentioned in the previous paragraph wherein G, $R^1$, $R^{2a}$, $R^{2b}$, $R^3$, $R^5$, $R^{8a}$ and $R^{8b}$ are as specified in any of the subgroups mentioned in this specification and claims. Preferred are those novel compounds mentioned in the previous paragraphs wherein G is $C_{1-6}$alkanediyl, more preferably wherein G is methylene; and/or wherein $R^{2a}$, $R^{2b}$, $R^3$, $R^5$ are all hydrogen; and/or $R^1$ is pyridyl being substituted as outlined in this specification and claims, in particular $R^1$ is pyridyl being substituted with one or two substituents selected from $C_{1-6}$alkyl and hydroxy.

Compounds of formula (I) may be converted into each other following art-known functional group transformation reactions, comprising those described hereinafter.

Nitro groups can be reduced to amino groups, which subsequently may be alkylated to mono- or dialkylamino groups, or acylated to arylcarbonylamino or alkylcarbonylamino and the like groups. Cyano groups may be reduced to aminomethylene groups, which similarly may be derivatized.

A number of the intermediates used to prepare the compounds of formula (I) are known compounds or are analogs of known compounds, which can be prepared following modifications of art-known methodologies readily accessible to the skilled person. A number of preparations of intermediates are given hereafter in somewhat more detail.

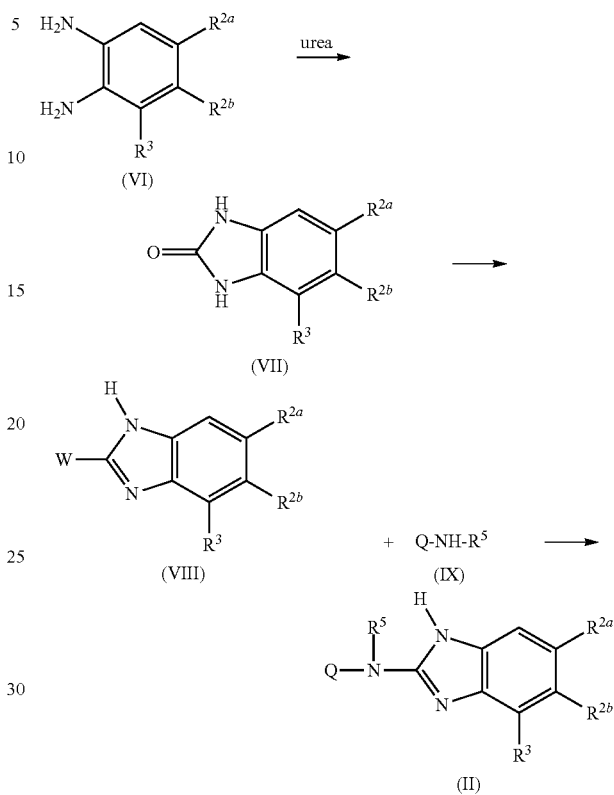

In a first step, a diaminobenzene (VI) is cyclized with urea in a suitable solvent, e.g. xylene, to yield a benzimidazolone (VII). The latter is converted to a benzimidazole derivative (VIII) wherein W is a leaving group as specified above, in particular by reaction of (VII) with a suitable halogenating agent, for example $POCl_3$, and the resulting intermediate (VIII) is reacted with the amine derivative (IX) to obtain intermediate (II).

The same reaction sequence may be used to prepare other intermediates. For example the intermediates of formula (IV) can be prepared by reacting intermediates (IX) with an amine (X) wherein Q is a pyrrolinyl, piperidinyl or homopiperidinyl group wherein the nitrogen is substituted with a protective group to yield precursors of (IV) which can be converted to intermediates (IV) by removing the protective group. Suitable protecting groups for this purpose comprise alkyloxycarbonyl groups such as methoxy or ethoxycarbonyl, which can be removed with a base, or benzyl or benzyloxycarbonyl groups, which can be removed with hydrogen in the presence of a catalyst.

The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t.butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Pure stereochemically isomeric forms of the compounds of formula (I) may be obtained by the application of art-known procedures. Diastereomers may be separated by physical methods such as selective crystallization and chromatographic techniques, e.g., counter-current distribution, liquid chromatography and the like.

The compounds of formula (I) as prepared in the hereinabove described processes are generally racemic mixtures of enantiomers which can be separated from one another following art-known resolution procedures. The racemic compounds of formula (I), which are sufficiently basic or acidic may be converted into the corresponding diastereomeric salt forms by reaction with a suitable chiral acid, respectively chiral base. Said diastereomeric salt forms are subsequently separated, for example, by selective or fractional crystallization and the enantiomers are liberated therefrom by alkali or acid. An alternative manner of separating the enantiomeric forms of the compounds of formula (I) involves liquid chromatography, in particular liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

In a further aspect, the present invention concerns a pharmaceutical composition comprising a therapeutically effective amount of a compound of formula (I) as specified herein, or a compound of any of the subgroups of compounds of formula (I) as specified herein, and a pharmaceutically acceptable carrier. A therapeutically effective amount in this context is an amount sufficient to prophylaxictically act against, to stabilize or to reduce viral infection, and in particular RSV viral infection, in infected subjects or subjects being at risk of being infected. In still a further aspect, this invention relates to a process of preparing a pharmaceutical composition as specified herein, which comprises intimately mixing a pharmaceutically acceptable carrier with a therapeutically effective amount of a compound of formula (I), as specified herein, or of a compound of any of the subgroups of compounds of formula (I) as specified herein.

Therefore, the compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form or metal complex, as the active ingredient is combined in intimate admixture with a pharmaceutically acceptable carrier, which carrier may take a wide variety of forms depending on the form of preparation desired for administration. These pharmaceutical compositions are desirable in unitary dosage form suitable, particularly, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions and solutions; or solid carriers such as starches, sugars, kaolin, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. Also included are solid form preparations which are intended to be converted, shortly before use, to liquid form preparations. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin.

The compounds of the present invention may also be administered via oral inhalation or insufflation by means of methods and formulations employed in the art for administration via this way. Thus, in general the compounds of the present invention may be administered to the lungs in the form of a solution, a suspension or a dry powder, a solution being preferred. Any system developed for the delivery of solutions, suspensions or dry powders via oral inhalation or insufflation are suitable for the administration of the present compounds.

Thus, the present invention also provides a pharmaceutical composition adapted for administration by inhalation or insufflation through the mouth comprising a compound of formula (I) and a pharmaceutically acceptable carrier. Preferably, the compounds of the present invention are administered via inhalation of a solution in nebulized or aerosolized doses.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, suppositories, powder packets, wafers, injectable solutions or suspensions and the like, and segregated multiples thereof.

The compounds of formula (I) show antiviral properties. Viral infections treatable using the compounds and methods of the present invention include those infections brought on by ortho- and paramyxoviruses and in particular by human and bovine respiratory syncytial virus (RSV). A number of the compounds of this invention moreover are active against mutated strains of RSV. Additionally, many of the compounds of this invention show a favorable pharmacokinetic profile and have attractive properties in terms of bioavailabilty, including an acceptable half-life, AUC and peak values and lacking unfavourable phenomena such as insufficient quick onset and tissue retention.

The in vitro antiviral activity against RSV of the present compounds was tested in a test as described in the experimental part of the description, and may also be demonstrated in a virus yield reduction assay. The in vivo antiviral activity against RSV of the present compounds may be demonstrated in a test model using cotton rats as described in Wyde et al. (Antiviral Research (1998), 38, 31-42).

Due to their antiviral properties, particularly their anti-RSV properties, the compounds of formula (I) or any subgroup thereof, their prodrugs, N-oxides, addition salts, quaternary amines, metal complexes and stereochemically isomeric forms, are useful in the treatment of individuals experiencing a viral infection, particularly a RSV infection, and for the prophylaxis of these infections. In general, the compounds of the present invention may be useful in the treatment of warm-blooded animals infected with viruses, in particular the respiratory syncytial virus.

The compounds of the present invention or any subgroup thereof may therefore be used as medicines. Said use as a medicine or method of treatment comprises the systemic administration to viral infected subjects or to subjects susceptible to viral infections of an amount effective to combat the conditions associated with the viral infection, in particular the RSV infection.

The present invention also relates to the use of the present compounds or any subgroup thereof in the manufacture of a medicament for the treatment or the prevention of viral infections, particularly RSV infection.

The present invention furthermore relates to a method of treating a warm-blooded animal infected by a virus, or being at risk of infection by a virus, in particular by RSV, said method comprising the administration of an anti-virally effective amount of a compound of formula (I), as specified herein, or of a compound of any of the subgroups of compounds of formula (I), as specified herein.

In general it is contemplated that an antiviral effective daily amount would be from 0.01 mg/kg to 500 mg/kg body weight, more preferably from 0.1 mg/kg to 50 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight, sex, extent of disorder and general physical condition of the particular patient as well as other medication the individual may be taking, as is well known to those skilled in the art. Furthermore, it is evident that said effective daily amount may be lowered or increased depending on the response of the treated subject and/or depending on the evaluation of the physician prescribing the compounds of the instant invention. The effective daily amount ranges mentioned hereinabove are therefore only guidelines.

Also, the combination of another antiviral agent and a compound of formula (I) can be used as a medicine. Thus, the present invention also relates to a product containing (a) a compound of formula (I), and (b) another antiviral compound, as a combined preparation for simultaneous, separate or sequential use in antiviral treatment. The different drugs may be combined in a single preparation together with pharmaceutically acceptable carriers. For instance, the compounds of the present invention may be combined with interferon-beta or tumor necrosis factor-alpha in order to treat or prevent RSV infections.

EXAMPLES

The following examples are intended to illustrate the present invention and not to limit it thereto. The terms 'compound 1', 'compound 2', etc. used in these examples refers to the same compounds in the tables.

The compounds were identified by LC/MS using the following equipment:

LCT: electrospray ionisation in positive mode, scanning mode from 100 to 900 amu; Xterra MS C18 (Waters, Milford, Mass.) 5 µm, 3.9×150 mm); flow rate 1 ml/min. Two mobile phases (mobile phase A: 85% 6.5 mM ammonium acetate+15% acetonitrile; mobile phase B: 20% 6.5 mM ammonium acetate+80% acetonitrile) were employed to run a gradient from 100% A for 3 min to 100% B in 5 min., 100% B for 6 min to 100% A in 3 min, and equilibrate again with 100% A for 3 min).

ZQ: electrospray ionisation in both positive and negative (pulsed) mode scanning from 100 to 1000 amu; Xterra RP C18 (Waters, Milford, Mass.) 5 µm, 3.9×150 mm); flow rate 1 ml/min. Two mobile phases (mobile phase A: 85% 6.5 mM ammonium acetate+15% acetonitrile; mobile phase B: 20% 6.5 mM ammonium acetate+80% acetonitrile) were employed to run a gradient condition from 100% A for 3 min to 100% B in 5 min., 100% B for 6 min to 100% A in 3 min, and equilibrate again with 100% A for 3 min).

Example 1

Scheme A

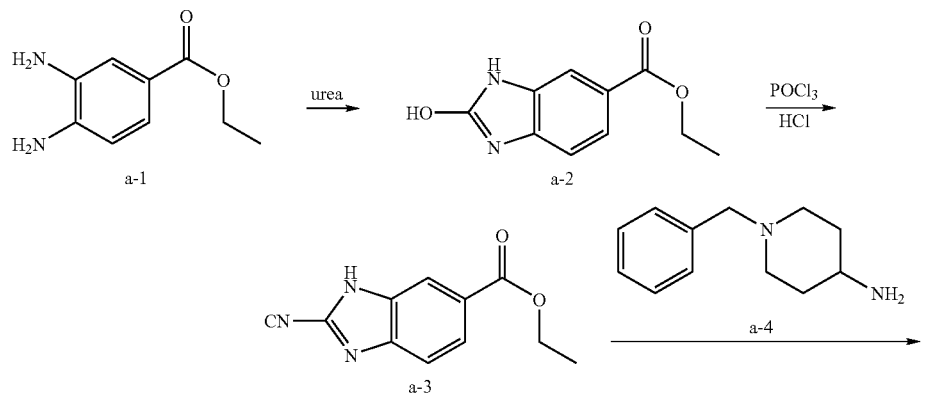

-continued
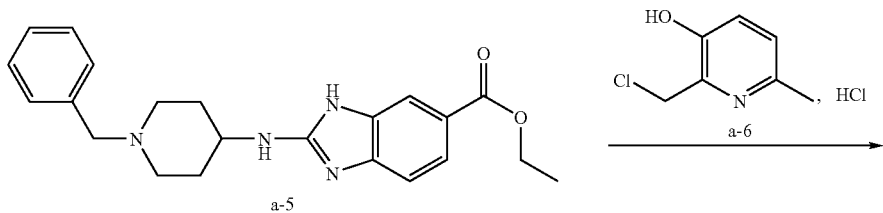
a-5
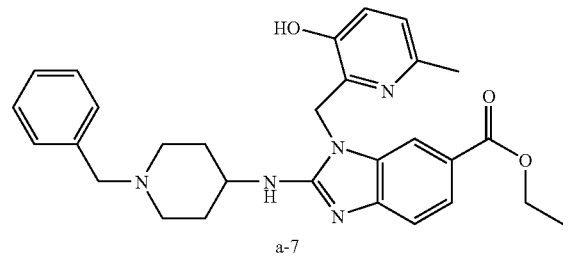
a-7 +
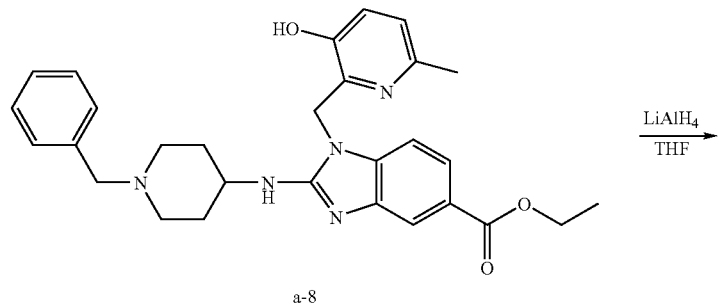
a-8
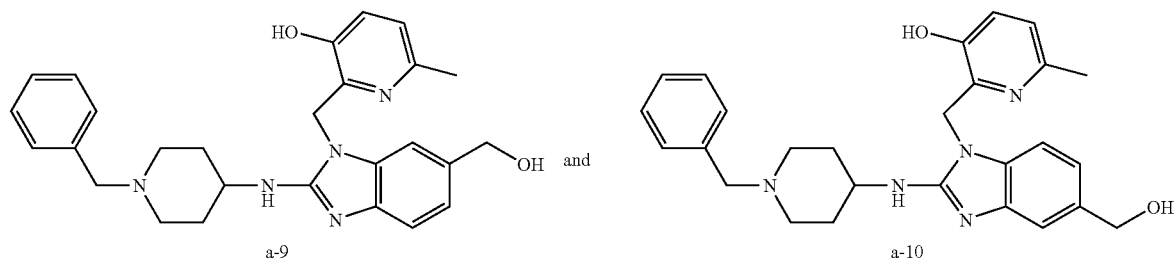
a-9 and a-10
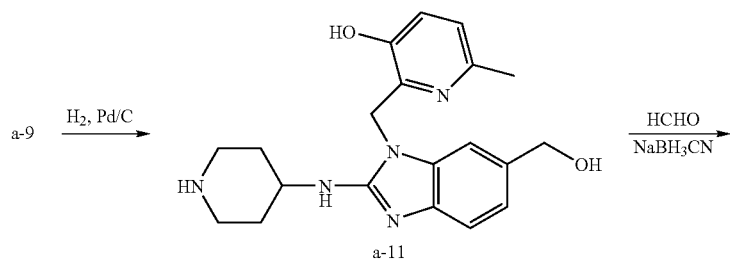
a-11
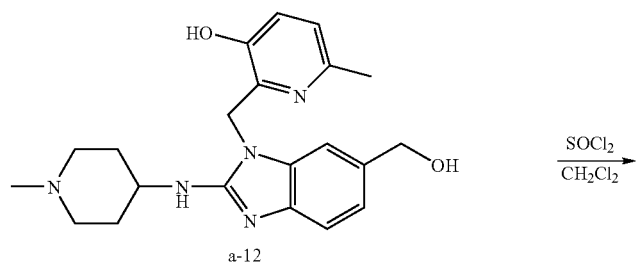
a-12

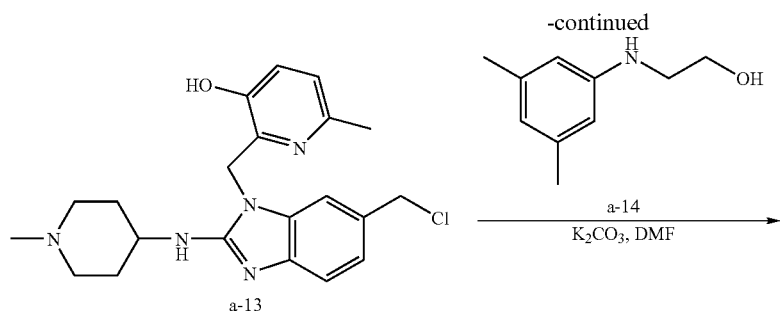

A mixture of a-1 (0.166 mol) and urea (0.199 mol) in xylene (300 ml) was stirred under reflux for 12 hours. The reaction was cooled down to room temperature. The precipitate was filtered off, rinsed with xylene and diisopropyl ether, and then dried, yielding 32 g of intermediate a-2 (93%, melting point: >260° C.).

A mixture of a-2 (0.073 mol) in $POCl_3$ (150 ml) was stirred at 100° C. HCl conc. (around 1.5 ml) was added drop wise very carefully until the dissolution of a-2. The mixture was stirred at 120° C. for 6 hours. The solvent was evaporated until dryness. The residue was taken-up in $H_2O$/ice, basified with $K_2CO_3$ (powder) and extracted with ethylacetate+10% methanol. The organic layer was separated, dried (over $MgSO_4$), filtered and the solvent was evaporated until dryness, yielding 13.5 g of intermediate a-3 (83%, melting point: 178° C.).

A mixture of a-3 (0.051 mmol) and a-4 (0.056 mol) was stirred at 160° C. for 2 hours. The residue was taken-up in $CH_2Cl_2/H_2O$ and basified with a 10% solution of $K_2CO_3$ in water. The organic layer was separated, dried (over $MgSO_4$), filtered and the solvent was evaporated until dryness. The residue was purified by column chromatography over silica gel (eluent: $CH_2Cl_2$/methanol/$NH_4OH$ 95/5/0.5). The pure fractions were collected and the solvent was evaporated, yielding 15.3 g of intermediate a-5 (79%).

A mixture of a-5 (0.0396 mol), a-6 (0.059 mol) and $K_2CO_3$ (0.1584 mol) in $CH_3CN$ (180 ml) was stirred and refluxed for 12 hours. The solvent was evaporated until dryness. The residue was taken up in $CH_2Cl_2$. The organic layer was washed with $H_2O$, dried (over $MgSO_4$), filtered and the solvent was evaporated until dryness. The residue (20 g) was purified by column chromatography over silica gel (eluent: Toluene/2-propanol/$NH_4OH$ 85/15/1; 20-45 μm). Two fractions were collected and the solvent was evaporated, yielding 5.3 g of fraction 1 (27%) and 6.3 g of fraction 2 (32%). Fraction 1 was crystallized twice in 2-propanone/$CH_3CN$/diisopropylether. The precipitate was filtered off and dried, yielding 4.9 g of intermediate a-7 (25%, melting point: 179° C.). Fraction 2 was crystallized from 2-propanone/$CH_3CN$/diisopropylether. The precipitate was filtered off and dried, yielding 5.5 g of intermediate a-8 (28%, melting point: 238° C.).

$LiAlH_4$ (0.009 mol) was added portion wise to a mixture of a-7 (0.003 mol) in tetrahydrofuran (60 ml) at 5° C. under $N_2$ flow. The reaction was stirred at 5° C. for 1 hour and then at room temperature for 12 hours. Ethyl acetate and $H_2O$ were added carefully and the aqueous layer was saturated with $K_2CO_3$ (powder). The organic layer was separated, dried (over $MgSO_4$) and then filtered over celite. The filtrate was evaporated until dryness, yielding 1.3 g of intermediate a-9 (97%). The crude product was used directly in the next reaction step.

Intermediate a-10 was prepared analogously to the procedure described for intermediate a-9.

A mixture of a-9 (0.0028 mol) and Pd/C 10% (2.5 g) in $CH_3OH$ (40 ml) was hydrogenated at 40° C. for 12 hours under an 8 bar pressure, then filtered over celite. Celite was washed with a solution of $CH_3OH$/tetrahydrofuran (50/50). The filtrate was evaporated until dryness, yielding 1.8 g of intermediate a-11 (95%, melting point: 260° C.).

HCHO 37% in water (0.0098 mol), $NaBH_3CN$ (0.0059 mol) then $CH_3CO_2H$ (2 ml) were added at room temperature to a mixture of a-11 (0.0049 mol) in $CH_3CN$ (50 ml). The mixture was stirred at room temperature for 12 hours. The solvent was evaporated until dryness. The residue was taken up in ethanol (30 ml) and a 5N solution of HCl in 2-propanol (4 ml) was added. The mixture was stirred at 80° C. for 8 hours. The solvent was evaporated until dryness. The residue was taken up in $CH_2Cl_2/K_2CO_3$ 10%. The organic layer was separated, dried (over $MgSO_4$), filtered and the solvent was evaporated until dryness. The residue was crystallized from $CH_3OH$/2-propanone/$CH_3CN$. The precipitate was filtered off and dried, yielding 1.65 g of a-12 (88%). Part of this fraction (0.15 g) was crystallized from $CH_3OH$/2-propanone. The precipitate was filtered off and dried (melting point: 165° C.).

$SOCl_2$ (2.1 ml) was added drop wise to a mixture of a-12 (0.0018 mol) in $CH_2Cl_2$ (20 ml) at 5° C. The mixture was stirred at 5° C. for 1 hour, then at room temperature for 12 hours. The solvent was evaporated until dryness, yielding 0.93 g of intermediate a-13 (100%). The crude product was used directly in the next reaction step.

A mixture of a-13 (0.0003 mol), a-14 (0.0005 mol) and $K_2CO_3$ (0.0019 mol) in dimethylformamide (30 ml) was stirred at 80° C. for 4 hours and poured into $H_2O$. The aqueous layer was saturated with $K_2CO_3$ and extracted with $CH_2Cl_2$/$CH_3OH$. The organic layer was separated, dried (over $MgSO_4$), filtered and the solvent was evaporated until dryness. The residue (0.25 g) was purified by column chromatography over silica gel (eluent: $CH_2Cl_2$/$CH_3OH$/$NH_4OH$ 90/10/1; 10 μm). The pure fractions were collected and the solvent was evaporated. The residue (0.05 g, 24%) was crystallized from 2-propanone/diisopropylether. The precipitate was filtered off and dried, yielding 0.042 g of compound a-15 (20%, compound 1, melting point: 201° C.).

Example 2

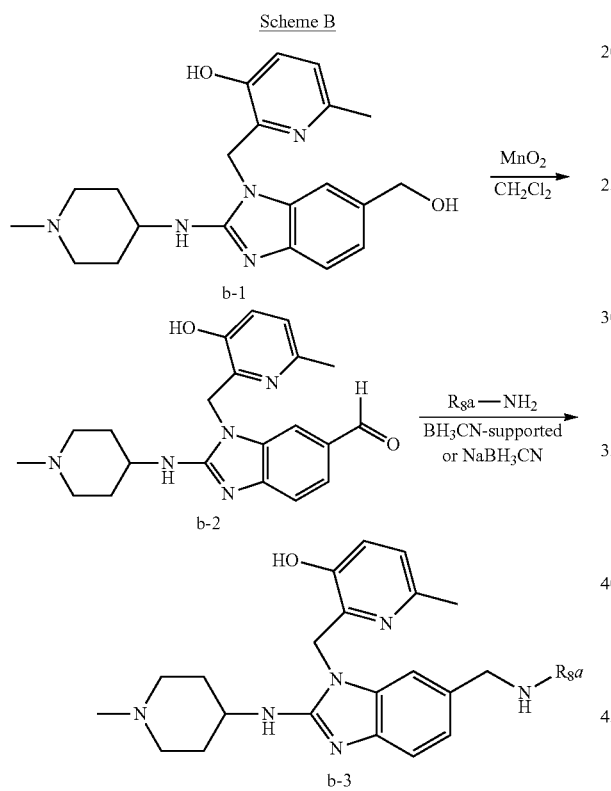

A mixture of b-1 (0.0028 mol) and $MnO_2$ (2.5 g) in $CH_2Cl_2$ (40 ml) was stirred at room temperature for 12 hours, and then filtered over celite. Celite was rinsed with $CH_2Cl_2$. The filtrate was evaporated until dryness. The residue was taken up in 2-propanone. The precipitate was filtered off and dried, yielding 0.75 g of intermediate b-2 (69%, melting point: 250° C.).

Variant 1: A mixture of b-2 (0.0001 mol), 3,5-dichloro aniline (0.0001 mol), $BH_3CN$ on solid support (0.0001 mol) and $CH_3CO_2H$ (2 drops) in $CH_3OH$ (4 ml) was stirred at room temperature for 24 hours. The solution was filtered. The filtrate was evaporated until dryness. The residue was purified by column chromatography over silica gel (eluent: $CH_2Cl_2$/$CH_3OH$/$NH_4OH$ 87/12/1.5; 5 μm). The pure fractions were collected and the solvent was evaporated, yielding 0.026 g of 2-[6-[(3,5-dichloro-phenylamino)-methyl]-2-(1-methyl-piperidin-4-ylamino)-benzoimidazol-1-ylmethyl]-6-methyl-pyridin-3-ol (38%, compound 2).

Variant 2: b-2 (0.0005 mol), $NaBH_3CN$ (0.0006 mol), and then $CH_3CO_2H$ (0.2 ml) were added at room temperature to a mixture of 3-methyl-aniline (0.0006 mol) in $CH_3CN$ (20 ml). The mixture was stirred at room temperature for 12 hours. $H_2O$ was added. The mixture was saturated with $K_2CO_3$ (powder) and extracted with $CH_2Cl_2$/$CH_3OH$. The organic layer was separated, dried (over $MgSO_4$), filtered and the solvent was evaporated until dryness. The residue (0.3 g) was purified by column chromatography over silica gel (eluent: $CH_2Cl_2$/$CH_3OH$/triethylamine; 90/10/0.1; 5 μm). The pure fractions were collected and the solvent was evaporated. The residue (0.17 g, 68%) was crystallized from $CH_3OH$/2-propanone/diisopropylether. The precipitate was filtered off and dried, yielding 0.13 g of 2-[6-[(1-ethylidene-3-methyl-penta-2,4-dienylamino)-methyl]-2-(1-methyl-piperidin-4-ylamino)-benzoimidazol-1-ylmethyl]-6-methyl-pyridin-3-ol (52%, compound 9, melting point: 141° C.).

Example 3

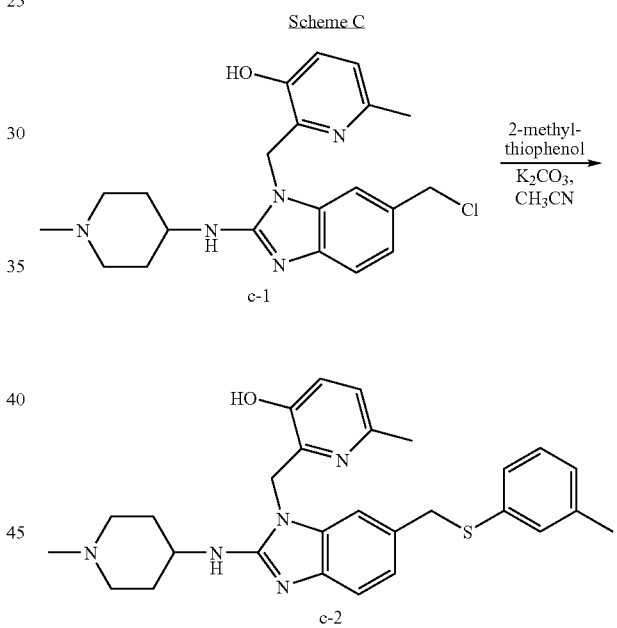

A mixture of c-1 (0.0018 mol), 2-methyl-thiophenol (0.002 mol) and $K_2CO_3$ (0.0077 mol) in $CH_3CN$ (70 ml) was stirred at 50° C. for 12 hours. The solvent was evaporated until dryness. The residue was taken up in $H_2O$. The mixture was extracted with $CH_2Cl_2$. The organic layer was separated, dried (over $MgSO_4$), filtered and the solvent was evaporated until dryness. The residue (0.55 g) was purified by column chromatography over silica gel (eluent: $CH_2Cl_2$/$CH_3OH$/$NH_4OH$ 88/12/2; 15-40 μm). The pure fractions were collected and the solvent was evaporated. The residue (0.35 g, 39%) was crystallized from $CH_3CN$/diisopropylether. The precipitate was filtered off and dried, yielding 0.32 g of 6-methyl-2-[2-(1-methyl-piperidin-4-ylamino)-6-m-tolylsulfanylmethyl-benzoimidazol-1-ylmethyl]-pyridin-3-ol (compound 93, melting point: 202° C.).

Example 4

Scheme D

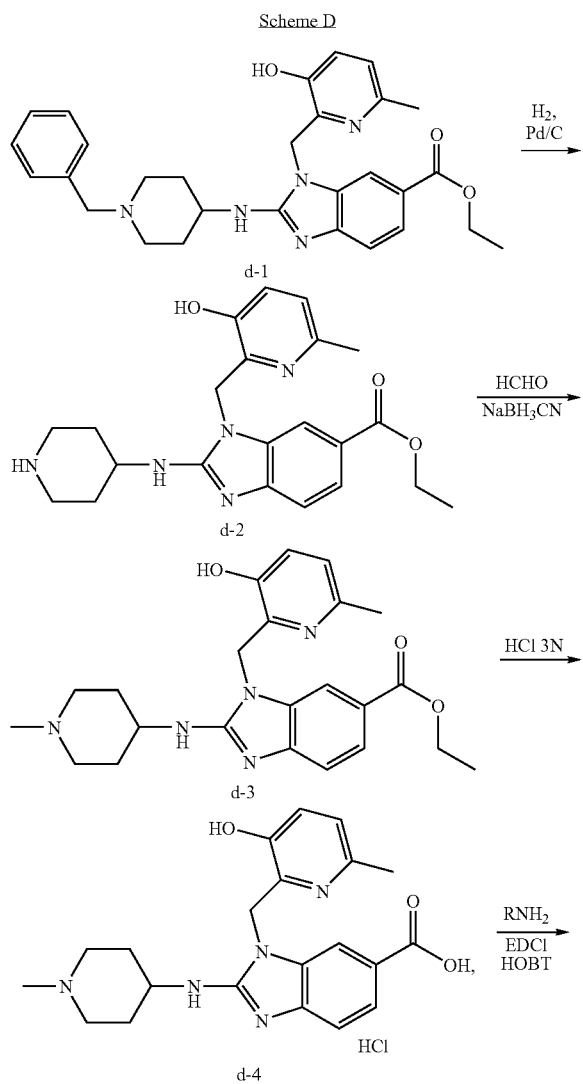

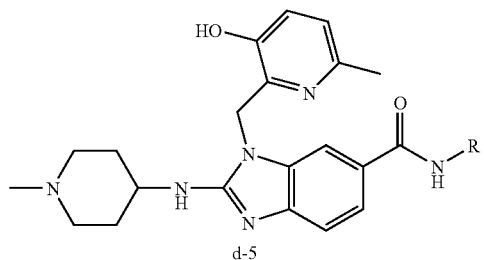

In scheme D, R is defined as $Ar^3$, $Het^1$, $Het^1(CH_2)_n$ or $Het^1(CH_2)_n$.

Intermediate d-2 (melting point: 262° C.) was prepared analogous to the procedure described for intermediate a-11. Intermediate d-3 was prepared analogous to the procedure described for intermediate a-12.

A mixture of d-3 (0.0003 mol) in a 3N solution of HCl in water (30 ml) was stirred at 80° C. for 12 hours. The solvent was evaporated. The residue was dried, yielding 0.18 g of intermediate d-4. The crude product was used directly in the next reaction step.

A mixture of d-4 (0.0003 mol), 2-methyl-aniline (0.0005 mol), 1-(3-dimethylaminopropyl)-3-ethylcarbodiimide hydrochloride (0.0005 mol) and 1-hydroxybenzotriazole (0.0005 mol) in $CH_2Cl_2$ (20 ml) was stirred at room temperature for 24 hours. A 10% solution of $K_2CO_3$ in water was added. The aqueous layer was saturated with $K_2CO_3$ (powder). The organic layer was separated, dried (over $MgSO_4$), filtered and the solvent was evaporated until dryness. The residue (0.2 g) was purified by column chromatography over silica gel (eluent: $CH_2Cl_2/CH_3OH/NH_4OH$ 80/20/1; 10 μm). The pure fractions were collected and the solvent was evaporated. Yielding: 0.29 g (14%). This fraction was taken up in diisopropyl ether, then $CH_3OH$/diisopropylether. The precipitate was filtered off and dried, yielding 0.007 g of 3-(3-hydroxy-6-methyl-pyridin-2-ylmethyl)-2-(1-methyl-piperidin-4-ylamino)-3H-benzoimidazole-5-carboxylic acid m-tolylamide (4%, compound 116, melting point: 172° C.).

Example 5

Scheme E

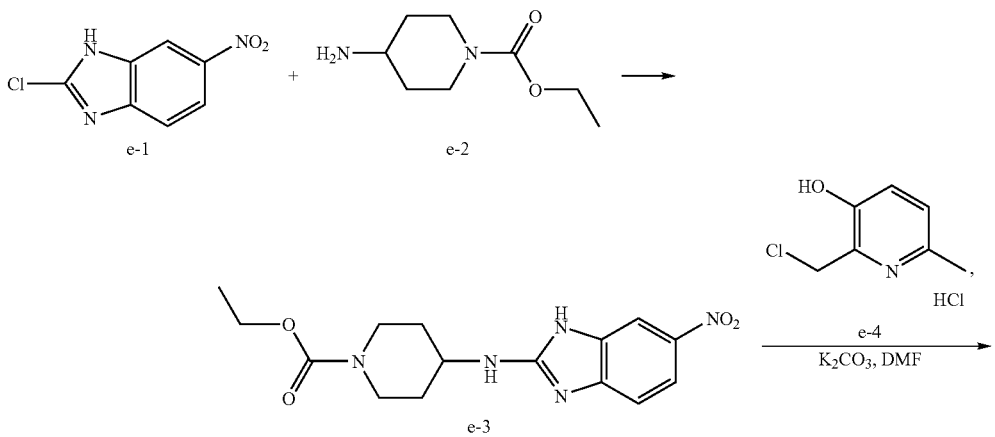

-continued

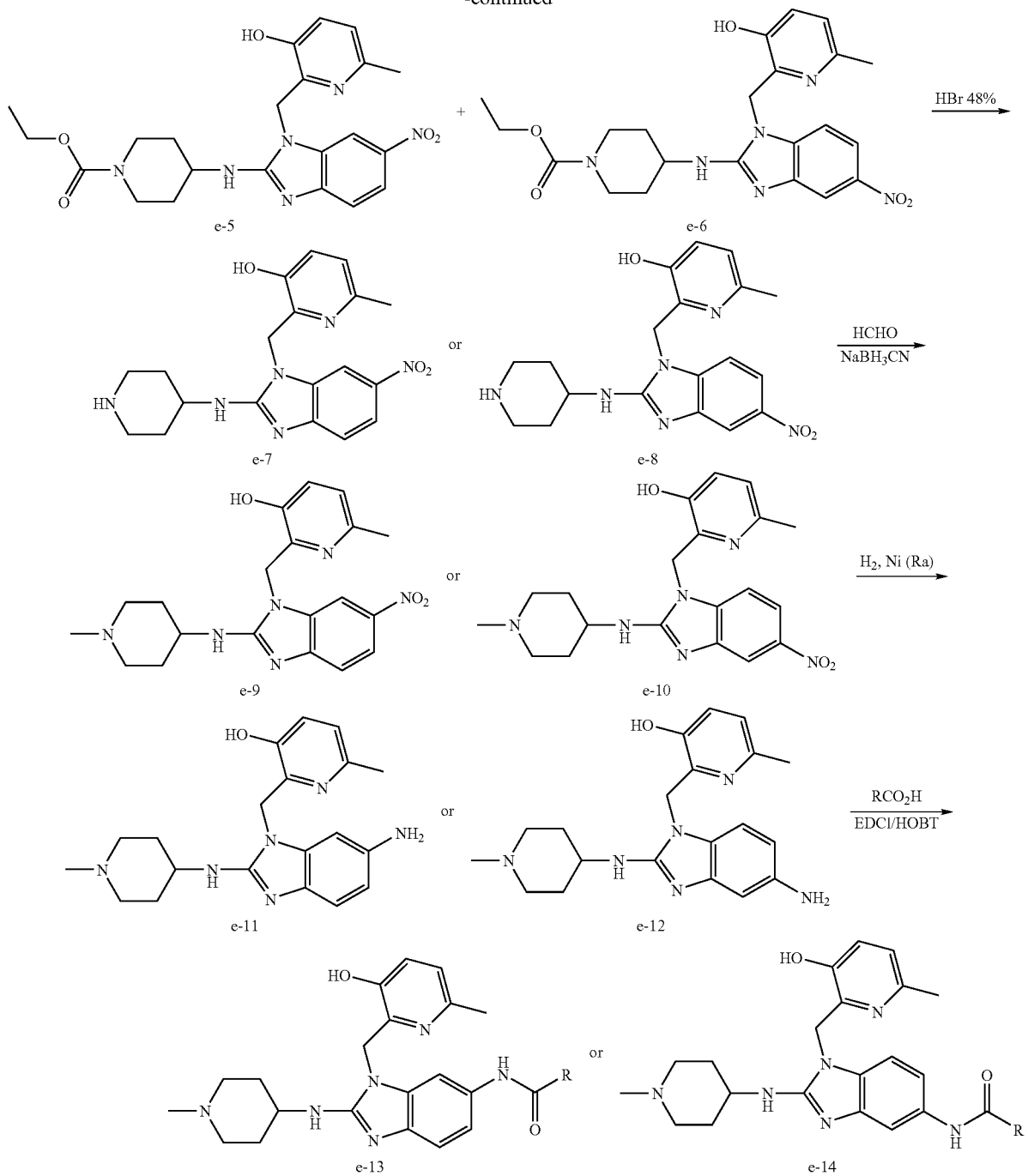

A mixture of e-1 (0.0524 mol) and e-2 (0.1048 mol) was stirred at 120° C. in a Parr pressure vessel for 10 hours, then taken up into H$_2$O and extracted with ethyl acetate. The separated organic layer was purified by short open column chromatography over silica gel (eluent: CH$_2$Cl$_2$/methanol 96/4). The product fractions were collected and the solvent was evaporated until dryness, yielding 7.7 g of intermediate e-3 (44%).

A mixture of e-3 (0.0312 mol), e-4 (0.0343 mol) and K$_2$CO$_3$ (0.1092 mol) in dimethyl formamide (100 ml) was stirred at 70° C. for 24 hours. H$_2$O was then added. The mixture was extracted with CH$_2$Cl$_2$. The organic layer was separated, dried (over MgSO$_4$), filtered and the solvent was evaporated until dryness. The residue (12.2 g) was purified by column chromatography over silica gel (eluent: toluene/isopropanol/NH$_4$OH 90/10/0.5; 15-40 µm). Two fractions were collected and the solvent was evaporated, yielding 4 g of intermediate e-5 (28%) and 5.4 g of intermediate e-6 (38%).

e-5 (0.0088 mol) was added portion wise to a 48% solution of HBr in water (40 ml). The mixture was brought slowly to 70° C., and then stirred for 12 hours. The precipitate was filtered, washed with CH$_3$CN and dried. The residue (4.6 g, 80%) was taken up in H$_2$O and basified with K$_2$CO$_3$ (powder). The precipitate was filtered, and then washed with ethanol. The filtrate was evaporated, yielding 3 g of intermediate e-7 (52%). In an analogous way, e-8 was prepared HCHO 37% in H₂O (0.0152 mol) then NaBH₃CN (0.0091 mol) were added at room temperature to a mixture of e-7 (0.0075 mol) in CH₃CN (100 ml). Acetic acid (3.5 ml) was added slowly at room temperature. The mixture was stirred at room temperature for 12 hours and poured into H₂O. The aqueous layer was saturated with K₂CO₃ (powder). The mixture was extracted with ethylacetate/CH₃OH. The organic layer was separated, dried (over MgSO₄), filtered and the solvent was evaporated until dryness, yielding 2.6 g of intermediate e-9 (87%). In an analogous way, e-10 was prepared.

A mixture of e-9 (0.0065 mol) and Raney Nickel (2.6 g) in CH₃OH (100 ml) was hydrogenated at room temperature for 1 hour under a 3 bar pressure, and then filtered over celite. Celite was washed with CH₃OH. The filtrate was evaporated. The residue (2.2 g) was purified by column chromatography over silica gel (eluent: CH₂Cl₂/CH₃OH/NH₄OH 85/14/1; 15-40 μm). The pure fractions were collected and the solvent was evaporated, yielding 0.85 g of intermediate e-11 (35%). In an analogous way, e-12 was prepared.

A mixture of e-11 (0.000125 mol) and 3-methyl-benzoic acid (0.00025 mol) in CH₂Cl₂ (4 ml) was stirred at room temperature. 1-hydroxybenzotriazole (0.00025 mol) and 1-(3-dimethylaminopropyl)-3-ethylcarbodiimide hydrochloride (0.00025 mol) were added. The reaction was stirred at room temperature for 12 hours. The solution was concentrated and a 10% solution of NaHCO₃ in water (2 ml) and CH₃OH (2 ml) were added. The mixture was stirred and refluxed for 4 hours. CH₃OH was then removed under reduced pressure and the resulting solution extracted with CH₂Cl₂. The organic layer was separated, dried (over MgSO₄), filtered and the solvent was evaporated until dryness. The residue was purified by column chromatography over silica gel (eluent: CH₂Cl₂/CH₃OH/NH₄OH 90/10/0.5; 15-40 μm). The pure fractions were collected and the solvent was evaporated, yielding 0.04 g of N-[3-(3-hydroxy-6-methyl-pyridin-2-yl-methyl)-2-(1-methyl-piperidin-4-ylamino)-3H-benzoimidazol-5-yl]-3-methyl-benzamide (60%, compound 65). In an analogous way, N-[1-(3-hydroxy-6-methyl-pyridin-2-ylmethyl)-2-(1-methyl-piperidin-4-ylamino)-1H-benzoimidazol-5-yl]-3-methyl-benzamide (0.028 g or 42% yield, compound 78) was prepared.

Example 6

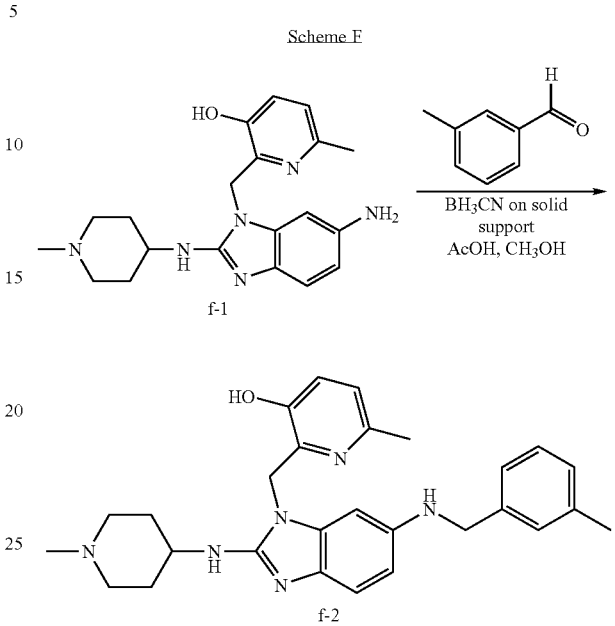

A mixture of f-1 (0.0005 mol), 3-methyl-benzaldehyde (0.0006 mol), BH₃CN on solid support (0.0006 mol) and acetic acid (8 drops) in CH₃OH (10 ml) was stirred at room temperature for 24 hours. The solid support was filtered and washed with CH₃OH. The filtrate was evaporated. The residue (0.53 g) was purified by column chromatography over silica gel (eluent: CH₂Cl₂/CH₃OH/NH₄OH 92/8/0.5 to 89/10/1; 10 μm). The pure fractions were collected and the solvent was evaporated. The residue (0.11 g) was crystallized from CH₃OH/disopropylether. The precipitate was separated and dried, yielding 0.072 g of compound f-2, i.e. 6-methyl-2-[6-(3-methyl-benzylamino)-2-(1-methyl-piperidin-4-ylamino)-benzoimidazol-1-ylmethyl]-pyridin-3-ol (28%, compound 28, melting point: 240° C.).

Example 7

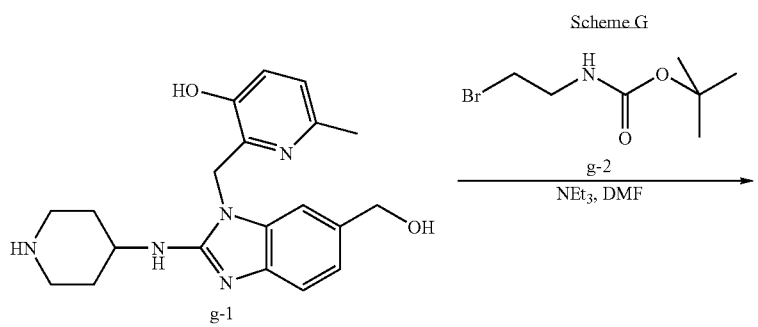

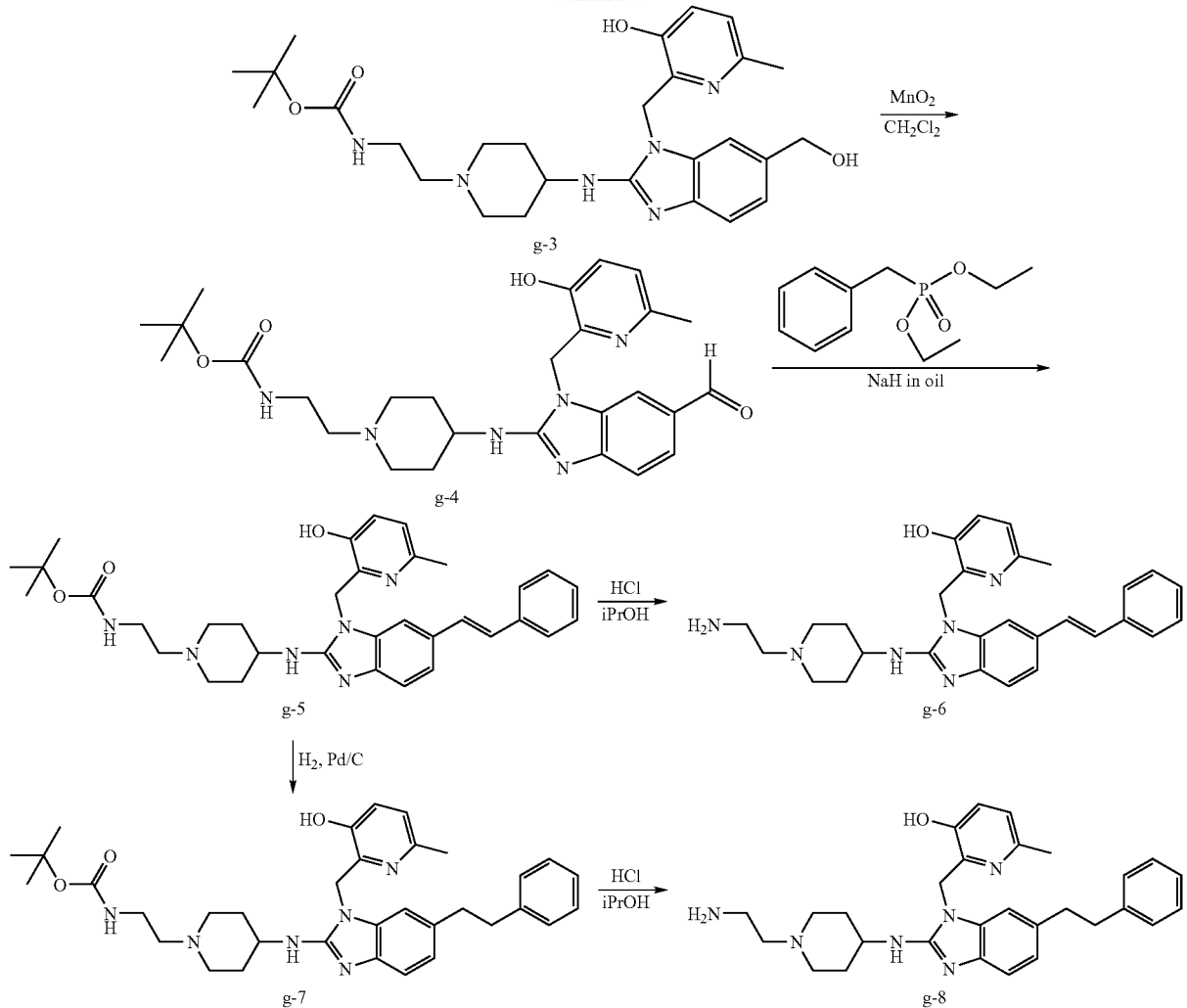

A mixture of g-1 (0.0079 mol), g-2 (0.0095 mol) and triethylamine (0.0118 mol) in dimethylformamide (60 ml) was stirred at 80° C. for 12 hours. The solvent was evaporated until dryness. The residue was taken up in CH$_2$Cl$_2$/H$_2$O. The organic layer was separated, dried (over MgSO$_4$), filtered and the solvent was evaporated until dryness. The residue (7 g) was purified by column chromatography over silica gel (eluent: CH$_2$Cl$_2$/CH$_3$OH/NH$_4$OH 90/10/0.5; 15-40 μm). The pure fractions were collected and the solvent was evaporated, yielding 1.2 g of intermediate g-3 (30%).

A mixture of g-3 (0.0023 mol) and MnO$_2$ (2.4 g) in CH$_2$Cl$_2$ (80 ml) was stirred at room temperature for 12 hours, and then filtered over celite. Celite was washed with H$_2$O. The filtrate was evaporated until dryness. The residue (1.2 g) was purified by column chromatography over silica gel (eluent: CH$_2$Cl$_2$/CH$_3$OH/NH$_4$OH 95/5/0.1; 35-70 μm). The pure fractions were collected and the solvent was evaporated, yielding 0.8 g of intermediate g-4 (67%).

Diethyl benzyl phosphonate (0.0023 mol) was added to a mixture of NaH (0.0047 mol) in tetrahydrofuran (20 ml) at 5° C. under N$_2$ flow. The mixture was stirred at 5° C. for 30 minutes. A solution of g-4 (0.0007 mol) in tetrahydrofuran (10 ml) was added drop wise. The mixture was stirred at 5° C. for 1 hour, and then stirred at room temperature for 12 hours. H$_2$O was added. The mixture was extracted with CH$_2$Cl$_2$. The organic layer was separated, dried (over MgSO$_4$), filtered and the solvent was evaporated until dryness. The residue was crystallized from CH$_3$OH/2-propanone. The precipitate was filtered off and dried, yielding 0.24 g of intermediate g-5 (52%).

A mixture of g-5 (0.0001 mol) in a 5N solution of HCl in 2-propanol (0.5 ml) and 2-propanol (5 ml) was stirred at 60° C. for 4 hours, and then cooled to room temperature. The precipitate was filtered, washed with 2-propanol/diisopropylether and dried, yielding 0.058 g of 2-{2-[1-(2-Aminoethyl)-piperidin-4-ylamino]-6-styryl-benzoimidazol-1-ylmethyl}-6-methyl-pyridin-3-ol hydrochloride salt (g-6; compound 143, 63%, 3.69 HCl+3.03H$_2$O, melting point: >260° C.).

A mixture of g-5 (0.0002 mol) and Pd/C 10% (0.03 g) in CH$_3$OH (10 ml) and tetrahydrofuran (10 ml) was hydrogenated at room temperature for 4 hours under a 2 bar pressure, and then filtered over celite. Celite was washed with H$_2$O. The filtrate was evaporated until dryness, yielding 0.14 g of intermediate g-7 (100%). This product was used directly in the next reaction step.

A mixture of g-7 (0.0002 mol) in a 5N solution of HCl in 2-propanol (1.4 ml) and 2-propanol (15 ml) was stirred at 60°

C. for 4 hours, and then cooled to room temperature. The precipitate was filtered, washed with 2-propanol/diisopropylether and dried, yielding 0.138 g of g-8,2-{2-[1-(2-aminoethyl)-piperidin-4-ylamino]-6-phenethyl-benzoimidazol-1-ylmethyl}-6-methyl-pyridin-3-ol hydrochloride salt (87%, 3.62 HCl+2.41 H$_2$O, compound 140, melting point: 181° C.).

Example 8 ice water and extracted three times with CH$_2$Cl$_2$. The organic layer was separated, dried (over MgSO$_4$), filtered and the solvent was evaporated until dryness. The residue was taken up in 2-propanone/diisopropylether. The precipitate was filtered, washed with H$_2$O and dried, yielding 1 g of intermediate h-2 (82%).

Intermediate h-3 was prepared analogous to the procedure described for the preparation of g-4.

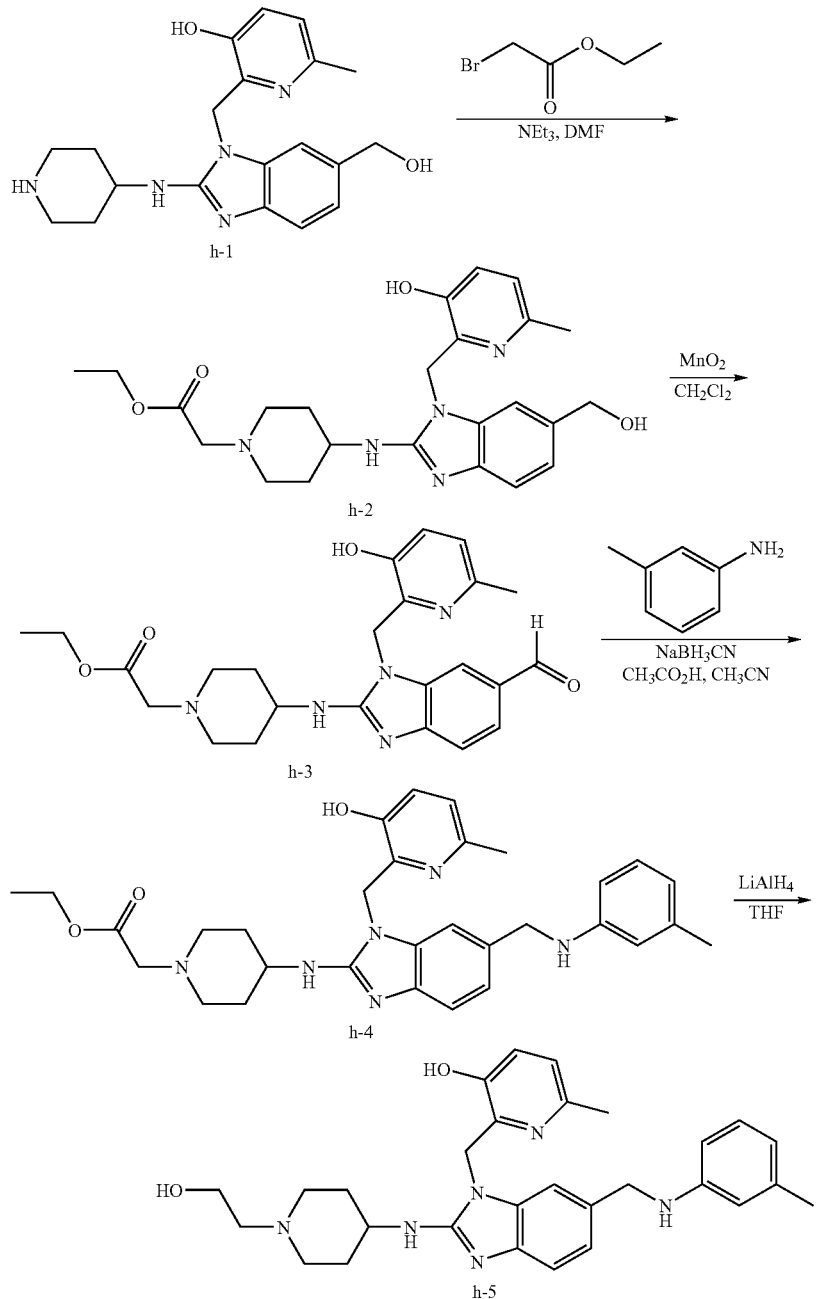

A mixture of h-1 (0.0027 mol), ethyl-bromo acetate (0.0032 mol) and triethylamine (0.004 mol) in dimethylformamide (40 ml) was stirred at 50° C. for 1 hour, poured into CH$_3$CO$_2$H (0.2 ml) was added at room temperature to a mixture of h-3 (0.0004 mol), 3-methyl-aniline (0.0005 mol) and NaBH$_3$CN (0.0005 mol) in CH$_3$CN (20 ml). The mixture was stirred at room temperature for 6 hours. CH$_3$CO$_2$H (0.2 ml) was added. The mixture was stirred at room temperature for 12 hours. The solvent was evaporated until dryness. The residue was taken up in CH$_2$Cl$_2$/K$_2$CO$_3$ 10%. The organic layer was separated, dried (over MgSO$_4$), filtered and the solvent was evaporated until dryness, yielding 0.22 g of intermediate h-4 (100%). This product was used directly in the next reaction step.

LiAlH$_4$ (0.0008 mol) was added to a mixture of h-4 (0.0004 mol) in tetrahydrofuran (20 ml) at 5° C. under N$_2$ flow. The mixture was stirred at 5° C. for 1 hour, then brought to room temperature and stirred for 4 hours. A minimum of H$_2$O and then CH$_2$Cl$_2$ were added. The organic layer was separated, dried (over MgSO$_4$), filtered and the solvent was evaporated until dryness. The residue (0.22 g) was purified by column chromatography over silica gel (eluent: CH$_2$Cl$_2$/CH$_3$OH/ NH$_4$OH 85/15/1; 15-40 μm). The pure fractions were collected and the solvent was evaporated. The residue (0.1 g, 50%) was crystallized from CH$_3$OH/CH$_3$CN/diisopropylether. The precipitate was filtered off and dried, yielding 0.08 g of 2-[2-[1-(2-hydroxy-ethyl)-piperidin-4-ylamino]-6-(m-tolyl-amino-methyl)-benzoimidazol-1-ylmethyl]-6-methyl-pyridin-3-ol (40%, compound 145, melting point: 137° C.).

Example 9

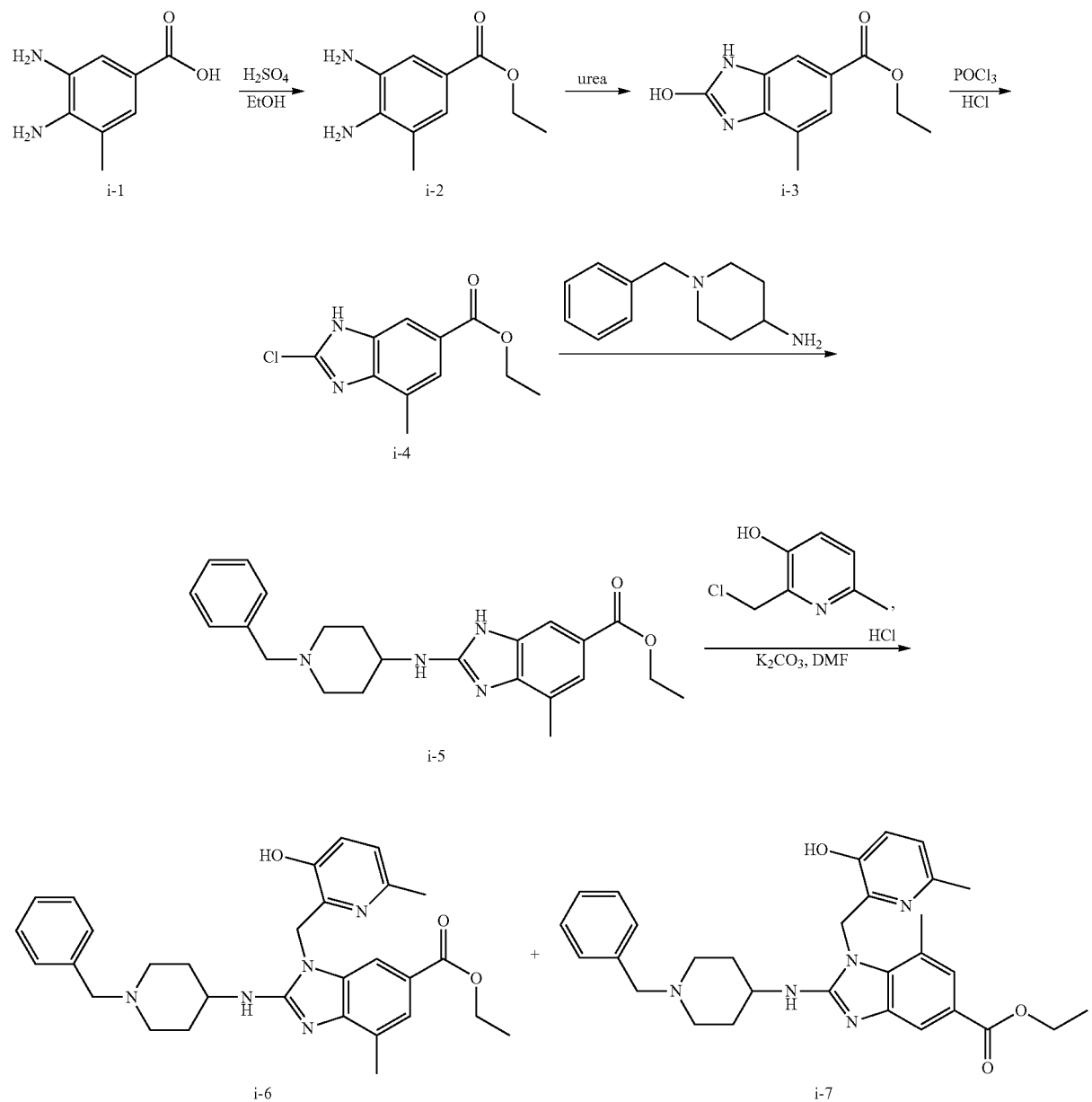

Scheme I

-continued
i-6 →(LiAlH4, THF)→ 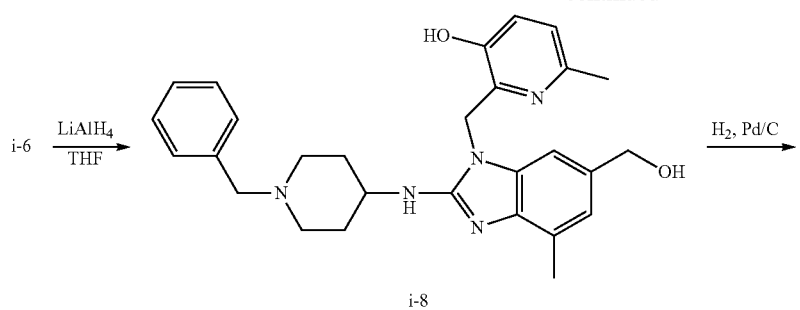
→(H2, Pd/C)→ 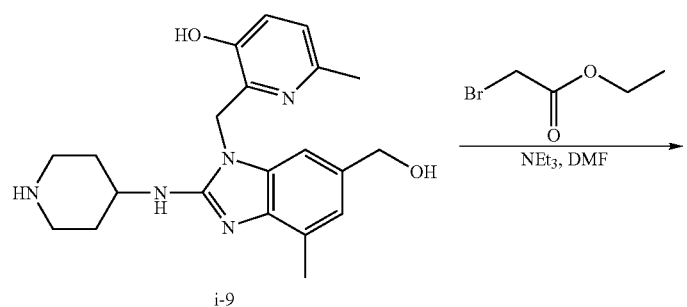
→(ethyl bromoacetate, NEt3, DMF)→ 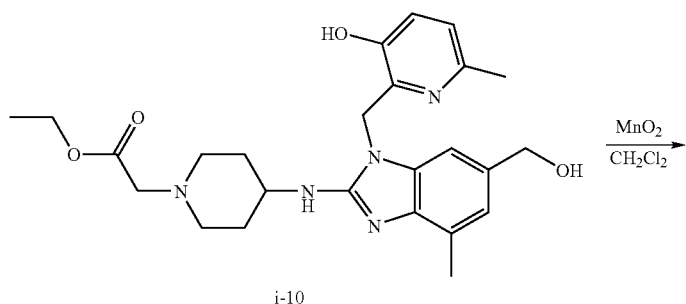
→(MnO2, CH2Cl2)→ 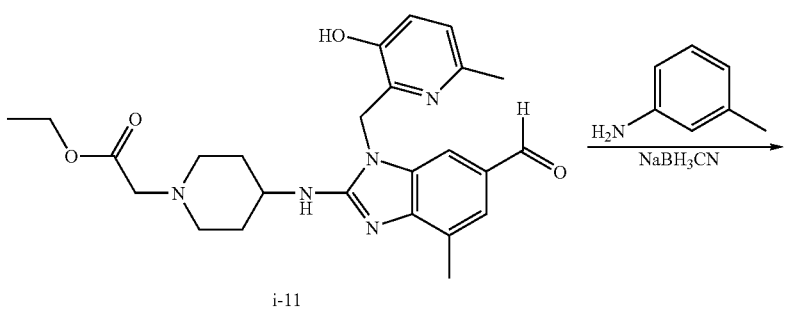
→(m-toluidine H2N-, NaBH3CN)→ 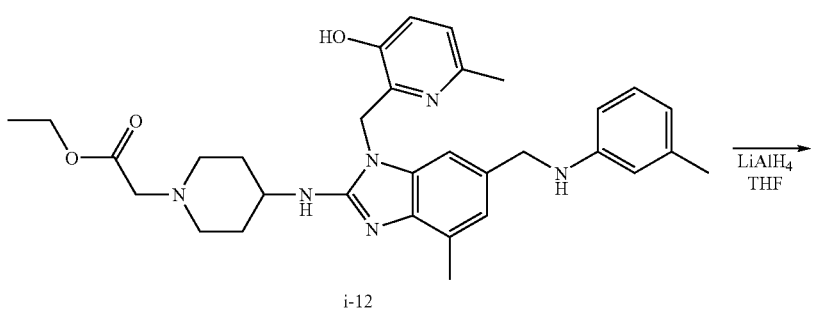
→(LiAlH4, THF)→

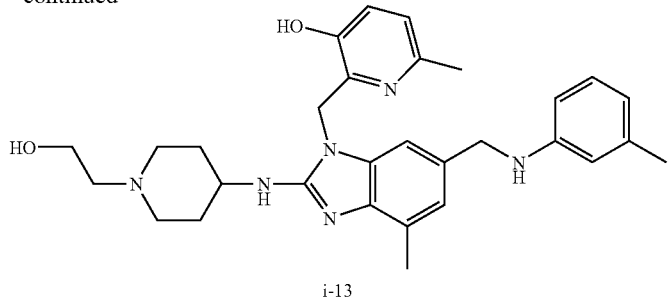

i-13

A mixture of i-1 (0.0185 mol) in ethanol (60 ml) and H$_2$SO$_4$ 36N (5 ml) was stirred and refluxed for 24 hours. The solvent was evaporated until dryness. The residue was taken up in CH$_2$Cl$_2$. The organic layer was washed with a 10% solution K$_2$CO$_3$ in water, dried (over MgSO$_4$), filtered and the solvent was evaporated until dryness, yielding 3.2 g of intermediate i-2 (89%).

Intermediate i-3 was prepared in an analogous way to the procedure described for intermediate a-2. Intermediate i-4 was prepared in an analogous way to the procedure described for intermediate a-3. Intermediate i-5 was prepared in an analogous way to the procedure described for intermediate a-5.

A mixture of i-5 (0.0048 mol), 2-chloromethyl-6-methyl-3-pyridinol (0.0058 mol) and K$_2$CO$_3$ (0.0192 mol) in dimethylformamide (20 ml) was stirred at room temperature for 12 hours, poured into ice water and extracted with CH$_2$Cl$_2$. The organic layer was separated, dried (over MgSO$_4$), filtered and the solvent was evaporated until dryness. The residue (3.4 g) was purified by column chromatography over silica gel (eluent: toluene/2-propanol/NH$_4$OH 83/16/1; 15-35 μm). Two fractions were collected and the solvent was evaporated, yielding 0.9 g of intermediate i-6 (37%) and 0.78 g of intermediate i-7 (32%).

Intermediate i-8 was prepared in an analogous way to the procedure described for intermediate a-9. Intermediate i-9 was prepared in an analogous way to the procedure described for intermediate a-11. Intermediate i-10 (melting point: 221° C.) was prepared in an analogous way to the procedure described for intermediate h-2. Intermediate i-11 was prepared in an analogous way to the procedure described for intermediate h-3. Intermediate i-12 (melting point: 143° C.) was prepared in an analogous way to the procedure described for intermediate h-4.

2-[2-[1-(2-Hydroxy-ethyl)-piperidin-4-ylamino]-4-methyl-6-(m-tolylamino-methyl)-benzoimidazol-1-ylmethyl]-6-methyl-pyridin-3-ol (i-13, compound 168, melting point: 123° C.) was prepared in an analogous way to the procedure described for compound h-5.

Example 10

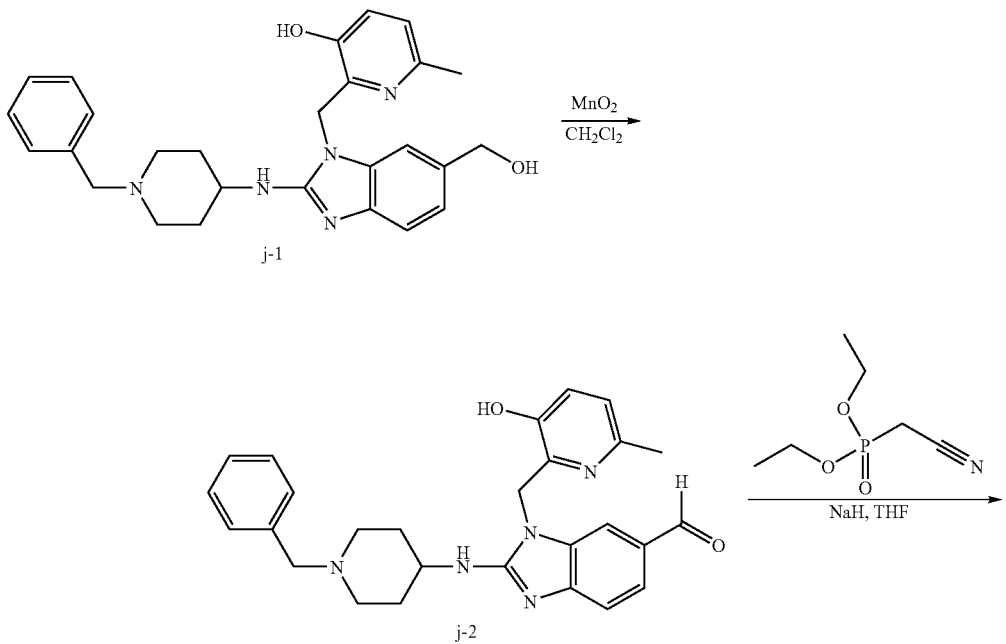

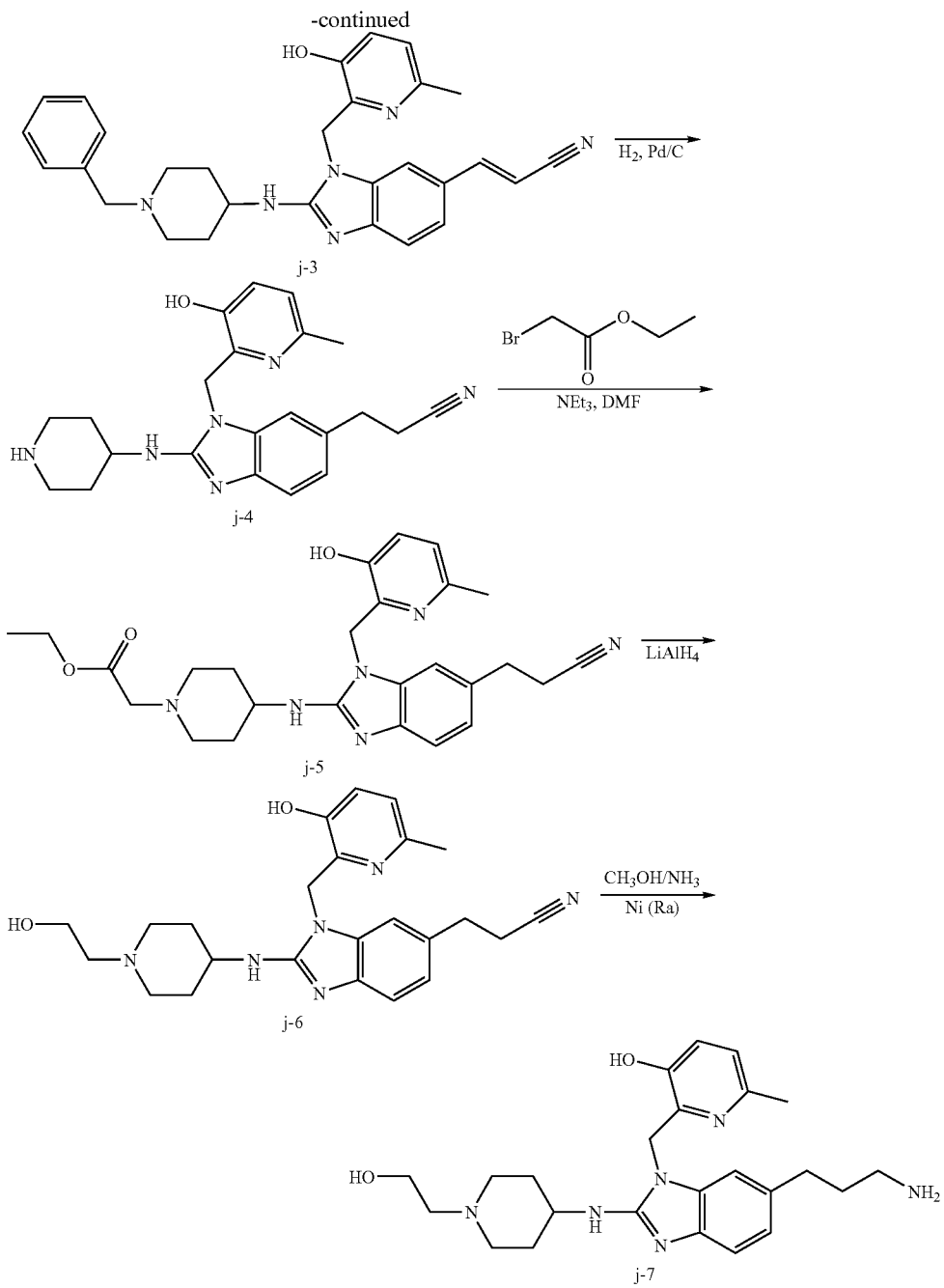

Intermediate j-2 was prepared in an analogous way to the procedure described for intermediate h-3.

Diethyl cyanomethyl phosphonate (0.0052 mol) was added to a mixture of NaH (0.0105 mol) in tetrahydrofuran (30 ml) at 5° C. under $N_2$ flow. The mixture was stirred at 5° C. for 30 minutes. A solution of j-2 (0.0017 mol) in tetrahydrofuran (20 ml) was then added. The mixture was stirred at 5° C. for 1 hour, and then stirred at room temperature for 12 hours. $H_2O$ was added. The mixture was extracted with $CH_2Cl_2$. The organic layer was separated, dried (over $MgSO_4$), filtered and the solvent was evaporated until dryness. The residue was purified by column chromatography over silica gel (eluent: $CH_2Cl_2/CH_3OH/NH_4OH$ 95/5/0.1; 70-200 μm). The pure fractions were collected and the solvent was evaporated, yielding 0.7 g of intermediate j-3 (84%).

A mixture of j-3 (0.0014 mol) and Pd/C 10% (0.25 g) in $CH_3OH$ (35 ml) was hydrogenated at 40° C. for 6 hours under an 8 bar pressure, then cooled to room temperature and filtered over celite. The filtrate was evaporated until dryness, yielding 0.3 g of intermediate j-4 (52%).

Intermediate j-5 was prepared in an analogous way to the procedure described for intermediate h-2. Intermediate j-6 (melting point: 207° C.) was prepared in an analogous way to the procedure described for intermediate i-13.

A mixture of j-6 (0.0003 mol) and Raney Nickel (0.2 g) in a saturated solution of $NH_3$ in $CH_3OH$ (25 ml) was hydrogenated at room temperature for 1 hour, and then filtered over celite. The filtrate was evaporated until dryness. The residue (0.22 g) was purified by column chromatography over silica gel (eluent: CH$_2$Cl$_2$/CH$_3$OH/NH$_4$OH 80/20/2; 10 μm). The pure fractions were collected and the solvent was evaporated. The residue (0.083 g, 49%) was dissolved in ethanol/2-propanone and converted into the hydrochloric acid salt. The precipitate was filtered off and dried. The residue was crystallized from diisopropylether. The precipitate was filtered off and dried, yielding 0.08 g of 2-{6-(3-Amino-propyl)-2-[1-(2-hydroxy-ethyl)-piperidin-4-ylamino]-benzoimidazol-1-ylmethyl}-6-methyl-pyridin-3-ol hydrochloride salt (36%, 3.6 HCl, compound 157, melting point: 185° C.).

Example 11

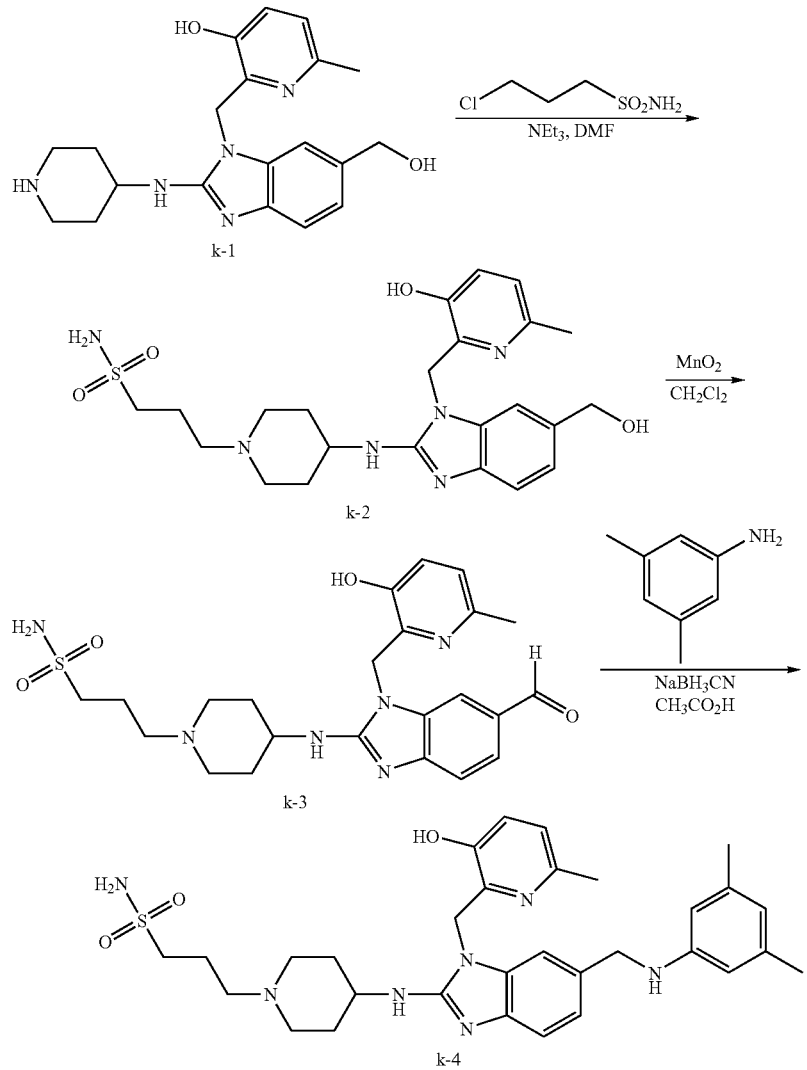

NH$_4$OH 85/15/2; 15-40 μm). The pure fractions were collected and the solvent was evaporated, yielding 0.336 g of intermediate k-2 (36%).

A mixture of k-2 (0.0007 mol) and MnO$_2$ (1 g) in CH$_2$Cl$_2$ (30 ml) was stirred at room temperature for 6 hours, and then filtered over celite. Celite was washed with H$_2$O. The solvent of the filtrate was evaporated until dryness, yielding 0.33 g of intermediate k-3 (100%). This product was used directly in the next reaction step.

CH$_3$CO$_2$H (0.2 ml) was added at room temperature to a mixture of k-3 (0.0004 mol), 3,5-dimethyl-aniline (0.0005 mol) and NaBH$_3$CN (0.0005 mol) in CH$_3$CN (20 ml). The mixture was stirred at room temperature for 30 minutes.

A mixture of k-1 (0.0019 mol), 3-chloro-propylsulfonamide (0.0022 mol) and triethylamine (0.0028 mol) in dimethylformamide (50 ml) was stirred at 70° C. for 48 hours, poured into ice water, saturated with K$_2$CO$_3$ (powder) and extracted with CH$_2$Cl$_2$. The organic layer was separated, dried (over MgSO$_4$), filtered and the solvent was evaporated until dryness. The residue (1.5 g) was purified by column chromatography over silica gel (eluent: CH$_2$Cl$_2$/CH$_3$OH/

CH$_3$CO$_2$H (0.2 ml) was added. The mixture was stirred at room temperature for 12 hours. The solvent was evaporated until dryness. The residue was taken up in CH$_2$Cl$_2$. The organic layer was washed with a 10% solution of K$_2$CO$_3$ in water, dried (over MgSO$_4$), filtered and the solvent was evaporated until dryness. The residue (0.26 g) was purified by column chromatography over silica gel (eluent: CH$_2$Cl$_2$/CH$_3$OH/NH$_4$OH 90/10/1; 5 μm). The pure fractions were collected and the solvent was evaporated, yielding 0.09 g (32%). This fraction was crystallized from CH₃CN/diisopropylether. The precipitate was filtered off and dried, yielding 0.083 g of 2-{4-[6-[(3,5-Dimethyl-phenylamino)-methyl]-1-(3-hydroxy-6-methyl-pyridin-2-ylmethyl)-1H-benzoimidazol-2-ylamino]-piperidin-1-yl}-ethane-sulfonic acid amide (30%, compound 147, melting point: 142° C.).

Example 12

Intermediate 1-2 (melting point: 210° C.) was prepared in an analogous way to the procedure described for intermediate k-2. Intermediate 1-3 was prepared in an analogous way to the procedure described for intermediate k-3. Intermediate 1-4 was prepared in an analogous way to the procedure described for compound k-4.

A mixture of 1-4 (0.0003 mol) in a 7N solution of NH₃ in CH₃OH (15 ml) was stirred at 80° C. for 12 hours. The solvent was evaporated until dryness. The residue (0.21 g) was purified by column chromatography over silica gel (eluent:

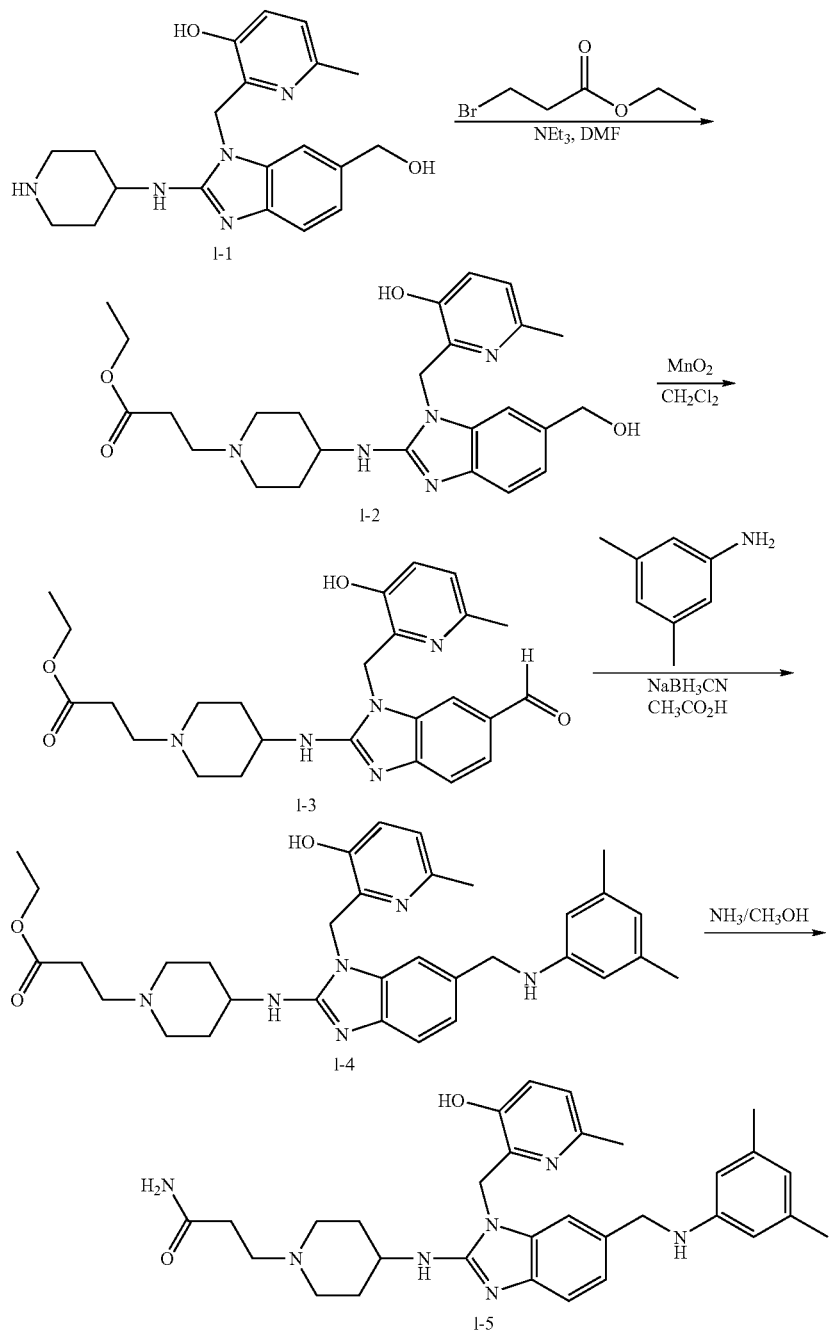

Scheme L $CH_2Cl_2/CH_3OH/NH_4OH$ 85/14/1; 10 µm). The pure fractions were collected and the solvent was evaporated. The residue (0.057 g, 30%) was crystallized from 2-propanone/$CH_3CN$/diisopropylether. The precipitate was filtered off and dried, yielding 0.05 g of 2-{4-[6-[(3,5-dimethyl-phenylamino)-methyl]-1-(3-hydroxy-6-methyl-pyridin-2-ylmethyl)-1H-benzoimidazol-2-ylamino]-piperidin-1-yl}-acetamide (26%, compound 148, melting point: 206° C.).

Example 13

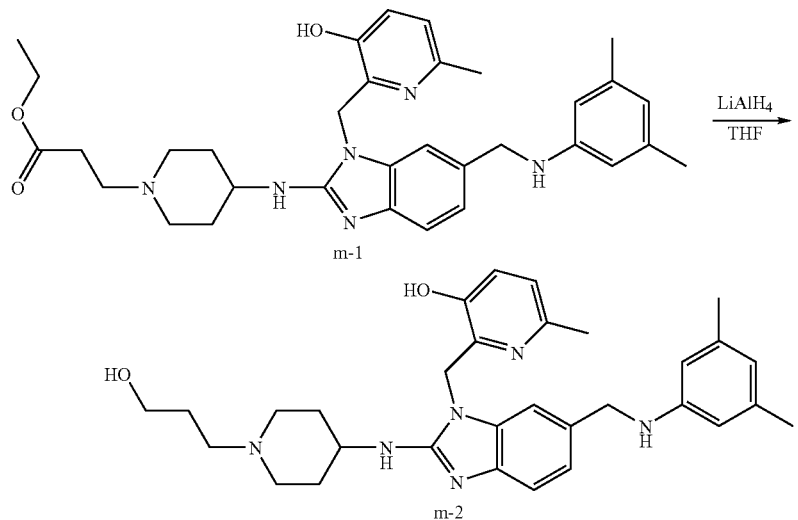

A mixture of m-1 (0.0002 mol) in tetrahydrofuran (30 ml) was cooled to 5° C. under $N_2$ flow. $LiAlH_4$ (0.0007 mol) was added. The mixture was stirred at 5° C. for 1 hour, and then stirred at room temperature for 1 hour. A minimum of $H_2O$ was added. $CH_2Cl_2$ was added. The organic layer was separated, dried (over $MgSO_4$), filtered and the solvent was evaporated until dryness. The residue (0.16 g) was purified by column chromatography over silica gel (eluent: $CH_2Cl_2$/$CH_3OH/NH_4OH$ 85/15/1; 10 µm). The pure fractions were collected and the solvent was evaporated. The residue (0.073 g, 53%) was crystallized from 2-propanone/$CH_3CN$/diisopropylether. The precipitate was filtered off and dried, yielding 0.064 g of 2-{6-[(3,5-dimethyl-phenylamino)-methyl]-2-[1-(2-hydroxy-ethyl)-piperidin-4-ylamino]-benzoimidazol-1-ylmethyl}-6-methyl-pyridin-3-ol (m2, 46%, compound 149, melting point: 144° C.).

Example 14

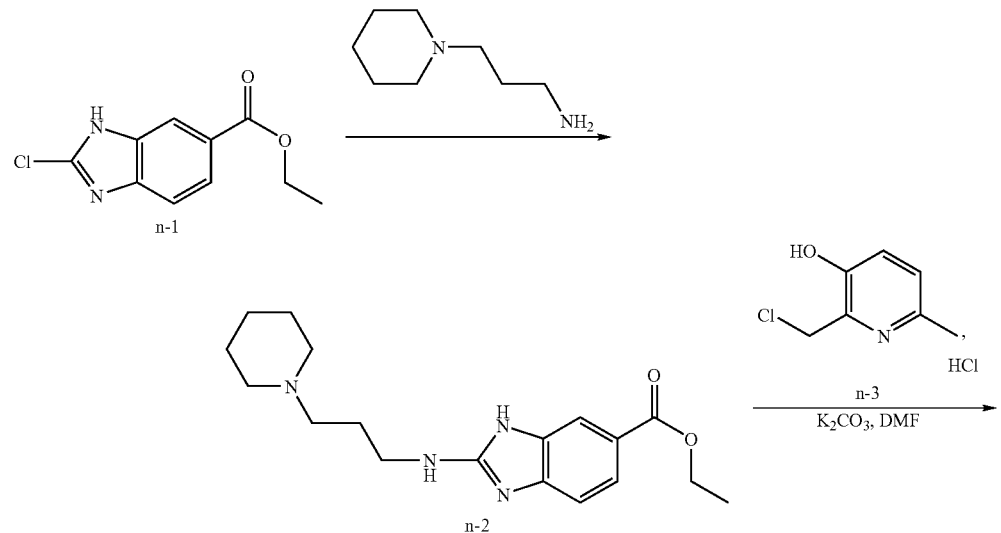

-continued

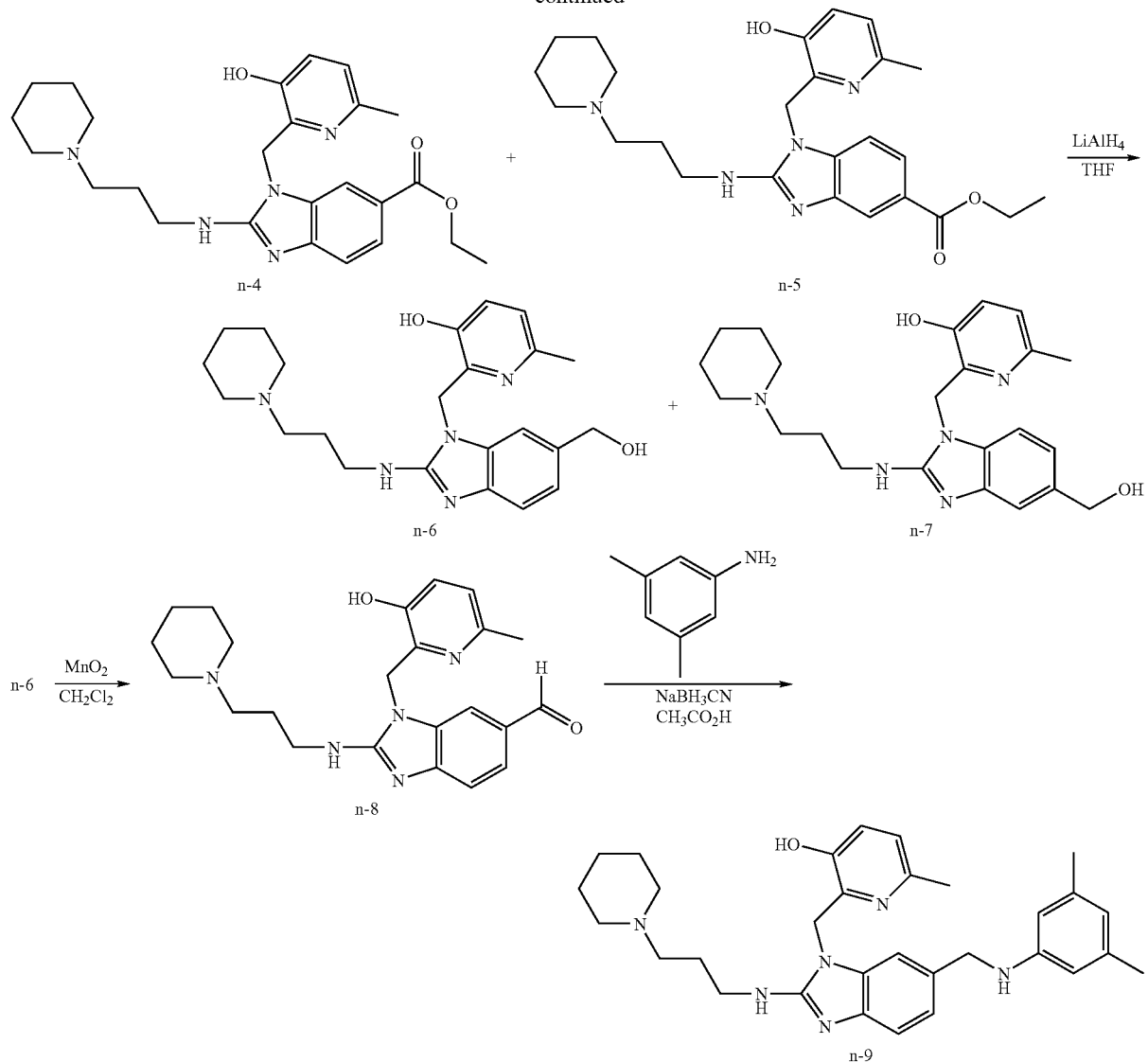

A mixture of n-1 (0.022 mol) and N-(propylamino)-piperidine (0.0207 mol) was stirred at 140° C. for 1 hour, and then taken up in CH$_2$Cl$_2$/CH$_3$OH. The organic layer was washed with K$_2$CO$_3$ 10%, dried (over MgSO$_4$), filtered and the solvent was evaporated until dryness. The residue was purified by column chromatography over silica gel (eluent: CH$_2$Cl$_2$/CH$_3$OH/NH$_4$OH 92/8/1; 70-200 μm). The pure fractions were collected and the solvent was evaporated, yielding 2.2 g of intermediate n-2 (30%).

A mixture of n-2 (0.0066 mol), n-3 (0.0073 mol) and K$_2$CO$_3$ (0.02 mol) in dimethylformamide (25 ml) was stirred at room temperature for 24 hours, poured into H$_2$O and extracted with CH$_2$Cl$_2$. The organic layer was separated, dried (over MgSO$_4$), filtered and the solvent was evaporated until dryness. The residue was taken up in CH$_3$CN/diisopropylether. The precipitate was filtered, washed with H$_2$O and dried, yielding 1.8 g of the mixture of intermediates n-4 and n-5 (61%).

LiAlH$_4$ (0.012 mol) was added portion wise to a mixture of n-4 (0.002 mol) and n-5 (0.002 mol) in tetrahydrofuran (60 ml) at 5° C. under N$_2$ flow. The mixture was stirred at 5° C. for 1 hour, then at room temperature for 12 hours. A minimum of H$_2$O was added. A solution of CH$_2$Cl$_2$/CH$_3$OH (90/10) was added. The organic layer was separated, dried (over MgSO$_4$), filtered and the solvent was evaporated until dryness. The residue (1.65 g) was purified by column chromatography over silica gel (eluent: CH$_2$Cl$_2$/CH$_3$OH/NH$_4$OH 80/20/3; 15-40 μm). Two fractions were collected and the solvent was evaporated, yielding 0.35 g of fraction 1 and 0.049 g of fraction 2. Fraction 1 was crystallized from 2-propanone/diisopropylether. The precipitate was filtered off and dried, yielding 0.33 g of intermediate n-6 (19%, melting point: 220° C.). Fraction 2 was crystallized from 2-propanone/diisopropylether. The precipitate was filtered off and dried, yielding 0.43 g of intermediate n-7 (26%, melting point: 146° C.).

A mixture of n-6 (0.0006 mol) and MnO$_2$ (0.5 g) in CH$_2$Cl$_2$ (30 ml) was stirred at room temperature for 12 hours, and then filtered over celite. Celite was washed with H$_2$O. The filtrate was evaporated until dryness, yielding 0.26 g of intermediate n-8 (100%). The compound was used directly in the next reaction step.

CH$_3$CO$_2$H (0.3 ml) was added to a mixture of n-8 (0.0006 mol), 3,5-dimethyl-aniline (0.0007 mol) and NaBH$_3$CN (0.0007 mol) in CH$_3$CN (30 ml). The mixture was stirred at room temperature for 30 minutes. CH$_3$CO$_2$H (0.3 ml) was added. The mixture was stirred at room temperature for 24 hours. The solvent was evaporated until dryness. The residue was taken up in 2-propanone/HCl 5N/ethanol. The mixture was stirred at 80° C. for 12 hours. The solvent was evaporated until dryness. The mixture was extracted with CH$_2$Cl$_2$. The organic layer was separated, dried (over MgSO$_4$), filtered and the solvent was evaporated until dryness. The residue (0.39 g) was purified by column chromatography over silica gel (eluent: CH$_2$Cl$_2$/CH$_3$OH/NH$_4$OH 90/10/0.5; 10 µm). The pure fractions were collected and the solvent was evaporated. The residue (0.119 g, 59%) was taken up in CH$_3$CN/diisopropylether. The precipitate was filtered off and dried, yielding 0.17 g of 2-[6-[(3,5-dimethyl-phenylamino)-methyl]-2-(3-piperidin-1-yl-propylamino)-benzoimidazol-1-ylmethyl]-6-methyl-pyridin-3-ol (n-9, 53%, compound 170, melting point: 161° C.).

Example 15

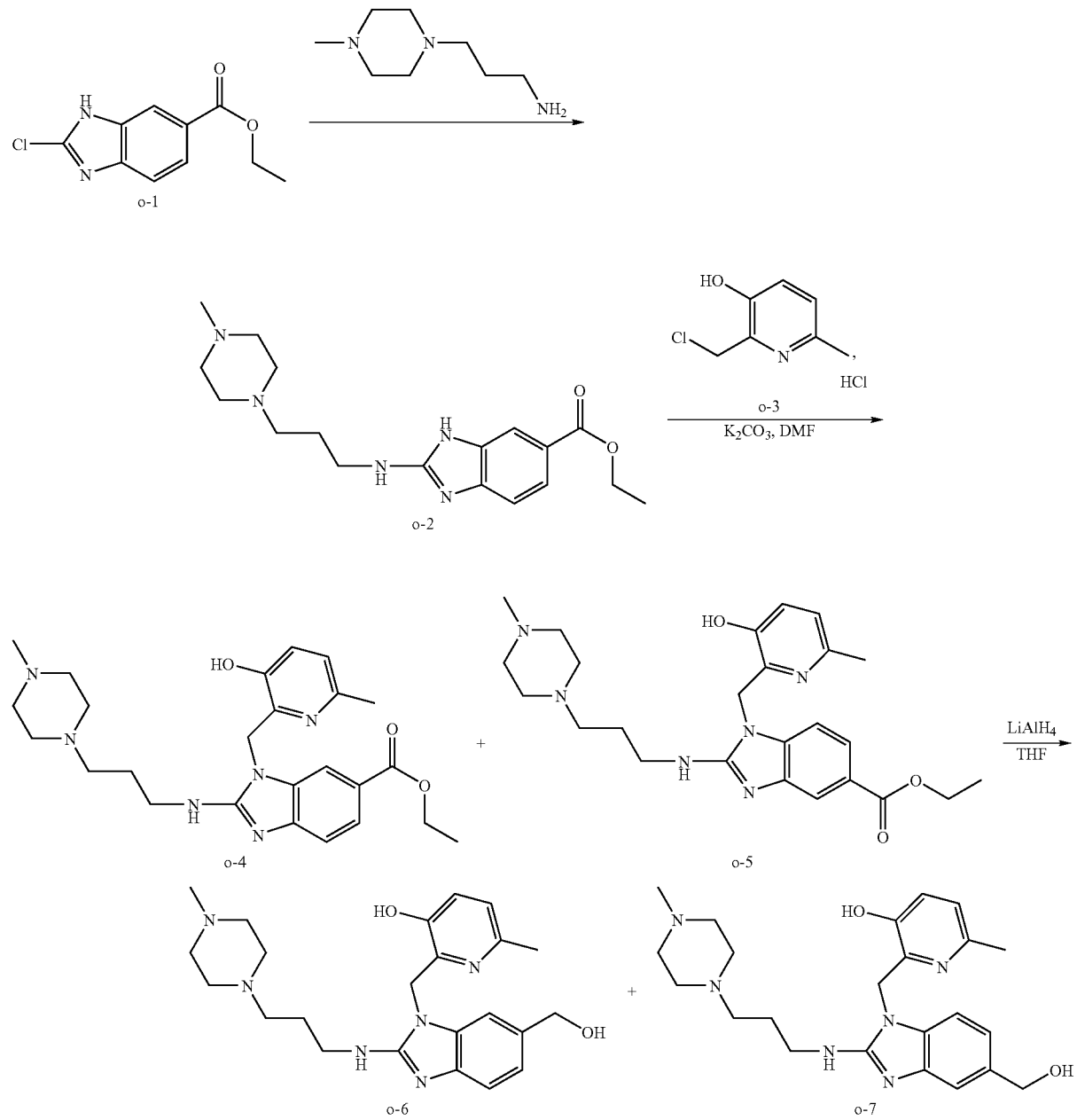

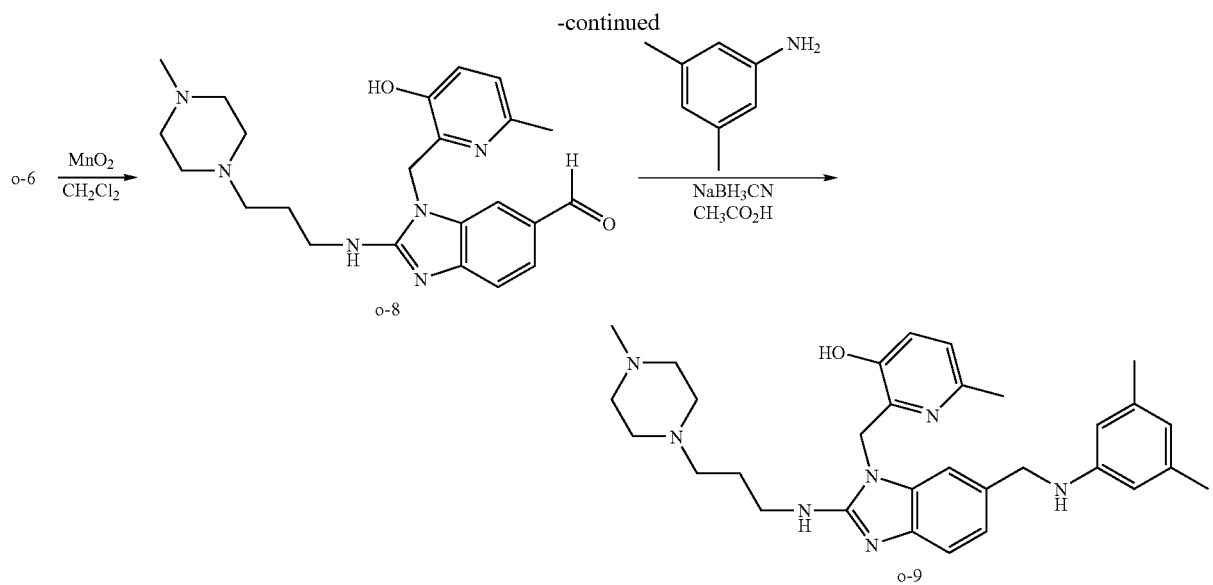
2-{6-[(3,5-Dimethyl-phenylamino)-methyl]-2-[3-(4-methyl-piperazin-1-yl)-propylamino]-benzoimidazol-1-ylmethyl}-6-methyl-pyridin-3-ol (compound 171, melting point: 150° C.) and its intermediates were prepared in an analogous way to the procedures described for preparing compound n-9.
Example 16
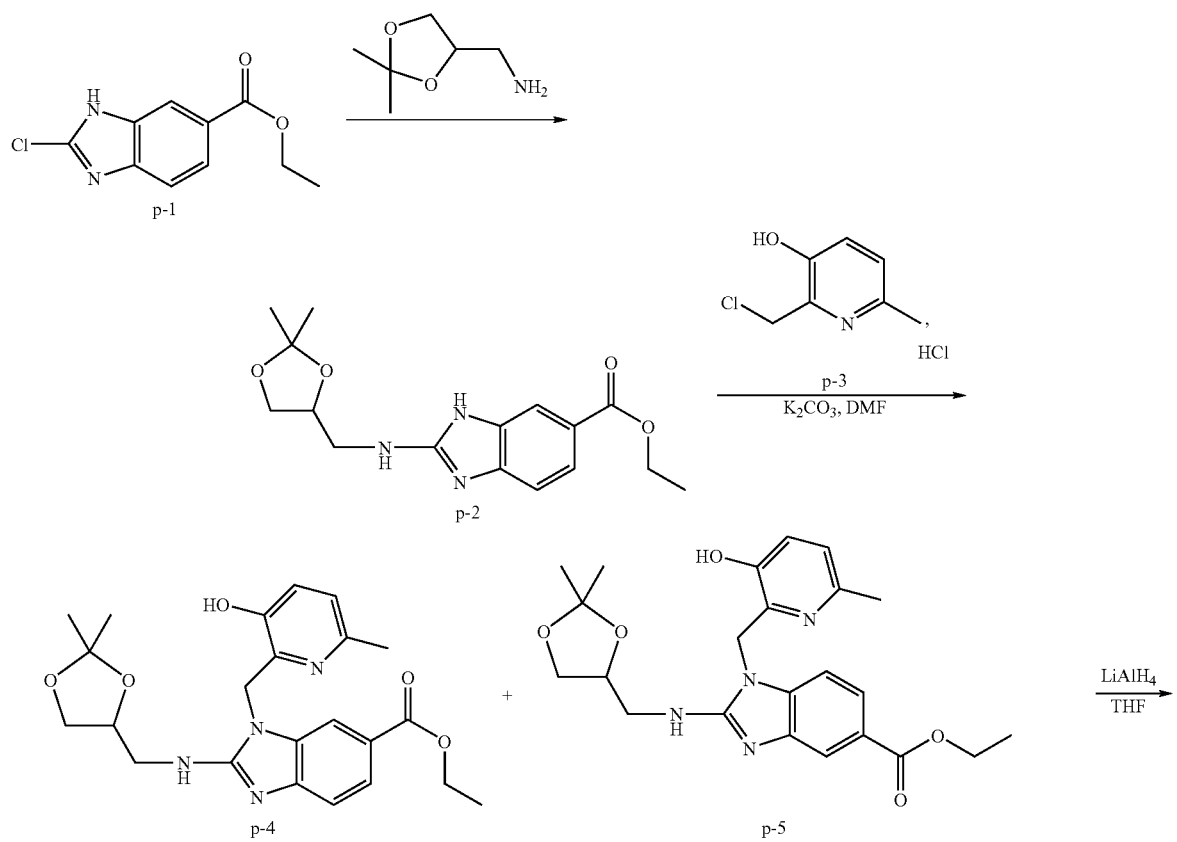

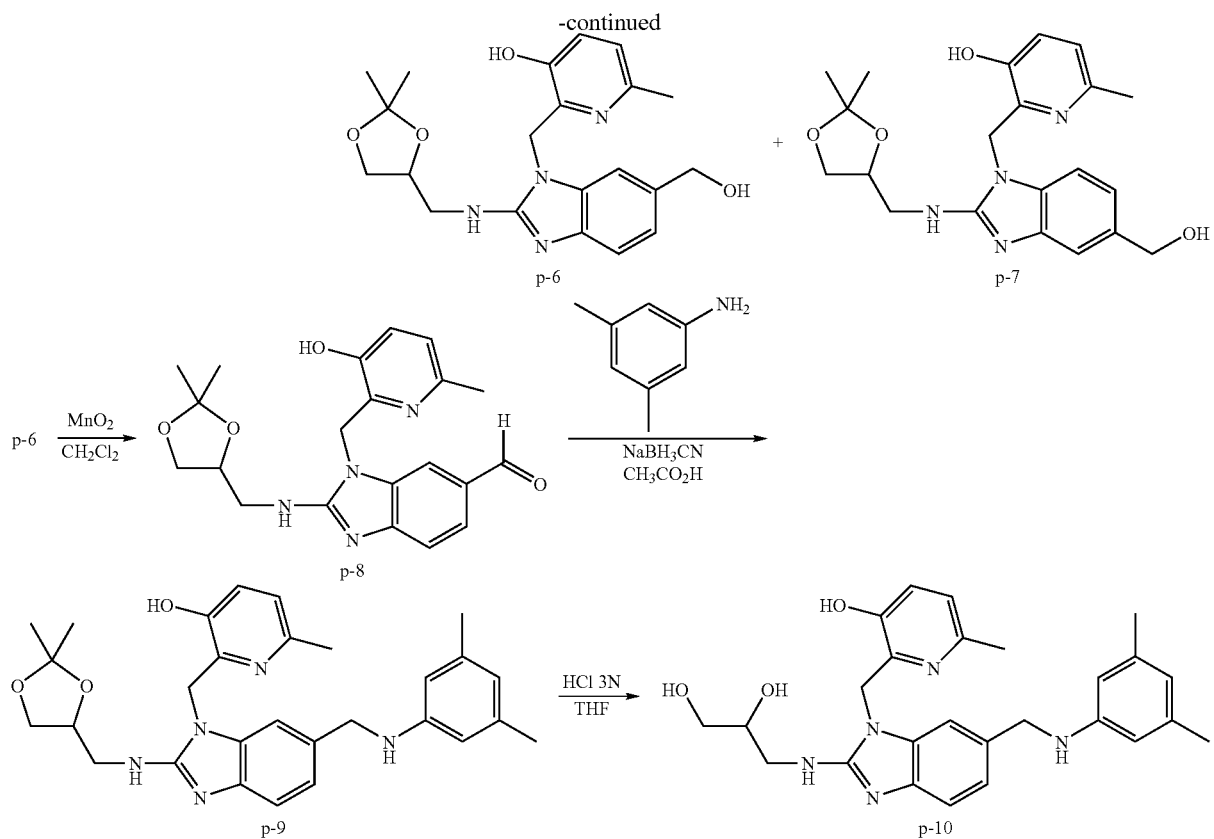

Intermediate p-9 (melting point: 212° C.) was prepared in an analogous way to the procedure described for compound n-9.

A mixture of p-9 (0.0004 mol) in a 3N solution of HCl in water (20 ml) and tetrahydrofuran (20 ml) was stirred at room temperature for 6 hours, basified with $K_2CO_3$ (powder) and extracted with $CH_2Cl_2$. The organic layer was separated, dried (over $MgSO_4$), filtered and the solvent was evaporated until dryness. The residue (0.25 g) was purified by column chromatography over silica gel (eluent: $CH_2Cl_2/CH_3OH/$ $NH_4OH$ 92/8/0.5; 10 μm). The pure fractions were collected and the solvent was evaporated. The residue (0.17 g, 92%) was crystallized from $CH_3CN$/diisopropylether. The precipitate was filtered off and dried, yielding 0.127 g of 3-[6-[(3,5-dimethyl-phenylamino)methyl]-1-(3-hydroxy-6-methyl-pyridin-2-ylmethyl)-1H-benzoimidazol-2-ylamino]-propane-1,2-diol (p-10, 69%, compound 172, melting point: 128° C.).

Example 17

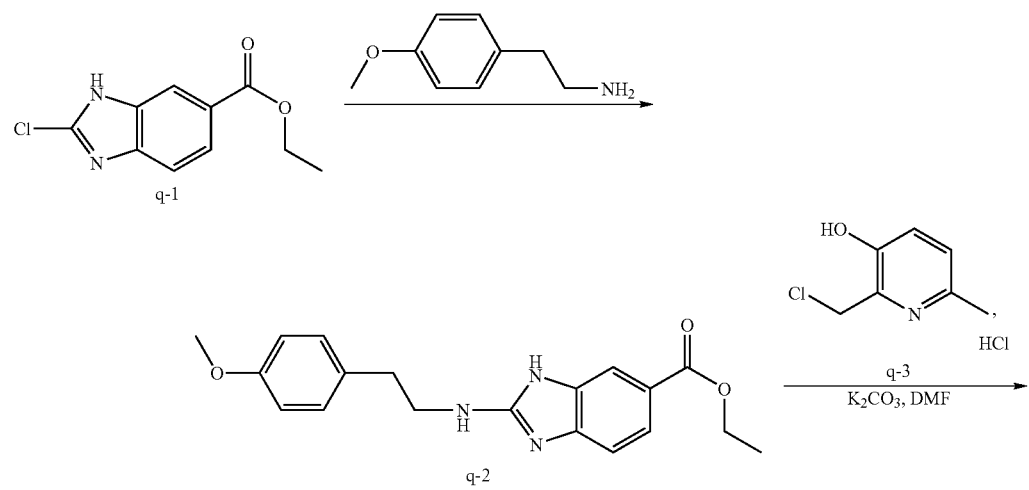

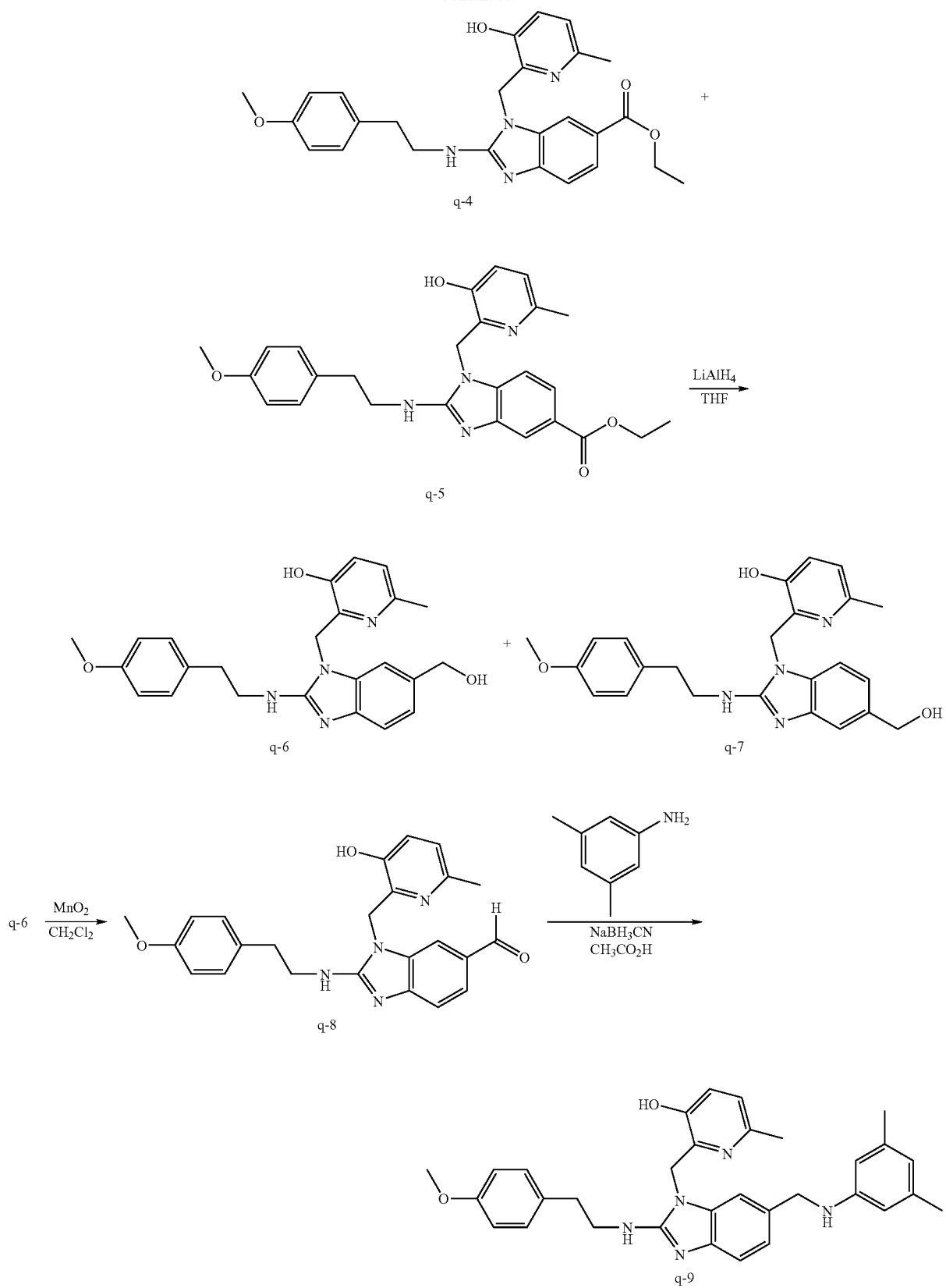
-continued

2-{6-[(3,5-Dimethyl-phenylamino)-methyl]-2-[2-(4-methoxy-phenyl)-ethylamino]-benzoimidazol-1-ylmethyl}-6-methyl-pyridin-3-ol (compound 187, melting point: 178° C.) and its intermediates were prepared in an analogous way to the procedures described for preparing compound n-9.

The following tables list compounds that were prepared according to any one of the above examples.

TABLE 1

| Comp. No. | R2b | R2a | Activity | Mass (MH+) | Melting point/salt | Synthesis scheme |
|---|---|---|---|---|---|---|
| 1 | H | 3,5-dimethylphenyl-N(ethyl)(CH2CH2OH) | 9.4 | 529 | 201° C. | A |
| 2 | H | 3,5-dichlorophenyl-NH(ethyl) | 8.7 | 525 | — | B Variant 1 |
| 3 | H | 3,5-dimethylphenyl-NH(ethyl) | 8.6 | 485 | — | B Variant 1 |
| 4 | H | phenyl-N(ethyl)(CH2CH2OH) | 8.5 | 501 | 229° C. | A |
| 5 | H | 3,5-dimethylphenyl-N(ethyl)(CH2CH2N(CH3)2) | 8.5 | 556 | 199° C. | A |

TABLE 1-continued

[Structure: benzimidazole core with N-methylpiperidin-4-ylamino group, (3-hydroxy-6-methylpyridin-2-yl)methyl N-substituent, and R2a/R2b substituents]

| Comp. No. | R2b | R2a | Activity | Mass (MH+) | Melting point/salt | Synthesis scheme |
|---|---|---|---|---|---|---|
| 6 | H | 3-Br-C6H4-NH-CH2CH3 | 8.4 | 535 | — | B Variant 1 |
| 7 | H | 2-(HOCH2)-C6H4-NH-CH2CH3 | 8.4 | 487 | — | B Variant 1 |
| 8 | H | 2-(CH3CH2)-C6H4-NH-CH2CH3 | 8.4 | 485 | — | B Variant 1 |
| 9 | H | 3-CH3-C6H4-NH-CH2CH3 | 8.3 | 471 | 141° C. | B Variant 2 |
| 10 | H | 4-(H2NSO2)-C6H4-NH-CH2CH3 | 8.3 | 536 | — | B Variant 1 |
| 11 | H | 3-Cl-C6H4-NH-CH2CH3 | 8.2 | 491 | — | B Variant 1 |
| 12 | H | 4-CN-C6H4-NH-CH2CH3 | 8.2 | 482 | — | B Variant 1 |
| 13 | H | 3-(HC≡C)-C6H4-NH-CH2CH3 | 8.1 | 481 | — | B Variant 1 |

TABLE 1-continued

| Comp. No. | R2b | R2a | Activity | Mass (MH+) | Melting point/salt | Synthesis scheme |
|---|---|---|---|---|---|---|
| 14 | H | 2-(ethylamino)benzamide | 8.1 | 500 | — | B Variant 1 |
| 15 | H | N-ethyl-3-ethylaniline | 8 | 485 | 150° C. | B Variant 2 |
| 16 | H | 4-(N-ethyl-N-phenylamino)phenol | 8 | 549 | 176° C. | A |
| 17 | H | 1-(4-(ethylamino)phenyl)ethanone | 8 | 499 | — | B Variant 1 |
| 18 | H | N-ethyl-3-fluoroaniline | 7.9 | 475 | 130° C. | B Variant 2 |
| 19 | H | 1-(3-(ethylamino)phenyl)ethanone | 7.9 | 499 | — | B Variant 1 |
| 20 | H | N-ethyl-2,3-dimethylaniline | 7.9 | 485 | — | B Variant 1 |

TABLE 1-continued
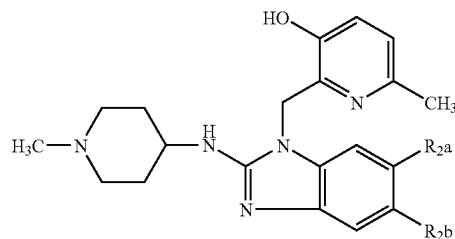
| Comp. No. | R2b | R2a | Activity | Mass (MH+) | Melting point/salt | Synthesis scheme |
|---|---|---|---|---|---|---|
| 21 | H | (2-isopropyl-N-ethylaniline) | 7.9 | 499 | — | B Variant 1 |
| 22 | H | (2-bromo-N-ethylaniline) | 7.9 | 535 | — | B Variant 1 |
| 23 | H | (2-fluoro-N-ethylaniline) | 7.9 | 475 | — | B Variant 1 |
| 24 | H | (ethyl 4-ethylamino-3-hydroxybenzoate) | 7.9 | 545 | — | B Variant 1 |
| 25 | H | (3-methylthio-N-ethylaniline) | 7.9 | 503 | — | B Variant 1 |
| 26 | H | (4-fluoro-N-ethylaniline) | 7.9 | 475 | — | B Variant 1 |
| 27 | H | (4-chloro-N-ethyl-N-(1H-imidazol-5-ylmethyl)aniline) | 7.9 | 571 | 197° C. | A |

TABLE 1-continued
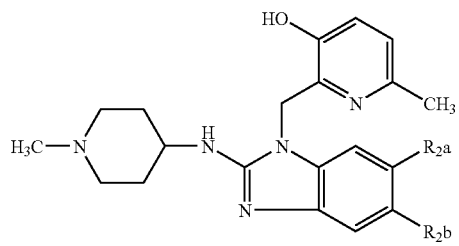
| Comp. No. | R2b | R2a | Activity | Mass (MH+) | Melting point/salt | Synthesis scheme |
|---|---|---|---|---|---|---|
| 28 | H | 3-methylbenzyl-N(CH3)- | 7.8 | 471 | 240° C. | F |
| 29 | H | 3-phenylpropyl | 7.8 | 456 | 232° C. | G |
| 30 | H | N-ethyl-phenylamino | 7.8 | 457 | 206 | B Variant 2 |
| 31 | H | 8-(N-ethylamino)quinoline | 7.8 | 508 | — | B Variant 1 |
| 32 | H | 6-(N-ethylamino)-2,3-dihydro-1,4-benzodioxine | 7.8 | 515 | — | B Variant 1 |
| 33 | H | 4-methoxy-N-ethyl-phenylamino | 7.8 | 487 | — | B Variant 1 |
| 34 | H | 4-(N-ethylamino)phenylacetonitrile | 7.8 | 496 | — | B Variant 1 |
| 35 | H | 3-(3-methylphenyl)propyl | 7.7 | 470 | — | G |

TABLE 1-continued
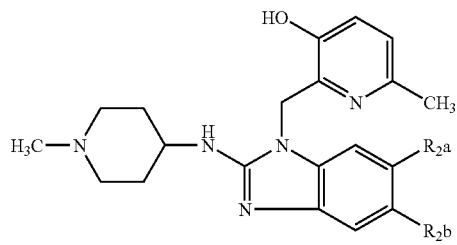
| Comp. No. | R2b | R2a | Activity | Mass (MH+) | Melting point/salt | Synthesis scheme |
|---|---|---|---|---|---|---|
| 36 | H | 3,5-dimethoxy-N-ethylaniline | 7.7 | 517 | — | B Variant 1 |
| 37 | H | 4-methyl-N-ethylaniline | 7.7 | 471 | — | B Variant 1 |
| 38 | H | 4-bromo-N-ethylaniline | 7.7 | 535 | — | B Variant 1 |
| 39 | H | N-ethyl-N-phenylglycine | 7.7 | 515 | | A |
| 40 | H | 3-chloro-2-methyl-N-ethylaniline | 7.6 | 505 | — | B Variant 1 |
| 41 | H | 3,4-dimethyl-N-ethylaniline | 7.6 | 485 | — | B Variant 1 |
| 42 | H | N-ethyl-2-biphenylamine | 7.6 | 533 | — | B Variant 1 |

TABLE 1-continued

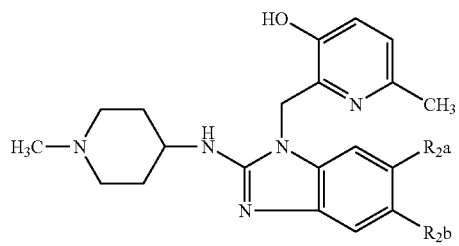

| Comp. No. | R2b | R2a | Activity | Mass (MH+) | Melting point/salt | Synthesis scheme |
|---|---|---|---|---|---|---|
| 43 | H | 3-ethyl-4-(ethylamino)benzonitrile | 7.6 | 510 | — | B Variant 1 |
| 44 | H | butylamine (NH2-propyl chain) | 7.5 | 409 | — | J |
| 45 | H | N-ethyl-2,3-dihydro-1H-inden-5-amine | 7.5 | 497 | — | B Variant 1 |
| 46 | H | N-ethyl-2,6-difluoroaniline | 7.5 | 493 | — | B Variant 1 |
| 47 | H | N-ethyl-2-methyl-6-ethylaniline | 7.5 | 499 | — | B Variant 1 |
| 48 | H | 4-bromo-2-fluoro-N-ethylaniline | 7.5 | 553 | — | B Variant 1 |
| 49 | H | N-(3-(ethylamino)phenyl)acetamide | 7.4 | 514 | — | B Variant 1 |
| 50 | H | N-ethyl-3,4-difluoroaniline | 7.4 | 493 | — | B Variant 1 |

TABLE 1-continued
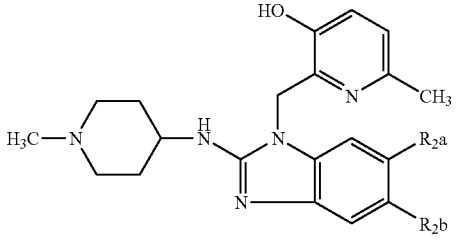
| Comp. No. | R2b | R2a | Activity | Mass (MH+) | Melting point/salt | Synthesis scheme |
|---|---|---|---|---|---|---|
| 51 | H | 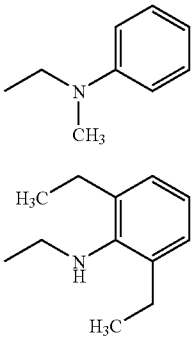 | 7.4 | 471 | — | B Variant 1 |
| 52 | H | 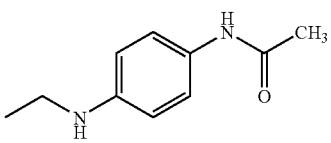 | 7.4 | 513 | — | B Variant 1 |
| 53 | H | 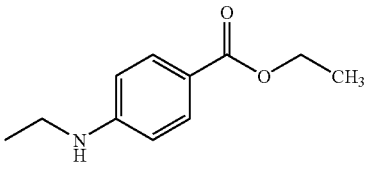 | 7.4 | 514 | — | B Variant 1 |
| 54 | H | 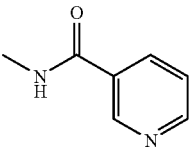 | 7.4 | 529 | — | B Variant 1 |
| 55 | 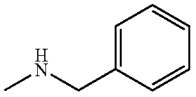 | H | 7.3 | 472 | — | E |
| 56 | H | 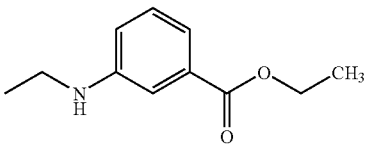 | 7.3 | 457 | 225° C. | F |
| 57 | H | 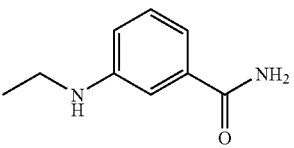 | 7.3 | 529 | 205° C. | B Variant 2 |
| 58 | H |  | 7.3 | 500 | — | B Variant 1 |

TABLE 1-continued

| Comp. No. | R2b | R2a | Activity | Mass (MH+) | Melting point/salt | Synthesis scheme |
|---|---|---|---|---|---|---|
| 59 | H | N-benzyl-N-ethyl-N',N'-dimethylethylenediamine | 7.3 | 542 | 185° C./ HCl salt | A |
| 60 | H | 3-fluoro-4-methyl-N-ethylaniline | 7.3 | 489 | — | B Variant 1 |
| 61 | H | 3,4-dimethoxy-N-ethylaniline | 7.3 | 517 | — | B Variant 1 |
| 62 | H | N-ethyl-N-methylaniline | 7.3 | 485 | 233° C. | A |
| 63 | H | 4-bromo-2-methyl-N-ethylaniline | 7.3 | 549 | — | B Variant 1 |
| 64 | H | N-ethyl-N'-phenyl-1,4-phenylenediamine | 7.3 | 548 | — | B Variant 1 |
| 65 | H | 3-methyl-N-methylbenzamide | 7.2 | 485 | — | E |

TABLE 1-continued

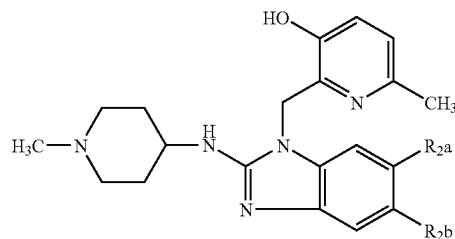

| Comp. No. | R2b | R2a | Activity | Mass (MH+) | Melting point/salt | Synthesis scheme |
|---|---|---|---|---|---|---|
| 66 | H | 3-(phenoxy)-N-ethylaniline | 7.2 | 549 | — | B Variant 1 |
| 67 | H | 4-methoxy-3-fluoro-N-ethylaniline | 7.2 | 505 | — | B Variant 1 |
| 68 | H | 4-bromo-3-methyl-N-ethylaniline | 7.2 | 549 | — | B Variant 1 |
| 69 | H | 4-bromo-3-fluoro-N-ethylaniline | 7.2 | 553 | — | B Variant 1 |
| 70 | H | 2,4-dichloro-N-ethylaniline | 7.2 | 525 | — | B Variant 1 |
| 71 | H | 4-trifluoromethyl-N-ethylaniline | 7.2 | 525 | — | B Variant 1 |
| 72 | H | ethyl 2-(ethylamino)benzoate | 7.1 | 529 | — | B Variant 1 |

TABLE 1-continued

| Comp. No. | R2b | R2a | Activity | Mass (MH+) | Melting point/salt | Synthesis scheme |
|---|---|---|---|---|---|---|
| 73 | H | 2-Cl-4-CH₃-N-ethyl-anilino | 7.1 | 505 | — | B Variant 1 |
| 74 | H | 2-ethyl-4-Br-N-ethyl-anilino | 7.1 | 563 | — | B Variant 1 |
| 75 | H | 2,6-dimethyl-N-ethyl-anilino | 7 | 485 | — | B Variant 1 |
| 76 | H | 4-isopropyl-N-ethyl-anilino | 7 | 499 | — | B Variant 1 |
| 77 | H | 2,4,5-trichloro-N-ethyl-anilino | 7 | 559 | — | B Variant 1 |
| 78 | N-methyl-3-methylbenzamide | H | 6.9 | 485 | — | E |
| 79 | H | 1-ethyl-imidazolyl | 6.9 | 432 | — | A |
| 80 | H | N-ethyl-N-phenyl-benzylamino | 6.9 | 547 | 249° C. | A |

TABLE 1-continued
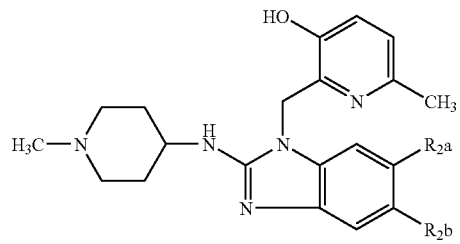
| Comp. No. | R2b | R2a | Activity | Mass (MH+) | Melting point/salt | Synthesis scheme |
|---|---|---|---|---|---|---|
| 81 | H | 5-bromo-1-ethylindoline | 6.9 | 561 | 184° C. | A |
| 82 | H | 2-ethylamino-3-isopropyl-6-methylphenyl | 6.9 | 513 | — | B variant 1 |
| 83 | H | 2-bromo-4-chloro-6-ethylaminophenyl | 6.9 | 569 | — | B Variant 1 |
| 84 | H | 4-methyl-1-propylphenyl | 6.8 | 470 | 224° C. | G |
| 85 | H | N-benzyl-N-(2-hydroxyethyl)ethylamine | 6.8 | 515 | 189° C. | A |
| 86 | H | 1-phenylethanol | 6.8 | 458 | 144° C. | |
| 87 | H | 4-bromo-2,6-dimethyl-ethylaminophenyl | 6.8 | 563 | — | B Variant 1 |

TABLE 1-continued
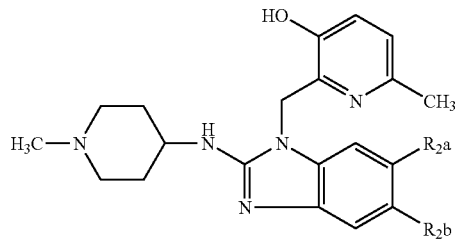
| Comp. No. | R2b | R2a | Activity | Mass (MH+) | Melting point/salt | Synthesis scheme |
|---|---|---|---|---|---|---|
| 88 | H | (2,4-dimethyl-6-chloro-N-ethylanilino) | 6.8 | 519 | — | B Variant 1 |
| 89 | H | (4-bromo-2-chloro-N-ethylanilino) | 6.8 | 569 | — | B Variant 1 |
| 90 | N-methylbenzamide | H | 6.7 | 471 | — | E |
| 91 | H | (4,5-dimethyl-2-mercapto-N-ethylanilino) | 6.7 | 517 | — | B Variant 1 |
| 92 | H | ethanol (CH₂CH₂OH) | 6.6 | 382 | 165° C. | A |
| 93 | H | (3-methylphenyl ethylsulfide) | 6.6 | 488 | 202° C. | C |
| 94 | H | (4-bromo-N-ethyl-1-naphthylamino) | 6.6 | 585 | — | B Variant 1 |
| 95 | H | N-ethyl-N,N-dibenzylamine | 6.6 | 547 | — | A |

TABLE 1-continued
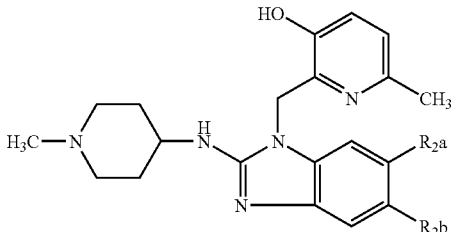
| Comp. No. | R2b | R2a | Activity | Mass (MH+) | Melting point/salt | Synthesis scheme |
|---|---|---|---|---|---|---|
| 96 | H | 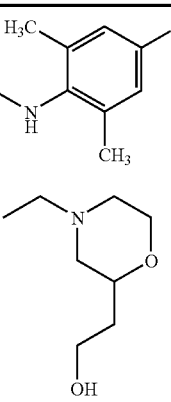 | 6.6 | 499 | — | B Variant 1 |
| 97 | H | 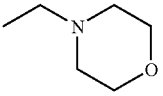 | 6.6 | 495 | 171° C. | A |
| 98 | H | 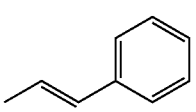 | 6.5 | 451 | 224° C. | A |
| 99 | H | 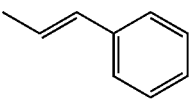 | 6.4 | 454 | 262° C. | G |
| 100 | 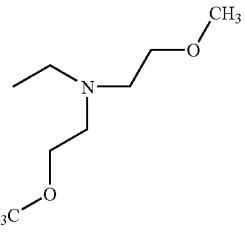 | H | 6.4 | 454 | >260° C. | G |
| 101 | H | H | 6.4 | 352 | >260° C. | G |
| 102 | H | 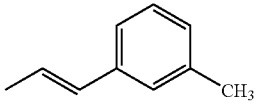 | 6.4 | 497 | — | A |
| 103 | H | 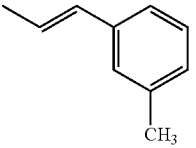 | 6.3 | 468 | 244° C. | G |
| 104 |  | H | 6.2 | 468 | 261° C. | G |

TABLE 1-continued

| Comp. No. | R2b | R2a | Activity | Mass (MH+) | Melting point/salt | Synthesis scheme |
|---|---|---|---|---|---|---|
| 105 | H | N-ethyl-N-methyl-phenethylamine | 6.2 | 499 | — | A |
| 106 | H | N-methyl-3-phenylpropanamide | 6.1 | 499 | — | E |
| 107 | H | N-methyl-2-phenylacetamide | 6.1 | 485 | — | E |
| 108 | H | N-methyl-2-(pyridin-2-yl)acetamide | 6 | 486 | — | E |
| 109 | H | 2-(ethyl(butyl)amino)ethanol | 6 | 481 | — | A |
| 110 | H | N-ethyl-phenethylamine | 5.8 | 485 | 102° C. | B Variant 2 |
| 111 | H | 2-(diethylamino)ethanol derivative | 5.6 | 453 | — | A |

103 104
TABLE 1-continued
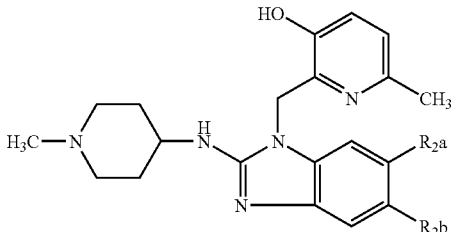
| Comp. No. | R2b | R2a | Activity | Mass (MH+) | Melting point/salt | Synthesis scheme |
|---|---|---|---|---|---|---|
| 112 | H | 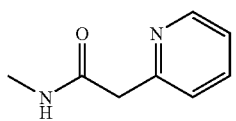 | 5.5 | 471 | 169° C. | D |
| 113 | 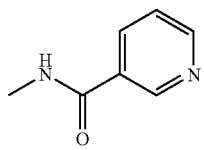 | H | 5.5 | 486 | — | E |
| 114 | H | 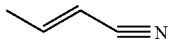 | 5.2 | 472 | — | E |
| 115 | 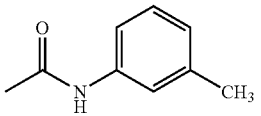 | H | 5.1 | 403 | 188° C. | J |
| 116 | H | 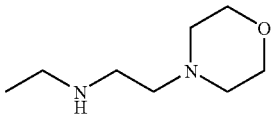 | 5.1 | 485 | 172° C. | D |
| 117 | H | 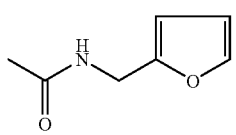 | 5.1 | 494 | 161° C. | B Variant 2 |
| 118 | 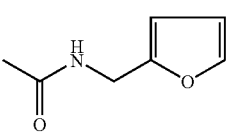 | H | 4.9 | 475 | 250° C. | D |
| 119 | H | 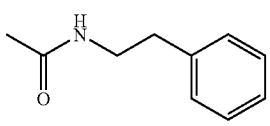 | 4.8 | 475 | 155° C. | D |
| 120 | 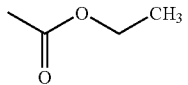 | H | 4.6 | 499 | 200° C. | D |
| 121 | 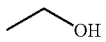 | H | <4 | 424 | 243° C. | D |
| 122 | OH | H | <4 | 382 | >260° C. | A |

TABLE 1-continued

| Comp. No. | R2b | R2a | Activity | Mass (MH+) | Melting point/salt | Synthesis scheme |
|---|---|---|---|---|---|---|
| 123 | phenylpropyl | H | 4.7 | 456 | 159° C. | G |
| 124 | 3-methylphenylpropyl | H | 5.1 | 470 | 196° C. | G |
| 125 | 4-methylphenylpropenyl | H | <4 | 468 | 229° C. | G |
| 126 | H | 4-chlorophenylpropenyl | <4 | 488 | 248° C. | G |
| 127 | 4-chlorophenylpropenyl | H | <4 | 488 | 225° C. | G |
| 128 | H | 4-methylphenylpropenyl | <4 | 468 | 250° C. | G |
| 129 | 4-methylphenylpropyl | H | <4 | 470 | 222° C. | G |
| 130 | N-ethyl-3-methylaniline | H | 4.6 | 471 | 156° C. | B Variant 2 |
| 131 | N-ethylaniline | H | <4 | 457 | 199° C. | B Variant 2 |
| 132 | 3-methylphenyl ethylsulfide | H | <4 | 488 | 208° C. | C |

TABLE 1-continued
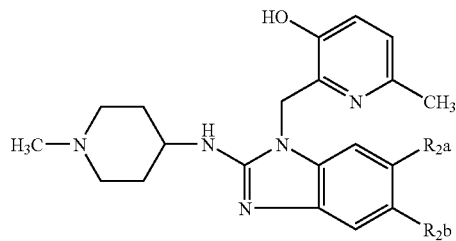
| Comp. No. | R2b | R2a | Activity | Mass (MH+) | Melting point/salt | Synthesis scheme |
|---|---|---|---|---|---|---|
| 133 | propyl-NH₂ | H | <4 | 409 | 245° C. | J |
| 134 | H | acetamidomethyl-2-pyridyl | <4 | 486 | 146° C. | D |
| 135 | acetamidomethyl-2-pyridyl | H | <4 | 486 | 230° C. | D |
| 136 | H | N-phenethyl acetamide | <4 | 499 | 194° C. | D |
| 137 | H | N-ethyl-bis(2-cyanoethyl)amine | <4 | 487 | — | A |
| 138 | H | 3,5-dimethylphenyl-N-ethyl-butanamide | 9.6 | 570 | 180° C. | A |

TABLE 2a
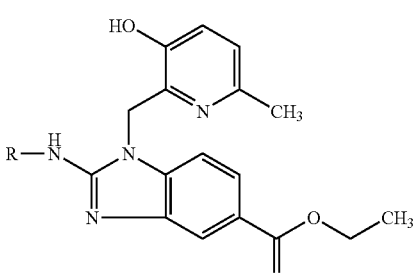
| Comp. No. | R | Activity | Mass (MH+) | Melting point/ salt | Synthesis scheme |
|---|---|---|---|---|---|
| 139 | 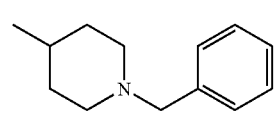 | 5.1 | 410 | 164° C. | D |
| 140 | 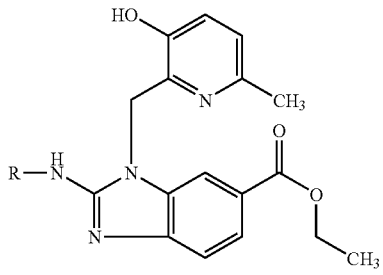 | <4 | 500 | 238° C. | A |
TABLE 2b
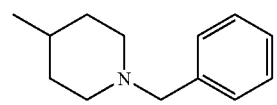
| Comp. No. | R | Activity | Mass (MH+) | Melting point/ salt | Synthesis scheme |
|---|---|---|---|---|---|
| 141 | 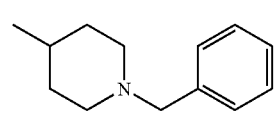 | C | 410 | 262° C. | D |
| 142 | 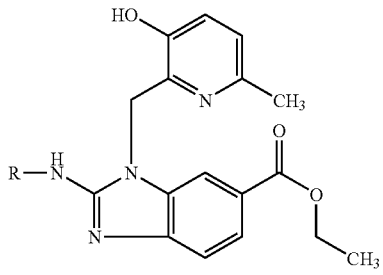 | C | 500 | 179° C. | A |

TABLE 3
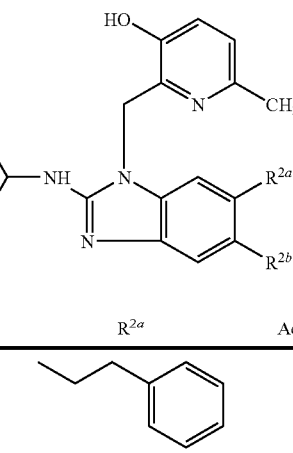
| Comp. No. | R | R²ᵇ | R²ᵃ | Activity | Mass (MH+) | Melting point/ salt | Synthesis scheme |
|---|---|---|---|---|---|---|---|
| 143 | —CH₂—NH₂ | H | 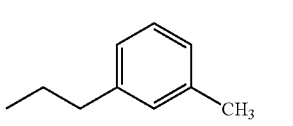 | 9 | 485 | 181° C./HCl | G |
| 144 | —CH₂—NH₂ | H | 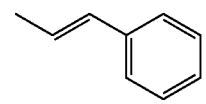 | 9 | 499 | 188° C./HCl | G |
| 145 | —CH₂—NH₂ | 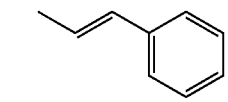 | H | 9 | 483 | >260° C./HCl | G |
| 146 | —CH₂—NH₂ | H | 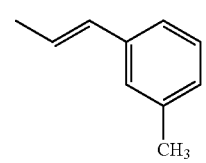 | 8.9 | 483 | 260° C./HCl | G |
| 147 | —CH₂—NH₂ | 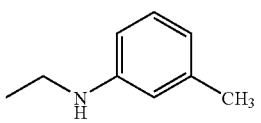 | H | 8.8 | 497 | 210° C./HCl | G |
| 148 | —CH₂—OH | H | 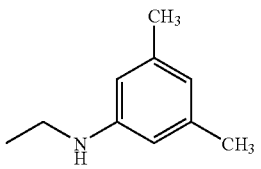 | 8.8 | 501 | 137° C. | H |
| 149 | —CH₂—OH | H | 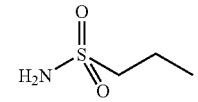 | 8.8 | 515 | 133° C. | H |
| 150 | 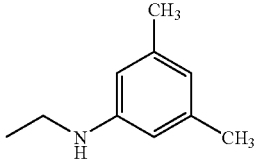 | H | 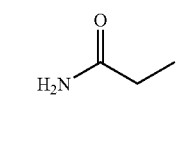 | 8.6 | 592 | 142° C. | K |
| 151 | 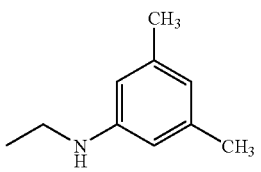 | H |  | 8.6 | 542 | 206° C. | L |

TABLE 3-continued
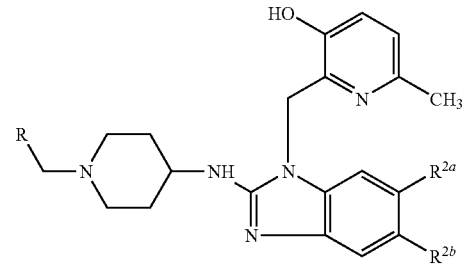
| Comp. No. | R | R²ᵇ | R²ᵃ | Activity | Mass (MH+) | Melting point/ salt | Synthesis scheme |
|---|---|---|---|---|---|---|---|
| 152 | —(CH₂)₂—OH | H | 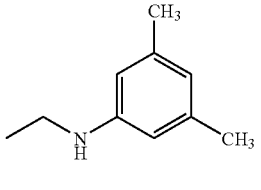 | 8.6 | 529 | 144° C. | M |
| 153 | —CH₂—NH₂ | H | 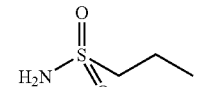 | 8.5 | 513 | 211° C./HCl | G |
| 154 | 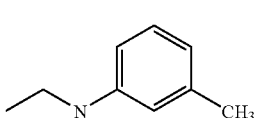 | H |  | 8.5 | 578 | 193° C. | K |
| 155 | 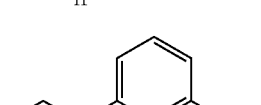 | H | 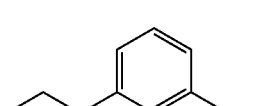 | 8.5 | 528 | 145° C. | L |
| 156 | 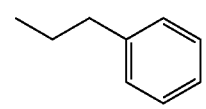 | H | 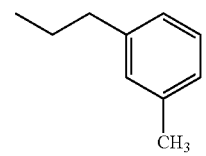 | 8.4 | 515 | — | M |
| 157 | H₂N—CH₂— | 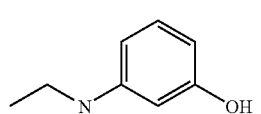 | H | 7.9 | 485 | 183° C./HCl | G |
| 158 | H₂N—CH₂— | 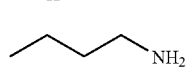 | H | 7.9 | 499 | 179° C./HCl | G |
| 159 | HO—CH₂— | H | 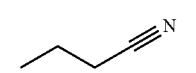 | 7.9 | 503 | 158° C. | H |
| 160 | HO—CH₂— | H |  | 7.9 | 439 | 185° C./HCl | J |
| 161 | HO—CH₂— | H |  | 7.8 | 435 | 207° C. | J |

TABLE 3-continued

Structure: Common scaffold with substituents R, R²ᵃ, R²ᵇ on a benzimidazole core with piperidine-NH linker and hydroxymethylpyridine group.

| Comp. No. | R | R²ᵇ | R²ᵃ | Activity | Mass (MH+) | Melting point/ salt | Synthesis scheme |
|---|---|---|---|---|---|---|---|
| 162 | HO—CH₂— | H | 3-phenylpropyl | 7.5 | 486 | 201° C. | G |
| 163 | H₂N—C(O)—CH₂— | H | 3-phenylpropyl | 7.2 | 513 | 202° C. | G |
| 164 | phenyl | H | N-ethyl-3,5-dimethylanilino | 7.2 | 561 | 186° C. | H |
| 165 | phenyl | H | N-ethyl-3,5-dichloroanilino | 7.1 | 601 | 149° C. | H |
| 166 | H₂N—C(O)—CH₂— | (E)-styryl | H | 6.8 | 511 | — | G |
| 167 | phenyl | H | N-ethyl-3-methylanilino | 6.8 | 547 | 198° C. | H |
| 168 | HO—CH₂— | 3-phenylpropyl | H | 6.6 | 486 | 216° C. | G |
| 169 | HO—CH₂— | H | (E)-styryl | 6.6 | 484 | 240° C. | G |
| 170 | H₂N—C(O)—CH₂— | 3-phenylpropyl | H | 5.7 | 513 | 160° C. | G |

TABLE 4
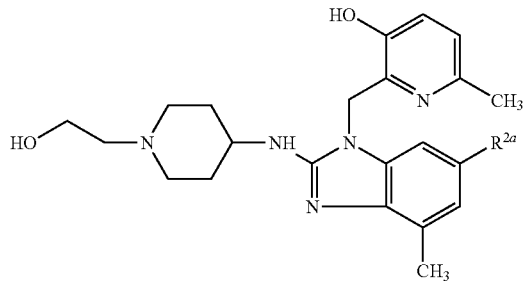
| Comp. No. | R²ᵃ | Activity | Mass (MH+) | Melting point/ salt | Synthesis scheme |
|---|---|---|---|---|---|
| 171 | 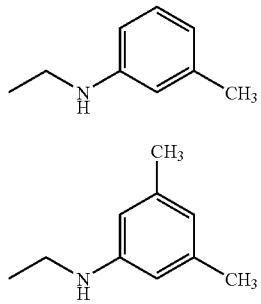 | 8.5 | 515 | 123° C. | I |
| 172 | 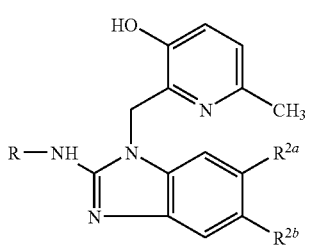 | 8.5 | 529 | 136° C. | I |
TABLE 5
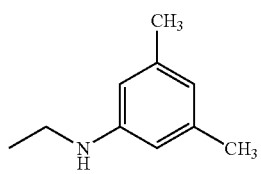
| Comp. No. | R | R²ᵇ | R²ᵃ | Activity | Mass (MH+) | Melting point/ salt | Synthesis scheme |
|---|---|---|---|---|---|---|---|
| 173 | 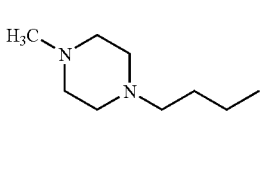 | H | 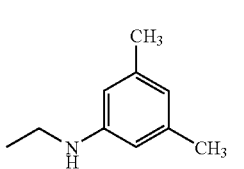 | 8.8 | 513 | 161° C. | N |
| 174 | H₃C–N piperazine–N–(CH₂)₃– | H | 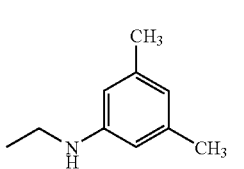 | 8.4 | 528 | 150° C. | O |

TABLE 5-continued
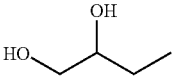
| Comp. No. | R | R[2b] | R[2a] | Activity | Mass (MH+) | Melting point/ salt | Synthesis scheme |
|---|---|---|---|---|---|---|---|
| 175 | 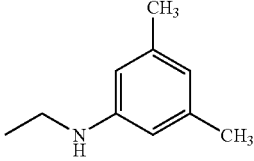 | H |  | 7.5 | 462 | 128° C. | P |
| 176 | 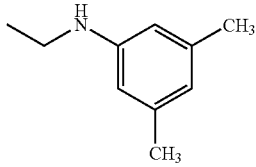 | 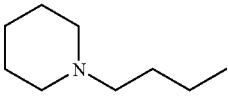 | H | 7.2 | 513 | 182° C. | N |
| 177 | 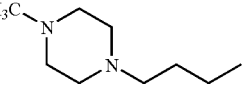 | H | —CH$_2$—OH | 7.1 | 410 | 220° C. | N |
| 178 | 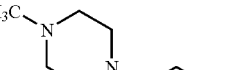 | H | —CH$_2$—OH | 6.5 | 425 | 230° C. | O |
| 179 | 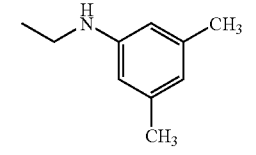 | 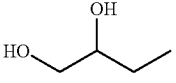 | H | 6.2 | 528 | 193° C. | O |
| 180 | 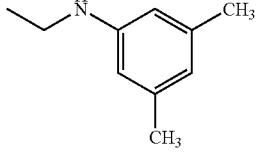 | 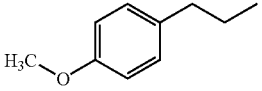 | H | 5.6 | 462 | 215° C. | P |
| 181 |  | H | —CH$_2$—OH | 5.1 | 419 | 194° C. | Q |
| 182 | 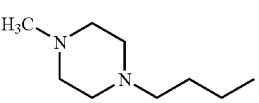 | —CH$_2$—OH | H | 5 | 410 | 146° C. | N |
| 183 | H$_3$C\N\_/N\_/\_/ | —CH$_2$—OH | H | 5 | 425 | 154° C. | O |

TABLE 5-continued

[Structure: benzimidazole with N1-CH2-(3-hydroxy-6-methylpyridin-2-yl), C2-NH-R, and R2a, R2b substituents on benzene ring]

| Comp. No. | R | R2b | R2a | Activity | Mass (MH+) | Melting point/ salt | Synthesis scheme |
|---|---|---|---|---|---|---|---|
| 184 | 2,2-dimethyl-1,3-dioxolan-4-yl-ethyl | H | 3,5-dimethyl-N-ethyl-anilino | <4 | 502 | 212° C. | P |
| 185 | phenethyl | —CH2—OH | H | <4 | 389 | 230° C. | Q |
| 186 | phenethyl | 3,5-dimethyl-N-ethyl-anilino | H | <4 | 492 | 175° C. | Q |
| 187 | phenethyl | H | 3,5-dimethyl-N-ethyl-anilino | <4 | 492 | 190° C. | Q |
| 188 | phenethyl | H | —CH2—OH | 4.4 | 389 | 185° C. | Q |
| 189 | 2-(4-methoxyphenyl)ethyl | —CH2—OH | H | <4 | 419 | 185° C. | Q |
| 190 | 2-(4-methoxyphenyl)ethyl | H | 3,5-dimethyl-N-ethyl-anilino | <4 | 522 | 178° C. | Q |
| 191 | 2-(4-methoxyphenyl)ethyl | 3,5-dimethyl-N-ethyl-anilino | H | <4 | 522 | 196° C. | Q |

TABLE 5-continued

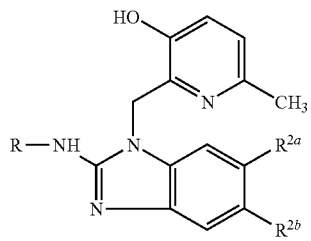

| Comp. No. | R | $R^{2b}$ | $R^{2a}$ | Activity | Mass (MH+) | Melting point/ salt | Synthesis scheme |
|---|---|---|---|---|---|---|---|
| 192 | 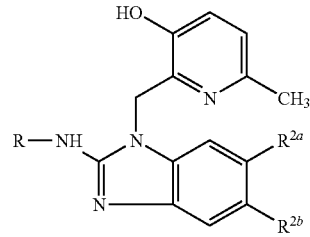 | H | ![Cl-phenyl-NHEt-Cl structure] | <4 | 532 | 211° C. | Q |

Example 18

In Vitro Screening for Activity Against Respiratory Syncytial Virus

The percent protection against cytopathology caused by viruses (antiviral activity or $EC_{50}$) achieved by tested compounds and their cytotoxicity ($CC_{50}$) are both calculated from dose-response curves. The selectivity of the antiviral effect is represented by the selectivity index (SI), calculated by dividing the $CC_{50}$ (cytotoxic dose for 50% of the cells) by the $EC_{50}$ (antiviral activity for 50% of the cells). The tables in the above experimental part list the category to which each of the prepared compounds belong. Compounds belonging to activity category "A" have an $pEC_{50}$ (−log of $EC_{50}$ when expressed in molar units) equal to or more than 7. Compounds belonging to activity category "B" have a pEC50 value between 6 and 7. Compounds belonging to activity category "C" have a pEC50 value equal to or below 6.

Automated tetrazolium-based calorimetric assays were used for determination of $EC_{50}$ and $CC_{50}$ of test compounds. Flat-bottom, 96-well plastic microtiter trays were filled with 180 μl of Eagle's Basal Medium, supplemented with 5% FCS (0% for FLU) and 20 mM Hepes buffer. Subsequently, stock solutions (7.8× final test concentration) of compounds were added in 45 μl volumes to a series of triplicate wells so as to allow simultaneous evaluation of their effects on virus- and mock-infected cells. Five five-fold dilutions were made directly in the microtiter trays using a robot system. Untreated virus controls, and HeLa cell controls were included in each test. Approximately 100 $TCID_{50}$ of Respiratory Syncytial Virus was added to two of the three rows in a volume of 50 μl. The same volume of medium was added to the third row to measure the cytotoxicity of the compounds at the same concentrations as those used to measure the antiviral activity. After two hours of incubation, a suspension (4×10⁵ cells/ml) of HeLa cells was added to all wells in a volume of 50 μl. The cultures were incubated at 37° C. in a 5% $CO_2$ atmosphere. Seven days after infection the cytotoxicity and the antiviral activity was examined spectrophotometrically. To each well of the microtiter tray, 25 μl of a solution of MTT (3-(4,5-dimethylthiazol-2-yl)-2,5-diphenyltetrazolium bromide) was added. The trays were further incubated at 37° C. for 2 hours, after which the medium was removed from each cup. Solubilization of the formazan crystals was achieved by adding 100 μl 2-propanol. Complete dissolution of the formazan crystals were obtained after the trays have been placed on a plate shaker for 10 min. Finally, the absorbances were read in an eight-channel computer-controlled photometer (Multiskan MCC, Flow Laboratories) at two wavelengths (540 and 690 nm). The absorbance measured at 690 nm was automatically subtracted from the absorbance at 540 nm, so as to eliminate the effects of non-specific absorption.

The invention claimed is:

1. A compound of the formula

![structure]

a prodrug, N-oxide, addition salt, quaternary amine, metal complex or stereochemically isomeric form thereof wherein
R is $C_{1-6}$alkyl substituted with one or with two substituents each independently selected from the group consisting of trifluoromethyl, $NR^{7a}R^{7b}$, $Ar^2$, hydroxy, $C_{1-4}$alkoxy, $Ar^2(CH_2)_n$oxy, hydroxycarbonyl, aminocarbonyl, $C_{1-4}$alkylcarbonyl, $C_{1-4}$alkoxycarbonyl, $Ar^2(CH_2)_n$carbonyl, aminocarbonyloxy, $C_{1-4}$alkylcarbonyloxy, $Ar^2$carbonyloxy, mono- or di($C_{1-4}$alkyl)aminocarbonyl, aminosulfonyl, mono- or di($C_{1-4}$alkyl)aminosulfonyl and a heterocycle selected from the group consisting of pyrrolidinyl, imidazolyl, piperidinyl, homopiperidinyl, piperazinyl, dioxolanyl, dioxanyl, di-$C_{1-6}$alkyl-dioxolanyl and pyridyl, wherein each of said heterocycle may optionally be substituted with with one or two radicals selected from oxo and $C_{1-6}$alkyl;
$R^{7a}$ is hydrogen, $C_{1-6}$alkyl, formyl or $C_{1-6}$alkylcarbonyl;
$R^{7b}$ is hydrogen, $C_{1-6}$alkyl, formyl or $C_{1-6}$alkylcarbonyl;
one of $R^{2a}$ and $R^{2b}$ is cyano$C_{1-6}$alkyl, cyano$C_{2-6}$alkenyl, $Ar^3C_{1-6}$alkyl, $(Ar^3)(OH)C_{1-6}$alkyl, Het-$C_{1-6}$alkyl, $N(R^{8a}R^{8b})C_{1-6}$alkyl, $Ar^3C_{2-6}$alkenyl, Het-$C_{2-6}$alkenyl, $Ar^3$amino$C_{1-6}$alkyl, Het-amino$C_{1-6}$alkyl, Het-$C_{1-6}$alkylamino$C_{1-6}$alkyl, $Ar^3$thio$C_{1-6}$alkyl, Het-thio$C_{1-6}$alkyl, $Ar^3$sulfonyl$C_{1-6}$alkyl, Het-sulfonyl$C_{1-6}$alkyl, Ar³aminocarbonyl, Het-aminocarbonyl, Ar³(CH₂)ₙaminocarbonyl, Het-(CH₂)ₙaminocarbonyl, Ar³carbonylamino, Het-carbonylamino, Ar³(CH₂)ₙcarbonylamino, Het-(CH₂)ₙcarbonylamino, or Ar³(CH₂)ₙamino; and the other one of $R^{2a}$ and $R^{2b}$ is hydrogen;

$R^{8a}$ is Ar³, $C_{1-6}$alkyl, hydroxy$C_{1-6}$alkyl, $C_{1-6}$alkoxy$C_{1-6}$alkyl, cyano$C_{1-6}$alkyl, amino$C_{1-6}$alkyl, mono-or di($C_{1-6}$alkyl)amino$C_{1-6}$alkyl, Ar³$C_{1-6}$alkyl, Het-$C_{1-6}$alkyl, aminocarbonyl-$C_{1-6}$-alkyl, hydrogen, or carboxyl-$C_{1-6}$-alkyl;

$R^{8b}$ is Ar³, $C_{1-6}$alkyl, hydroxy$C_{1-6}$alkyl, $C_{1-6}$alkoxy$C_{1-6}$alkyl, cyano$C_{1-6}$alkyl, amino$C_{1-6}$alkyl, mono-or di($C_{1-6}$alkyl)amino$C_{1-6}$alkyl, Ar³$C_{1-6}$alkyl, hydrogen, or Het-$C_{1-6}$alkyl;

Ar³ is phenyl, naphthalenyl, 1,2,3,4-tetrahydro-naphthalenyl or indanyl, wherein said phenyl, naphtyl, 1,2,3,4-tetrahydro-naphthalenyl or indanyl may optionally and each individually be substituted with 1 to 4 substituents selected from the group consisting of halo, hydroxy, mercapto, amino, cyano, $C_{1-6}$alkyl, $C_{2-6}$alkenyl, $C_{2-6}$alkynyl, Ar¹, hydroxy$C_{1-6}$alkyl, polyhalo$C_{1-6}$alkyl, amino$C_{1-6}$alkyl, cyano$C_{1-6}$alkyl, aminocarbonyl, $C_{1-6}$alkyloxy, $C_{1-6}$alkylthio, Ar¹-oxy, Ar¹-thio, Ar¹-amino, aminosulfonyl, aminocarbonyl-$C_{1-6}$alkyl, hydroxycarbonyl-$C_{1-6}$alkyl, hydroxycarbonyl, $C_{1-4}$alkylcarbonyl, mono- or di($C_{1-4}$alkyl)amino, mono- or di($C_{1-4}$alkyl)aminocarbonyl, mono- or di($C_{1-4}$alkyl)aminosulfonyl, mono- or di($C_{1-4}$alkyl)amino$C_{1-6}$alkyl, $C_{1-4}$alkylcarbonylamino and $C_{1-4}$alkoxycarbonyl;

Ar¹ is phenyl or phenyl substituted with 1 to 4 substituents selected from the group consisting of halo, hydroxy, $C_{1-6}$alkyl, hydroxy$C_{1-6}$alkyl, polyhalo$C_{1-6}$alkyl, and $C_{1-6}$alkyloxy;

Ar² is phenyl or phenyl substituted with 1 to 4 substituents selected from the group consisting of halo, hydroxy, amino, cyano, $C_{1-6}$alkyl, hydroxy$C_{1-6}$alkyl, polyhalo$C_{1-6}$alkyl, amino$C_{1-6}$alkyl, $C_{1-6}$alkyloxy, aminosulfonyl, aminocarbonyl, hydroxycarbonyl, $C_{1-4}$alkylcarbonyl, mono- or di($C_{1-4}$alkyl)amino, mono- or di($C_{1-4}$alkyl)aminocarbonyl, mono- or di($C_{1-4}$alkyl)aminosulfonyl, mono- or di($C_{1-4}$alkyl)amino$C_{1-6}$alkyl and $C_{1-4}$alkoxycarbonyl; and Het is a heterocycle selected from the group consisting of tetrahydrofuranyl, tetrahydrothienyl, dioxanyl, dioxolanyl, pyrrolidinyl, pyrrolidinonyl, furanyl, thienyl, pyrrolyl, thiazolyl, oxazolyl, imidazolyl, isothiazolyl, pyrazolyl, isoxazolyl, oxadiazolyl, thiadiazolyl, piperidinyl, homopiperidinyl, piperazinyl, morpholinyl, pyridyl, pyrazinyl, pyridazinyl, pyrimidinyl, tetrahydroquinolinyl, quinolinyl, isoquinolinyl, benzodioxanyl, benzodioxolyl, indolinyl, and indolyl; each of said heterocycles may optionally be substituted with oxo, amino, Ar¹, $C_{1-4}$alkyl, amino$C_{1-4}$alkyl, hydroxy$C_{1-6}$alkyl, Ar¹$C_{1-4}$alkyl, mono- or di($C_{1-6}$alkyl)amino$C_{1-6}$alkyl, mono- or di($C_{1-6}$alkyl)amino, or with two $C_{1-4}$alkyl radicals. mono- or di($C_{1-6}$alkyl)amino, or with two $C_{1-4}$alkyl radicals.

2. A compound according to claim 1, wherein one of $R^{2a}$ and $R^{2b}$ is selected from cyano$C_{1-6}$alkyl, cyano $C_{2-6}$alkenyl, Ar³$C_{1-6}$alkyl, (Ar³)(OH) $C_{1-6}$alkyl, Het- $C_{1-6}$alkyl, N($R^{8a}R^{8b}$) $C_{1-6}$alkyl, Ar³$C_{2-6}$alkenyl, Het-$C_{2-6}$alkenyl, Ar³amino$C_{1-6}$alkyl, Het-amino $C_{1-6}$alkyl, Het-$C_{1-6}$alkylamino$C_{1-6}$alkyl, Ar³thio$C_{1-6}$alkyl, Het-thio$C_{1-6}$alkyl, Ar³sulfonyl$C_{1-6}$alkyl, Het-sulfonyl$C_{1-6}$alkyl, Ar³aminocarbonyl, Het-aminocarbonyl, Ar³(CH₂)ₙaminocarbonyl, Het-(CH₂)ₙaminocarbonyl, Ar³carbonylamino, or Ar³(CH₂)ₙamino; and the other one of $R^{2a}$ and $R^{2b}$ is hydrogen.

3. A compound according to claim 1, wherein one of $R^{2a}$ and $R^{2b}$ is selected from cyano$C_{1-6}$alkyl, Ar³$C_{1-6}$alkyl, Het-$C_{1-6}$alkyl, N($R^{8a}R^{8b}$)$C_{1-6}$alkyl, Ar³$C_{2-6}$alkenyl, Ar³amino$C_{1-6}$alkyl, Het-amino$C_{1-6}$alkyl, Het-$C_{1-6}$alkylamino$C_{1-6}$alkyl, Ar³thio$C_{1-6}$alkyl, Ar³aminocarbonyl, Het-aminocarbonyl, Ar³(CH₂)ₙaminocarbonyl, or Het-(CH₂)ₙaminocarbonyl; and the other one of $R^{2a}$ and $R^{2b}$ is hydrogen.

4. A compound according to claim 1, wherein one of $R^{2a}$ and $R^{2b}$ is selected from N($R^{8a}R^{8b}$)$C_{1-6}$alkyl, or Ar³amino$C_{1-6}$alkyl; and the other one of $R^{2a}$ and $R^{2b}$ is hydrogen.

5. A compound according to claim 1, wherein R is $C_{1-6}$alkyl substituted with Ar² or hydroxyl, or $C_{1-6}$alkyl substituted with two 5ydroxyl radicals, or $C_{1-6}$alkyl substituted with di-$C_{1-6}$alkyl-dioxolanyl, pyrrolidinyl, piperidinyl, piperazinyl, or 4-$C_{1-6}$alkyl-piperazinyl.

6. A compound according to claim 1, wherein $R^{8a}$ is Ar³, $C_{1-6}$alkyl, hydroxy$C_{1-6}$alkyl, $C_{1-6}$alkoxy$C_{1-6}$alkyl, cyano$C_{1-6}$alkyl, amino $C_{1-6}$alkyl, mono-or di($C_{1-6}$alkyl)amino$C_{1-6}$alkyl, Ar³$C_{1-6}$alkyl, Het-$C_{1-6}$alkyl, amino carbonyl-$C_{1-6}$alkyl, or carboxyl-$C_{1-6}$-alkyl; and $R^{8b}$ is Ar³.

7. A compound according to claim 1, wherein $R^{8a}$ is $C_{1-6}$alkyl, hydroxy$C_{1-6}$alkyl, Ar³$C_{1-6}$alkyl, Het-$C_{1-6}$alkyl, or aminocarbonyl-$C_{1-6}$-alkyl; and $R^{8b}$ is $C_{1-6}$alkyl, hydroxy$C_{1-6}$alkyl, Ar³$C_{1-6}$alkyl, or Het-$C_{1-6}$alkyl.

8. A compound according to claim 1, wherein Ar³ is phenyl optionally substituted with one, two or three substituents selected from halo, hydroxyl, mercapto, amino, cyano, $C_{1-6}$alkyl, $C_{2-6}$alkenyl, $C_{2-6}$alkynyl, Ar¹, hydroxy$C_{1-6}$alkyl, CF₃, amino$C_{1-6}$alkyl, cyano$C_{1-6}$alkyl, aminocarbonyl, $C_{1-6}$alkyloxy, $C_{1-6}$alkylthio, Ar¹-oxy, Ar¹-thio, Ar¹-amino, aminosulfonyl, aminocarbonyl-$C_{1-6}$alkyl, hydroxycarbonyl-$C_{1-6}$alkyl, hydroxycarbonyl, $C_{1-4}$alkylcarbonyl, $C_{1-4}$alkylcarbonylamino or $C_{1-4}$alkoxycarbonyl.

9. A compound according to claim 8, wherein Ar³ is phenyl substituted with one, two or three substituents selected from halo, $C_{1-6}$alkyl or hydroxy$C_{1-6}$alkyl.

10. A compound according to claim 8, wherein Ar³ is phenyl substituted with two substituents which are methyl and hydroxyl.

11. A compound according to claim 10, in which the R, $R^{2a}$ and $R^{2b}$ substituents are as follows:

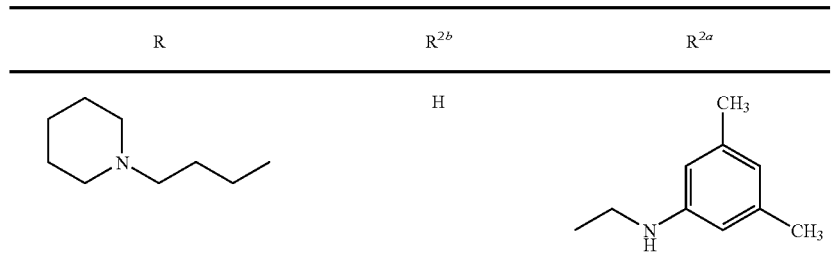

-continued
| R | $R^{2b}$ | $R^{2a}$ |
|---|---|---|
| 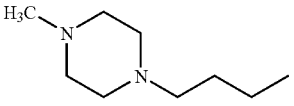 | H | 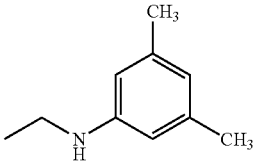 |
| 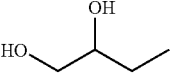 | H | 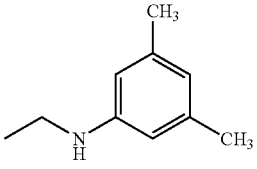 |
| 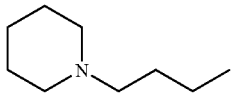 | 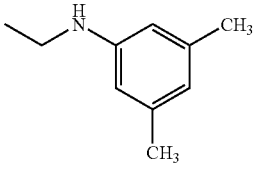 | H |
| 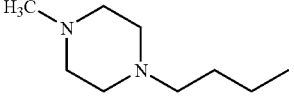 | 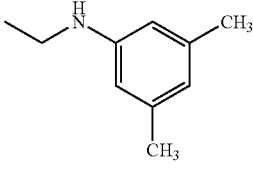 | H |
| 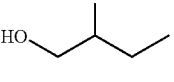 | 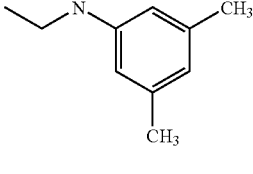 | H |
| 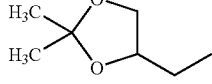 | H | 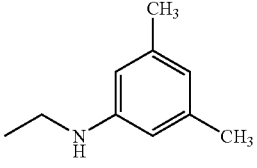 |
| 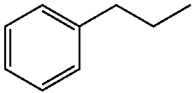 | 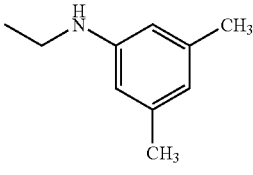 | H |
| 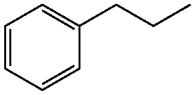 | H | 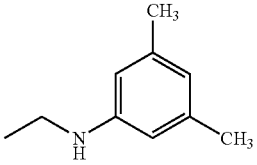 |
| 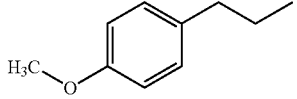 | H | 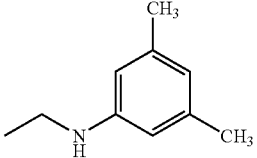 |

-continued
| R | R$^{2b}$ | R$^{2a}$ |
|---|---|---|
| 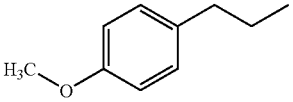 | 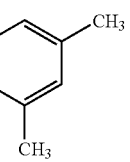 | H or |
| 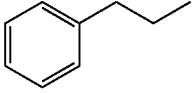 | H | 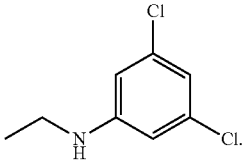 |
12. A pharmaceutical composition comprising a pharmaceutically acceptable carrier, and as active ingredient a therapeutically effective amount of a compound as claimed in claim 1.
* * * * *